US010822379B1

(12) United States Patent
Dimitrov et al.

(10) Patent No.: US 10,822,379 B1
(45) Date of Patent: Nov. 3, 2020

(54) MOLECULES THAT BIND TO SARS-COV-2

(71) Applicant: University of Pittsburgh—Of the Commonwealth System of Higher Education, Pittsburgh, PA (US)

(72) Inventors: Dimiter Stanchev Dimitrov, Pittsburgh, PA (US); Chuan Chen, Pittsburgh, PA (US); Dontcho V. Jelev, Rockville, MD (US); John W. Mellors, Pittsburgh, PA (US); Wei Li, Pittsburgh, PA (US); Zehua Sun, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/931,939

(22) Filed: May 14, 2020

Related U.S. Application Data

(60) Provisional application No. 62/988,856, filed on Mar. 12, 2020.

(51) Int. Cl.
| | |
|---|---|
| *A61K 39/395* | (2006.01) |
| *A61K 39/42* | (2006.01) |
| *A61K 39/15* | (2006.01) |
| *C07K 14/165* | (2006.01) |

(52) U.S. Cl.
CPC ............ *C07K 14/165* (2013.01); *A61K 39/15* (2013.01); *A61K 39/395* (2013.01); *C07K 2317/56* (2013.01); *C07K 2319/55* (2013.01)

(58) Field of Classification Search
None
See application file for complete search history.

(56) References Cited

U.S. PATENT DOCUMENTS

| | | | |
|---|---|---|---|
| 2019/0233498 | A1 | 8/2019 | Loomis et al. |
| 2019/0233522 | A1 | 8/2019 | Forssmann et al. |
| 2019/0241667 | A1 | 8/2019 | Papadopoulos et al. |

FOREIGN PATENT DOCUMENTS

| | | |
|---|---|---|
| WO | WO 98/22143 | 5/1998 |
| WO | WO 98/46778 | 10/1998 |
| WO | WO 00/17376 | 3/2000 |

OTHER PUBLICATIONS

Panka et al., Variable region framework differences result in decreased or increased affinity of variant anti-digoxin antibodies, 1988, PNAS, vol. 85, pp. 3080-3084.*

Gonzales et al., Minimizing immunogenicity of the SDR-grafted humanized antibody CC49 by genetic manipulation of the framework residues, 2003, Molecular Immunology, vol. 40, pp. 337-349.*

Brinkmann and Kontermann, "The making of bispecific antibodies," InMAbs, 9(2):182-212, Feb. 2017.

Buchholz et Al., "Contributions of the structural proteins of severe acute respiratory syndrome coronavirus to protective immunity," Proceedings of the National Academy of Sciences, 101(26):9804-9, Jun. 2004.

Chen et al., "Fusion protein linkers: property, design and functionality," Adv. Drug Deliv. Rev., 65(10):1357-1369, 2013.

Fisher et al., "A novel adenovirus-adeno-associated virus hybrid vector that displays efficient rescue and delivery of the AAV genome," Human gene therapy, 7(17):2079-87, Nov. 1996.

Frenzel et al., "Expression of recombinant antibodies," Frontiers in immunology, 4:217, Jul. 2013.

Gervasi et al., "Parenteral protein formulations: An overview of approved products within the European Union," European Journal of Pharmaceutics and Biopharmaceutics, 131:8-24, Oct. 2018.

Hornig and Färber-Schwarz, "Production of Bispecific Antibodies: Diabodies and Tandem scFv," Methods Mol. Biol., 907:713-27, 2012.

Hui et al., "The continuing 2019-nCoV epidemic threat of novel coronaviruses to global health—The latest 2019 novel coronavirus outbreak in Wuhan, China," International Journal of Infectious Diseases, 91:264-6, Feb. 2020.

Hui et al., "The continuing epidemic threat of novel coronaviruses to global health—the latest novel coronavirus outbreak in Wuhan, China," International Journal of Infectious Diseases, doi:10.1016/j.ijid.2020.01.009, 1920.

Li et al., "Angiotensin-converting enzyme 2 is a functional receptor for the SARS coronavirus," Nature, 426(6965):450-4, Nov. 2003.

Li et al., "Rapid selection of a human monoclonal antibody that potently neutralizes SARS-CoV-2 in two animal models," bioRxiv, Jan. 2020, 41 pages.

Neumann et al., "Gene transfer into mouse lyoma cells by electroporation in high electric fields," The EMBO journal, 1(7):841-5, Jul. 1982.

Prabakaran et al., "Structure of severe acute respiratory syndrome coronavirus receptor-binding domain complexed with neutralizing antibody," Journal of Biological Chemistry, 281(23):15829-36, Jun. 2006.

(Continued)

*Primary Examiner* — Benjamin P Blumel
(74) *Attorney, Agent, or Firm* — Fish & Richardson P.C.

(57) ABSTRACT

This document provides methods and materials involved in binding a binder (e.g., an antibody, antigen binding fragment, and/or antibody domain) to a SARS-CoV-2 antigen. For example, binders (e.g., antibodies, antigen binding fragments, and antibody domains) that bind to a SARS-CoV-2 polypeptide and methods and materials for using one or more such binding molecules to treat a mammal (e.g., a human) having COVID-19 (or a viral infection caused by SARS-CoV-2) are provided.

18 Claims, 20 Drawing Sheets

Specification includes a Sequence Listing.

(56) References Cited

OTHER PUBLICATIONS

Sun et al., "Potent neutralization of SARS-CoV-2 by human antibody heavy-chain variable domains isolated from a large library with a new stable scaffold," InMabs, 12(1):1-6, Jan. 2020.
Walls et al., "Unexpected receptor functional mimicry elucidates activation of coronavirus fusion," Cell, 176(5):1026-39, Feb. 2019.
Zheng et al., "Genomic integration and gene expression by a modified adenoviral vector," Nature biotechnology, 18(2):176-80, Feb. 2000.
Zoller, "New recombinant DNA methodology for protein engineering," Current opinion in biotechnology, 3(4):348-54, Aug. 1992.

* cited by examiner

Figure 1

MFVFLVLLPLVSSQCVNLTTRTQLPPAYTNSFTRGVYYPDKVFRSSVLHSTQDLFLPFFS
NVTWFHAIHVSGTNGTKRFDNPVLPFNDGVYFASTEKSNIIRGWIFGTTLDSKTQSLLIV
NNATNVVIKVCEFQFCNDPFLGVYYHKNNKSWMESEFRVYSSANNCTFEYVSQPFLMD
LEGKQGNFKNLREFVFKNIDGYFKIYSKHTPINLVRDLPQGFSALEPLVDLPIGINITRFQT
LLALHRSYLTPGDSSSGWTAGAAAYYVGYLQPRTFLLKYNENGTITDAVDCALDPLSET
KCTLKSFTVEKGIYQTSNFRVQPTESIVRFPNITNLCPFGEVFNATRFASVYAWNRKRI
SNCVADYSVLYNSASFSTFKCYGVSPTKLNDLCFTNVYADSFVIRGDEVRQIAPGQT
GKIADYNYKLPDDFTGCVIAWNSNNLDSKVGGNYNYLYRLFRKSNLKPFERDISTEI
YQAGSTPCNGVEGFNCYFPLQSYGFQPTNGVGYQPYRVVVLSFELLHAPATVCGP
KKSTNLVKNKCVNFNFNGLTGTGVLTESNKKFLPFQQFGRDIADTTDAVRDPQTLEILD
ITPCSFGGVSVITPGTNTSNQVAVLYQDVNCTEVPVAIHADQLTPTWRVYSTGSNVFQT
RAGCLIGAEHVNNSYECDIPIGAGICASYQTQTNSPRRARSVASQSIIAYTMSLGAENSVA
YSNNSIAIPTNFTISVTTEILPVSMTKTSVDCTMYICGDSTECSNLLLQYGSFCTQLNRALT
GIAVEQDKNTQEVFAQVKQIYKTPPIKDFGGFNFSQILPDPSKPSKRSFIEDLLFNKVTLA
DAGFIKQYGDCLGDIAARDLICAQKFNGLTVLPPLLTDEMIAQYTSALLAGTITSGWTFG
AGAALQIPFAMQMAYRFNGIGVTQNVLYENQKLIANQFNSAIGKIQDSLSSTASALGKL
QDVVNQNAQALNTLVKQLSSNFGAISSVLNDILSRLDKVEAEVQIDRLITGRLQSLQTYV
TQQLIRAAEIRASANLAATKMSECVLGQSKRVDFCGKGYHLMSFPQSAPHGVVFLHVT
YVPAQEKNFTTAPAICHDGKAHFPREGVFVSNGTHWFVTQRNFYEPQIITTDNTFVSGN
CDVVIGIVNNTVYDPLQPELDSFKEELDKYFKNHTSPDVDLGDISGINASVVNIQKEIDRL
NEVAKNLNESLIDLQELGKYEQYIKWPWYIWLGFIAGLIAIVMVTIMLCCMTSCCSCLK
GCCSCGSCCKFDEDDSE PVLKGVKLHYT

Figure 2A

Anti-SARS-CoV-2 RBD Clone #1 (Fab)

Heavy chain variable domain (with first constant domain):

EVQLVESGGGLVQPGGSLRLSCAASGFTVSSNYMSWVRQAPGKGLEWVSVIYSGGSTYYADSVKGRFTISRHNSKNTLYLQMNSLRAEDTAVYYCARGYGDYYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC (SEQ ID NO:8)

Framework Region 1 of heavy chain variable domain:

EVQLVESGGGLVQPGGSLRLSCAASGFTVS (SEQ ID NO:4)

CDR1 of heavy chain variable domain:

SNYMS (SEQ ID NO:1)

Framework Region 2 of heavy chain variable domain:

WVRQAPGKGLEWVS (SEQ ID NO:5)

CDR2 of heavy chain variable domain:

VIYSGGSTYYADSVKG (SEQ ID NO:2)

Framework Region 3 of heavy chain variable domain:

RFTISRHNSKNTLYLQMNSLRAEDTAVYYCAR (SEQ ID NO:6)

CDR3 of heavy chain variable domain:

GYGDYYFDY (SEQ ID NO:3)

Framework Region 4 of heavy chain variable domain:

WGQGTLVTVSS (SEQ ID NO:7)

Heavy chain constant domain 1 (CH1):
    ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC (SEQ ID NO:497)

Figure 2B

Anti-SARS-CoV-2 RBD Clone #1 (Fab)

Light chain variable domain (with kappa constant domain):

DVVMTQSPATLSLSPGEKATLSCRASQSVSSYLAWYQQKPGQPPKLLIYWASTRESGV
PDRFSGSGSGTDFTLTISSLQAEDVAVYYCQQYGSSPLTFGGGTKVEIKRTVAAPSVFIF
PPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:16)

Framework Region 1 of light chain variable domain:

DVVMTQSPATLSLSPGEKATLSC (SEQ ID NO:12)

CDR1 of light chain variable domain:

RASQSVSSYLA (SEQ ID NO:9)

Framework Region 2 of light chain variable domain:

WYQQKPGQPPKLLIY (SEQ ID NO:13)

CDR2 of light chain variable domain:

WASTRES (SEQ ID NO:10)

Framework Region 3 of light chain variable domain:

GVPDRFSGSGSGTDFTLTISSLQAEDVAVYYC (SEQ ID NO:14)

CDR3 of light chain variable domain:

QQYGSSPLT (SEQ ID NO:11)

Framework Region 4 of light chain variable domain:

FGGGTKVEIK (SEQ ID NO:15)

Kappa light chain constant domain:

RTVAAPSVFIFPPSDEQLKSGTASVVCLLNNFYPREAKVQWKVDNALQSGNSQE
    SVTEQDSKDSTYSLSSTLTLSKADYEKHKVYACEVTHQGLSSPVTKSFNRGEC
    (SEQ ID NO:498)

Figure 3A

Anti-SARS-CoV-2 RBD Clone #2 (Fab)

Heavy chain variable domain (with first constant domain):

QVQLQQSGPGLVKPSQTLSLTCAISGDSVSSNSAAWNWIRQSPSRGLEWLGRTYYRSKWYNDYAVSVKSRITINPDTSKNQFSLQLNSVTPEDTAVYYCAREQQQLVPHYYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTS (SEQ ID NO:24)

Framework Region 1 of heavy chain variable domain:

QVQLQQSGPGLVKPSQTLSLTCAISGDSVS (SEQ ID NO:20)

CDR1 of heavy chain variable domain:

SNSAAWN (SEQ ID NO:17)

Framework Region 2 of heavy chain variable domain:

WIRQSPSRGLEWLG (SEQ ID NO:21)

CDR2 of Heavy chain variable domain:

RTYYRSKWYNDYAVSVKS (SEQ ID NO:18)

Framework Region 3 of heavy chain variable domain:

RITINPDTSKNQFSLQLNSVTPEDTAVYYCAR (SEQ ID NO:22)

CDR3 of heavy chain variable domain:

EQQQLVPHYYYYGMDV (SEQ ID NO:19)

Framework Region 4 of heavy chain variable domain:

WGQGTTVTVSS (SEQ ID NO:23)

Heavy chain constant domain 1 (CH1):

ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTS (SEQ ID NO:499)

Figure 3B

Anti-SARS-CoV-2 RBD Clone #2 (Fab)

Light chain variable domain (with lambda constant domain):

DVVMTQSPSVSGSPGQSVTISCTGTTSDVGGYNYVSWYQQRPGKAPKLMIYEVSKRPSGVPDRFSGSKSGNTASLTVSGLQAEDEADYYCSSYTSSSTLFGTGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS (SEQ ID NO:32)

Framework Region 1 of light chain variable domain:

DVVMTQSPSVSGSPGQSVTISC (SEQ ID NO:28)

CDR1 of light chain variable domain:

TGTTSDVGGYNYVS (SEQ ID NO:25)

Framework Region 2 of light chain variable domain:

WYQQRPGKAPKLMIY (SEQ ID NO:29)

CDR2 of light chain variable domain:

EVSKRPS (SEQ ID NO:26)

Framework Region 3 of light chain variable domain:

GVPDRFSGSKSGNTASLTVSGLQAEDEADYYC (SEQ ID NO:30)

CDR3 of light chain variable domain:

SSYTSSSTL (SEQ ID NO:27)

Framework Region 4 of light chain variable domain:

FGTGTKLTVLG (SEQ ID NO:31)

Lambda light chain constant domain:

QPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS (SEQ ID NO:500)

Figure 4A

Anti-SARS-CoV-2 RBD Clone #3 (scFv)

Variable Heavy Region:

EVQLVQSGGGLVQPGGSLRLSCSASGFTFSSYAMHWVRQAPGKGLEYVSAISTDGGSTYYADSVKGRFTISRDNSKNTLYLQMNSLRAEDTAVYYCAKTYYDFWRTYYGMDVWGQGTMVTVSS (SEQ ID NO:40)

Framework Region 1 of Variable Heavy Region:

EVQLVQSGGGLVQPGGSLRLSCSAS (SEQ ID NO:36)

CDR1 of Variable Heavy Region:

GFTFSSYA (SEQ ID NO:33)

Framework Region 2 of Variable Heavy Region:

MHWVRQAPGKGLEYVSA (SEQ ID NO:37)

CDR2 of Variable Heavy Region:

ISTDGGST (SEQ ID NO:34)

Framework Region 3 of Variable Heavy Region:

YYADSVKGRFTISRDNSKNTLYLQMNSLRAEDTAVYYC (SEQ ID NO:38)

CDR3 of Variable Heavy Region:

AKTYYDFWRTYYGMDV (SEQ ID NO:35)

Framework Region 4 of Variable Heavy Region:

WGQGTMVTVSS (SEQ ID NO:39)

Figure 4B

Anti-SARS-CoV-2 RBD Clone #3 (scFv)

Variable Light Region:

EATLTQSPSSLSASVGDRVTITCRASQSISSYLNWYQQKPGRAPKLLIYAASSLQSGVPSR
FSGSGSGTDFTLTISSLQPEDFATYYCQQSYSTPYTFGQGTRLEIKR (SEQ ID NO:48)

Framework Region 1 of Variable Light Region:

EATLTQSPSSLSASVGDRVTITCRAS (SEQ ID NO:44)

CDR1 of Variable Light Region:

QSISSY (SEQ ID NO:41)

Framework Region 2 of Variable Light Region:

LNWYQQKPGRAPKLLIY (SEQ ID NO:45)

CDR2 of Variable Light Region:

AAS (SEQ ID NO:42)

Framework Region 3 of Variable Light Region:

SLQSGVPSRFSGSGSGTDFTLTISSLQPEDFATYYC (SEQ ID NO:46)

CDR3 of Variable Light Region:

QQSYSTPYT (SEQ ID NO:43)

Framework Region 4 of Variable Light Region:

FGQGTRLEIKR (SEQ ID NO:47)

Figure 4C

Exemplary Linker Sequences for scFv's:

a)   GGGGSGGSGSGGGGS (SEQ ID NO:516; Linker used for Clone #3)

b)   GGGGSGGSGSSGGGS (SEQ ID NO:517; Linker used for Clone #4)

c)   GGGGSGGGGSGGGGS (SEQ ID NO:518)

d)   GGGGSGSGASSGGGS (SEQ ID NO:519)

e)   GGGGSGSGASGGGGS (SEQ ID NO:520)

f)   SGGGSGGGGSGGGGS (SEQ ID NO:521)

g)   GSTSGSGKPGSGEGSTKG (SEQ ID NO:522)

h)   PNGASQSSSASHTGSAPGS (SEQ ID NO:523)

i)   PNGASNSGSAPDTSSAPGS (SEQ ID NO:524)

j)   PNGASHSGSAPNTSSAPGS (SEQ ID NO:525)

k)   PNGASESGSASKTSSASGS (SEQ ID NO:526)

l)   PNGASNSGSAPKTGSASGS (SEQ ID NO:527)

m)   PNGASKSGSASQTSSAPGS (SEQ ID NO:528)

n)   PNGASHSSSASQTGSAPGS (SEQ ID NO:529)

o)   PNGASKRSAPGS (SEQ ID NO:530)

p)   PNGASHSGSAPHTSSASGS (SEQ ID NO:531)

q)   RGRGRGRGRSRGGGS (SEQ ID NO:532)

r)   SHGGSHGGGSGGGGS (SEQ ID NO:533)

Figure 5A

Anti-SARS-CoV-2 RBD Clone #4 (scFv)

Variable Heavy Region:

EVQLVQSGGGLVQPGGSLRLSCAASGFTFSNYAMTWVRQAPGKGLEWVSTIAGSGDN TYYADSVKGRFTISRDNDKNTLYLQMNSLRADDTAVYYCARDRYYTMDVWGQGTLV TVSS (SEQ ID NO:56)

Framework Region 1 of Variable Heavy Region:

EVQLVQSGGGLVQPGGSLRLSCAAS (SEQ ID NO:52)

CDR1 of Variable Heavy Region:

GFTFSNYA (SEQ ID NO:49)

Framework Region 2 of Variable Heavy Region:

MTWVRQAPGKGLEWVST (SEQ ID NO:53)

CDR2 of Variable Heavy Region:

IAGSGDNT (SEQ ID NO:50)

Framework Region 3 of Variable Heavy Region:

YYADSVKGRFTISRDNDKNTLYLQMNSLRADDTAVYYC (SEQ ID NO:54)

CDR3 of Variable Heavy Region:

ARDRYYTMDV (SEQ ID NO:51)

Framework Region 4 of Variable Heavy Region:

WGQGTLVTVSS (SEQ ID NO:55)

Figure 5B

Anti-SARS-CoV-2 RBD Clone #4 (scFv)

Variable Light Region:

QSVVTQPPSASGSPGQSVTISCTGTSSDVGGYNHVSWYQQHPGKAPKLLIYEVSERPSG
VPDRFSGSKSDNKASLTIIGLQTEDEADYYCQSYDSSLSGSLFGTGTKLTVLR (SEQ ID
NO:64)

Framework Region 1 of Variable Light Region:

QSVVTQPPSASGSPGQSVTISCTGT (SEQ ID NO:60)

CDR1 of Variable Light Region:

SSDVGGYNH (SEQ ID NO:57)

Framework Region 2 of Variable Light Region:

VSWYQQHPGKAPKLLIY (SEQ ID NO:61)

CDR2 of Variable Light Region:

EVS (SEQ ID NO:58)

Framework Region 3 of Variable Light Region:

ERPSGVPDRFSGSKSDNKASLTIIGLQTEDEADYYC (SEQ ID NO:62)

CDR3 of Variable Light Region:

QSYDSSLSGSL (SEQ ID NO:59)

Framework Region 4 of Variable Light Region:

FGTGTKLTVLR (SEQ ID NO:63)

Figure 6

Anti-SARS-CoV-2 RBD Clone #5 (VH Domain)

KVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCVRLPMIKKSFDIWGPGTLVTVSS (SEQ ID NO:72)

Framework Region 1 of VH Domain:

KVQLQQWGAGLLKPSETLSLTCAVY (SEQ ID NO:68)

CDR1 of VH Domain:

GGSFSGYY (SEQ ID NO:65)

Framework Region 2 of VH Domain:

WSWIRQPPGKGLEWIGE (SEQ ID NO:69)

CDR2 of VH Domain:

INHSGST (SEQ ID NO:66)

Framework Region 3 of VH Domain:

NYNPSLKSRVTISVDTSKNQFSLKLSSVTAADTAVY (SEQ ID NO:70)

CDR3 of VH Domain:

YCVRLPMIKKSFDI (SEQ ID NO:67)

Framework Region 4 of VH Domain:

WGPGTLVTVSS (SEQ ID NO:71)

Figure 7

Anti-SARS-CoV-2 RBD Clone #6 (VH Domain)

EVQLVESGGGVVQPGRSLRLSCAASGFTFSSYAMHWVRQAPGKGLEWIGNIYHDGSTFYNPSLKSLVTISRDDSTNTLYLQMNSLRAEDTAIYYCARVWLYGSGYMDVWGKGTLVTVSS (SEQ ID NO:80)

Framework Region 1 of VH Domain:

EVQLVESGGGVVQPGRSLRLSCAAS (SEQ ID NO:76)

CDR1 of VH Domain:

GFTFSSYA (SEQ ID NO:73)

Framework Region 2 of VH Domain:

MHWVRQAPGKGLEWIGN (SEQ ID NO:77)

CDR2 of VH Domain:

IYHDGST (SEQ ID NO:74)

Framework Region 3 of VH Domain:

FYNPSLKSLVTISRDDSTNTLYLQMNSLRAEDTAIYYC (SEQ ID NO:78)

CDR3 of VH Domain:

ARVWLYGSGYMDV (SEQ ID NO:75)

Framework Region 4 of VH Domain:

WGKGTLVTVSS (SEQ ID NO:79)

Figure 8

Anti-SARS-CoV-2 RBD Clone #7 (VH Domain)

EVQLVESGGGLVQPGGSLRLSCAASAFDFYDYEMSWVRQAPGKALEWIGEIHHSGSTYYNPSLKGRFTISRDNSKNTLYLQMNSLRAEDTAVYYCAKDVSYHADVWGQGTTVTVSS (SEQ ID NO:88)

Framework Region 1 of VH Domain:

EVQLVESGGGLVQPGGSLRLSCAASAFDFY (SEQ ID NO:84)

CDR1 of VH Domain:

DYEMS (SEQ ID NO:81)

Framework Region 2 of VH Domain:

WVRQAPGKALEWIG (SEQ ID NO:85)

CDR2 of VH Domain:

EIHHSGSTYYNPSLKG (SEQ ID NO:82)

Framework Region 3 of VH Domain:

RFTISRDNSKNTLYLQMNSLRAEDTAVYYCAK (SEQ ID NO:86)

CDR3 of VH Domain:

DVSYHADV (SEQ ID NO:83)

Framework Region 4 of VH Domain:

WGQGTTVTVSS (SEQ ID NO:87)

Figure 9

Anti-SARS-CoV-2 RBD Clone #8 (VH Domain)

EVQLVESGGGLVQPGGSLRLSCAASGFTFDDYAMSWVRQAPGKGLEWIGRMYNNGRTSYNPSLKSLVTISRDNSKNTLYLQMNSLRAEDTATYYCARDNLGYRPSENLYGMDVWGQGTTVTVSS (SEQ ID NO:96)

Framework Region 1 of VH Domain:

EVQLVESGGGLVQPGGSLRLSCAASGFTFD (SEQ ID NO:92)

CDR1 of VH Domain:

DYAMS (SEQ ID NO:89)

Framework Region 2 of VH Domain:

WVRQAPGKGLEWIG (SEQ ID NO:93)

CDR2 of VH Domain:

RMYNNGRTSYNPSLKS (SEQ ID NO:90)

Framework Region 3 of VH Domain:

LVTISRDNSKNTLYLQMNSLRAEDTATYYCAR (SEQ ID NO:94)

CDR3 of VH Domain:

DNLGYRPSENLYGMDV (SEQ ID NO:91)

Framework Region 4 of VH Domain:

WGQGTTVTVSS (SEQ ID NO:95)

Figure 10

Anti-SARS-CoV-2 RBD Clone #9 (VH Domain)

EVQLVESGGGLVQPGGSLRLSCKGSGFTLSDYYIGWVRQAPGKGLEWIGSMYHSGRTYINPSLKSRVTISRDNSKNTLYLQMNSLRAEDTAVYYCARGGITGTTPIDYWGQGTLVTVSS (SEQ ID NO:104)

Framework Region 1 of VH Domain:

EVQLVESGGGLVQPGGSLRLSCKGSGFTLS (SEQ ID NO:100)

CDR1 of VH Domain:

DYYIG (SEQ ID NO:97)

Framework Region 2 of VH Domain:

WVRQAPGKGLEWIG (SEQ ID NO:101)

CDR2 of VH Domain:

SMYHSGRTYINPSLKS (SEQ ID NO:98)

Framework Region 3 of VH Domain:

RVTISRDNSKNTLYLQMNSLRAEDTAVYYCAR (SEQ ID NO:102)

CDR3 of VH Domain:

GGITGTTPIDY (SEQ ID NO:99)

Framework Region 4 of VH Domain:

WGQGTLVTVSS (SEQ ID NO:103)

Figure 11

Clone #1

Nucleic acid encoding SEQ ID NO:8 (Clone #1; Heavy Chain):

GAGGTGCAGCTGGTGGAGTCTGGAGGAGGCTTGGTCCAGCCTGGGGGGTCCCTGAG
ACTCTCCTGTGCAGCCTCTGGGTTCACCGTCAGTAGCAACTACATGAGCTGGGTCCG
CCAGGCTCCAGGGAAGGGGCTGGAGTGGGTCTCAGTTATTTATAGCGGTGGTAGCA
CATACTACGCAGACTCCGTGAAGGGCCGATTCACCATCTCCAGACACAATTCCAAG
AACACGCTGTATCTTCAAATGAACAGCCTGAGAGCTGAGGACACGGCCGTGTATTA
CTGTGCGAGGGGGTACGGTGACTACTACTTTGACTACTGGGGCCAGGGAACCCTGGT
CACCGTCTCCTCAGCCTCCACCAAGGGCCCATCGGTCTTCCCCCTGGCACCCTCCTCC
AAGAGCACCTCTGGGGGCACAGCGGCCCTGGGCTGCCTGGTCAAGGACTACTTCCC
CGAACCGGTGACGGTGTCGTGGAACTCAGGCGCCCTGACCAGCGGCGTGCACACCT
TCCCGGCTGTCCTACAGTCCTCAGGACTCTACTCCCTCAGCAGCGTGGTGACCGTGC
CCTCCAGCAGCTTGGGCACCCAGACCTACATCTGCAACGTGAATCACAAGCCCAGC
AACACCAAGGTGGACAAGAAAGTTGAGCCCAAATCTTGT (SEQ ID NO:501)

Nucleic acid encoding SEQ ID NO:16 (Clone #1; Light Chain):

GATGTTGTGATGACTCAGTCTCCAGCCACCCTGTCTTTGTCTCCAGGGGAAAAAGCC
ACCCTCTCCTGCAGGGCCAGTCAGAGTGTTAGCAGCTACTTAGCCTGGTACCAGCAG
AAACCAGGACAGCCTCCTAAGCTGCTCATTTACTGGGCATCTACCCGGGAATCCGGG
GTCCCTGACCGATTCAGTGGCAGCGGGTCTGGGACAGATTTCACTCTCACCATCAGC
AGCCTGCAGGCTGAAGATGTGGCAGTTTATTACTGTCAGCAGTATGGTAGCTCACCT
CTCACTTTCGGCGGAGGGACCAAGGTGGAGATCAAACGAACTGTGGCTGCACCATC
TGTCTTCATCTTCCCGCCATCTGATGAGCAGTTGAAATCTGGAACTGCCTCTGTTGTG
TGCCTGCTGAATAACTTCTATCCCAGAGAGGCCAAAGTACAGTGGAAGGTGGATAA
CGCCCTCCAATCGGGTAACTCCCAGGAGAGTGTCACAGAGCAGGACAGCAAGGACA
GCACCTACAGCCTCAGCAGCACCCTGACGCTGAGCAAAGCAGACTACGAGAAACAC
AAAGTCTACGCCTGCGAAGTCACCCATCAGGGCCTGAGCTCGCCCGTCACAAAGAG
CTTCAACAGGGGAGAGTGT (SEQ ID NO:502)

Clone #2

Nucleic acid encoding SEQ ID NO:24 (Clone #2; Heavy Chain):

CAGGTACAGCTGCAGCAGTCAGGTCCAGGACTGGTGAAGCCCTCGCAGACCCTCTC
ACTCACCTGTGCCATCTCCGGGGACAGTGTCTCTAGCAACAGTGCTGCTTGGAACTG
GATCAGGCAGTCCCCATCGAGAGGCCTTGAGTGGCTGGGAAGGACATACTACAGGT
CCAAGTGGTATAATGATTATGCAGTATCTGTGAAAAGTCGAATAACCATCAACCCAG
ACACATCCAAGAACCAGTTCTCCCTGCAGCTGAACTCTGTGACTCCCGAGGACACGG
CTGTGTATTACTGTGCAAGAGAGCAGCAGCAGCTGGTACCGCACTACTACTACTACG

Figure 11 (continued)

GTATGGACGTCTGGGGCCAAGGGACCACGGTCACCGTCTCCTCAGCCTCCACCAAG
GGCCCATCGGTCTTCCCCCTGGCACCCTCCTCCAAGAGCACCTCTGGGGGCACAGCG
GCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAAAGTTGA
GCCCAAATCTTGT (SEQ ID NO:503)

Nucleic acid encoding SEQ ID NO:32 (Clone #2; Light Chain):

GATGTTGTGATGACTCAGTCTCCCTCCGTGTCCGGGTCTCCTGGACAGTCAGTCACC
ATCTCCTGCACTGGAACCACCAGTGACGTTGGTGGCTATAACTATGTCTCCTGGTAC
CAACAGCGCCCAGGCAAAGCCCCCAAACTCATGATTTATGAGGTCAGTAAGCGGCC
CTCAGGGGTCCCTGATCGCTTCTCTGGCTCCAAGTCTGGCAACACGGCCTCCCTGAC
CGTCTCTGGGCTCCAGGCTGAGGACGAGGCTGATTATTACTGCAGCTCATATACAAG
CAGCAGCACTCTCTTCGGAACTGGGACCAAGCTGACCGTCCTAGGTCAGCCCAAGG
CTGCCCCCTCGGTCACTCTGTTCCCGCCCTCCTCTGAGGAGCTTCAAGCCAACAAGG
CCACACTGGTGTGTCTCATAAGTGACTTCTACCCGGGAGCCGTGACAGTGGCCTGGA
AGGCAGATAGCAGCCCCGTCAAGGCGGGAGTGGAGACCACCACACCCTCCAAACAA
AGCAACAACAAGTACGCGGCCAGCAGCTATCTGAGCCTGACGCCTGAGCAGTGGAA
GTCCCACAGAAGCTACAGCTGCCAGGTCACGCATGAAGGGAGCACCGTGGAGAAGA
CAGTGGCCCCTACAGAATGTTCA (SEQ ID NO:504)

Clone #3

Nucleic acid encoding SEQ ID NO:40 (Clone #3; Heavy Region):

GAGGTCCAGCTGGTGCAGTCTGGGGGGGGCTTGGTCCAGCCTGGGGGGTCCCTGAG
ACTCTCCTGTTCAGCCTCTGGATTCACCTTCAGTAGCTATGCTATGCACTGGGTCCGC
CAGGCTCCAGGGAAGGGACTGGAATATGTTTCAGCTATTAGTACTGATGGGGGTAG
CACATACTACGCAGACTCCGTGAAGGGCAGATTCACCATCTCCAGAGACAATTCCA
AGAACACGCTGTATCTGCAAATGAACAGCCTGAGAGCTGAGGACACGGCTGTGTAT
TACTGTGCGAAAACGTATTACGATTTTTGGAGGACCTACTACGGTATGGACGTCTGG
GGCCAAGGGACAATGGTCACCGTCTCTTCA (SEQ ID NO:505)

Nucleic acid encoding SEQ ID NO:516 (Clone #3; Linker):

GGAGGTGGCGGGTCTGGTGGTAGCGGAAGCGGTGGTGGCGGATCC (SEQ ID NO:506)

Figure 11 (continued)

Nucleic acid encoding SEQ ID NO:48 (Clone #3; Light Region):

GAAGCGACACTCACGCAGTCTCCATCCTCCCTGTCTGCATCTGTAGGAGACAGAGTC
ACCATCACTTGCCGGGCAAGTCAGAGCATTAGCAGCTATTTAAATTGGTATCAGCAG
AAACCAGGGAGAGCCCCTAAGCTCCTGATCTATGCTGCATCCAGTTTGCAAAGTGGG
GTCCCATCACGGTTCAGTGGCAGTGGATCTGGGACAGATTTCACTCTCACCATCAGC
AGTCTGCAACCTGAAGATTTTGCAACTTACTACTGTCAACAGAGTTACAGTACCCCG
TACACTTTTGGCCAGGGGACACGACTGGAGATTAAACGT (SEQ ID NO:507)

Clone #4

Nucleic acid encoding SEQ ID NO:56 (Clone #4; Heavy Region):

GAGGTCCAGCTGGTACAGTCTGGGGGGGGCTTGGTACAGCCTGGGGGGTCCCTGAG
ACTCTCCTGTGCAGCCTCTGGATTCACTTTTAGCAACTATGCCATGACCTGGGTCCGC
CAGGCTCCGGGGAAGGGGCTAGAGTGGGTCTCAACTATTGCTGGTAGTGGTGACAA
CACATACTACGCAGACTCCGTGAAGGGCCGATTCACCATCTCCAGAGACAATGACA
AGAACACACTGTATCTGCAAATGAACAGTCTGAGAGCCGACGACACGGCTGTTTATT
ACTGTGCAAGAGACCGGTACTACACTATGGACGTCTGGGGCCAAGGCACCCTGGTC
ACCGTCTCCTCA (SEQ ID NO:508)

Nucleic acid encoding SEQ ID NO:517 (Clone #4; Linker):

GGAGGTGGCGGGTCTGGTGGTAGCGGAAGCAGTGGTGGCGGATCC (SEQ ID NO:509)

Nucleic acid encoding SEQ ID NO:64 (Clone #4; Light Region):

CAGTCTGTCGTGACGCAGCCGCCCTCCGCGTCCGGGTCTCCTGGACAGTCAGTCACC
ATCTCCTGCACTGGAACCAGCAGTGACGTTGGTGGTTATAACCATGTCTCCTGGTAC
CAACAGCACCCAGGCAAGGCCCCCAAACTCTTGATTTATGAGGTCAGTGAGCGGCC
CTCAGGGGTCCCTGATCGCTTCTCTGGCTCCAAGTCTGACAACAAGGCCTCCCTGAC
CATCATTGGGCTCCAGACTGAAGATGAGGCTGATTATTATTGCCAGTCCTATGACAG
CAGCCTGAGTGGTTCCCTCTTCGGAACCGGGACCAAGCTGACCGTCCTACGT (SEQ ID NO:510)

Figure 11 (continued)

Clone #5

Nucleic acid encoding SEQ ID NO:72 (Clone #5; VH Domain):

AAGGTGCAGCTACAGCAGTGGGGCGCAGGACTGTTGAAGCCTTCGGAGACCCTGTC
CCTCACCTGCGCTGTCTATGGTGGGTCCTTCAGTGGTTACTACTGGAGCTGGATCCG
CCAGCCCCCAGGGAAGGGGCTGGAGTGGATTGGGGAAATCAATCATAGTGGAAGCA
CCAACTACAACCCGTCCCTCAAGAGTCGAGTCACCATATCAGTAGACACGTCCAAG
AACCAGTTCTCCCTGAAGCTGAGCTCTGTGACCGCCGCGGACACGGCCGTGTATTAC
TGTGTTAGACTCCCCATGATTAAGAAGTCATTTGATATTTGGGGCCCAGGCACCCTG
GTCACCGTCTCCTCAG (SEQ ID NO:511)

Clone #6

Nucleic acid encoding SEQ ID NO:80 (Clone #6; VH Domain):

GAGGTGCAGCTGGTGGAGTCCGGGGGAGGCGTGGTCCAGCCTGGGAGGTCCCTGAG
ACTCTCCTGTGCAGCCTCTGGATTCACCTTCAGTAGCTATGCTATGCACTGGGTCCGC
CAGGCTCCAGGGAAGGGTCTAGAGTGGATTGGAAATATCTATCATGATGGGAGCAC
CTTCTACAACCCGTCCCTCAAGAGTCTAGTCACCATCTCCAGAGACGATTCCACGAA
CACGCTGTATCTGCAAATGAACAGCCTGAGAGCCGAGGACACAGCCATATATTACT
GTGCCAGAGTTTGGCTTTATGGTTCAGGCTACATGGACGTCTGGGGCAAAGGCACCC
TGGTCACCGTCTCCTCAG (SEQ ID NO:512)

Clone #7

Nucleic acid encoding SEQ ID NO:88 (Clone #7; VH Domain):

GAGGTGCAGCTGGTGGAGTCTGGGGGAGGCTTGGTACAGCCTGGAGGGTCCCTGAG
ACTCTCCTGTGCAGCCTCTGCTTTCGATTTCTATGATTATGAAATGAGCTGGGTCCGC
CAGGCTCCAGGGAAGGCCCTGGAGTGGATTGGGGAAATCCATCATAGTGGGAGCAC
CTACTACAACCCGTCCCTCAAGGGCCGATTCACCATCTCCAGAGACAATTCCAAGAA
CACGCTGTATCTGCAAATGAACAGCCTGAGAGCCGAGGACACGGCCGTGTATTACT
GTGCCAAGGACGTCAGCTATCACGCGGACGTCTGGGGCCAAGGGACCACGGTCACC
GTCTCCTCA (SEQ ID NO:513)

Figure 11 (continued)

Clone #8

Nucleic acid encoding SEQ ID NO:96 (Clone #8; VH Domain):

GAGGTGCAGCTGGTGGAGTCTGGGGGAGGCTTGGTACAGCCTGGAGGGTCCCTGAG
ACTCTCCTGTGCAGCCTCTGGATTCACCTTTGATGATTATGCCATGAGCTGGGTCCGC
CAGGCTCCAGGGAAGGGCCTAGAGTGGATTGGGCGTATGTATAACAATGGGAGGAC
CAGCTACAACCCCTCCCTCAAGAGTCTAGTCACCATCTCCAGAGACAATTCCAAGAA
CACGCTGTATCTGCAAATGAACAGCCTGAGAGCCGAGGACACAGCCACATATTACT
GTGCGAGAGACAATCTGGGCTATAGACCTTCAGAAAACCTCTATGGTATGGACGTCT
GGGGCCAAGGGACCACGGTCACCGTCTCCTCA (SEQ ID NO:514)

Clone #9

Nucleic acid encoding SEQ ID NO:104 (Clone #9; VH Domain):

GAGGTGCAGCTGGTGGAGTCTGGGGGAGGCTTGGTACAGCCTGGAGGGTCCCTGAG
ACTCTCCTGTAAGGGTTCTGGATTCACCTTAAGTGACTACTACATCGGCTGGGTCCG
CCAGGCTCCAGGGAAGGGTCTAGAGTGGATTGGGAGTATGTATCATAGTGGGCGCA
CCTACATCAACCCGTCCCTCAAGAGTCGAGTCACCATCTCCAGAGACAATTCCAAGA
ACACGCTGTATCTGCAAATGAACAGCCTGAGAGCCGAGGACACAGCCGTGTATTAC
TGTGCGAGAGGCGGTATAACTGGAACGACGCCTATTGACTACTGGGGCCAGGGAAC
CCTGGTCACCGTCTCCTCA (SEQ ID NO:515)

```
                          SEQUENCE LISTING

<160> NUMBER OF SEQ ID NOS: 533

<210> SEQ ID NO 1
<211> LENGTH: 5
<212> TYPE: PRT
<213> ORGANISM: Artificial
<220> FEATURE:
<223> OTHER INFORMATION: complementary determining region of an antigen
      binder

<400> SEQUENCE: 1

Ser Asn Tyr Met Ser
1               5

<210> SEQ ID NO 2
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 2

Val Ile Tyr Ser Gly Gly Ser Thr Tyr Tyr Ala Asp Ser Val Lys Gly
1               5                   10                  15

<210> SEQ ID NO 3
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 3

Gly Tyr Gly Asp Tyr Tyr Phe Asp Tyr
1               5

<210> SEQ ID NO 4
<211> LENGTH: 30
<212> TYPE: PRT
<213> ORGANISM: Artificial
<220> FEATURE:
<223> OTHER INFORMATION: framework region of an antigen binder

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser
            20                  25                  30

<210> SEQ ID NO 5
<211> LENGTH: 14
<212> TYPE: PRT
<213> ORGANISM: Artificial
<220> FEATURE:
<223> OTHER INFORMATION: framework region of an antigen binder
```

```
<400> SEQUENCE: 5

Trp Val Arg Gln Ala Pro Gly Lys Gly Leu Glu Trp Val Ser
1               5                   10

<210> SEQ ID NO 6
<211> LENGTH: 32
<212> TYPE: PRT
<213> ORGANISM: Artificial
<220> FEATURE:
<223> OTHER INFORMATION: framework region of an antigen binder

<400> SEQUENCE: 6

Arg Phe Thr Ile Ser Arg His Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 7
<211> LENGTH: 11
<212> TYPE: PRT
<213> ORGANISM: Artificial
<220> FEATURE:
<223> OTHER INFORMATION: framework region of an antigen binder

<400> SEQUENCE: 7

Trp Gly Gln Gly Thr Leu Val Thr Val Ser Ser
1               5                   10

<210> SEQ ID NO 8
<211> LENGTH: 220
<212> TYPE: PRT
<213> ORGANISM: Artificial
<220> FEATURE:
<223> OTHER INFORMATION: heavy chain variable region of an antigen
      binder

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Gly Asp Tyr Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220

<210> SEQ ID NO 9
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 9

Arg Ala Ser Gln Ser Val Ser Ser Tyr Leu Ala
1               5                   10

<210> SEQ ID NO 10
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 10

Trp Ala Ser Thr Arg Glu Ser
1               5

<210> SEQ ID NO 11
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 11

Gln Gln Tyr Gly Ser Ser Pro Leu Thr
1               5

<210> SEQ ID NO 12
<211> LENGTH: 23
<212> TYPE: PRT
<213> ORGANISM: Artificial
<220> FEATURE:
<223> OTHER INFORMATION: framework region of an antigen binder

<400> SEQUENCE: 12

Asp Val Val Met Thr Gln Ser Pro Ala Thr Leu Ser Leu Ser Pro Gly
1               5                   10                  15

Glu Lys Ala Thr Leu Ser Cys
            20

<210> SEQ ID NO 13
<211> LENGTH: 15
<212> TYPE: PRT
<213> ORGANISM: Artificial
<220> FEATURE:
<223> OTHER INFORMATION: framework region of an antigen binder

<400> SEQUENCE: 13

Trp Tyr Gln Gln Lys Pro Gly Gln Pro Pro Lys Leu Leu Ile Tyr
1               5                   10                  15
```

```
<210> SEQ ID NO 14
<211> LENGTH: 32
<212> TYPE: PRT
<213> ORGANISM: Artificial
<220> FEATURE:
<223> OTHER INFORMATION: framework region of an antigen binder

<400> SEQUENCE: 14
```

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

```
<210> SEQ ID NO 15
<211> LENGTH: 10
<212> TYPE: PRT
<213> ORGANISM: Artificial
<220> FEATURE:
<223> OTHER INFORMATION: framework region of an antigen binder

<400> SEQUENCE: 15
```

Phe Gly Gly Gly Thr Lys Val Glu Ile Lys
1               5                   10

```
<210> SEQ ID NO 16
<211> LENGTH: 214
<212> TYPE: PRT
<213> ORGANISM: Artificial
<220> FEATURE:
<223> OTHER INFORMATION: light chain variable region of an antigen
      binder

<400> SEQUENCE: 16
```

Asp Val Val Met Thr Gln Ser Pro Ala Thr Leu Ser Leu Ser Pro Gly
1               5                   10                  15

Glu Lys Ala Thr Leu Ser Cys Arg Ala Ser Gln Ser Val Ser Ser Tyr
            20                  25                  30

Leu Ala Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Gly Ser Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

```
Phe Asn Arg Gly Glu Cys
    210

<210> SEQ ID NO 17
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 17

Ser Asn Ser Ala Ala Trp Asn
1               5

<210> SEQ ID NO 18
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 18

Arg Thr Tyr Tyr Arg Ser Lys Trp Tyr Asn Asp Tyr Ala Val Ser Val
1               5                   10                  15

Lys Ser

<210> SEQ ID NO 19
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 19

Glu Gln Gln Gln Leu Val Pro His Tyr Tyr Tyr Gly Met Asp Val
1               5                   10                  15

<210> SEQ ID NO 20
<211> LENGTH: 30
<212> TYPE: PRT
<213> ORGANISM: Artificial
<220> FEATURE:
<223> OTHER INFORMATION: framework region of an antigen binder

<400> SEQUENCE: 20

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser
            20                  25                  30

<210> SEQ ID NO 21
<211> LENGTH: 14
<212> TYPE: PRT
<213> ORGANISM: Artificial
<220> FEATURE:
<223> OTHER INFORMATION: framework region of an antigen binder

<400> SEQUENCE: 21

Trp Ile Arg Gln Ser Pro Ser Arg Gly Leu Glu Trp Leu Gly
1               5                   10

<210> SEQ ID NO 22
```

```
<211> LENGTH: 32
<212> TYPE: PRT
<213> ORGANISM: Artificial
<220> FEATURE:
<223> OTHER INFORMATION: framework region of an antigen binder

<400> SEQUENCE: 22

Arg Ile Thr Ile Asn Pro Asp Thr Ser Lys Asn Gln Phe Ser Leu Gln
1               5                   10                  15
Leu Asn Ser Val Thr Pro Glu Asp Thr Ala Val Tyr Tyr Cys Ala Arg
            20                  25                  30

<210> SEQ ID NO 23
<211> LENGTH: 11
<212> TYPE: PRT
<213> ORGANISM: Artificial
<220> FEATURE:
<223> OTHER INFORMATION: framework region of an antigen binder

<400> SEQUENCE: 23

Trp Gly Gln Gly Thr Thr Val Thr Val Ser Ser
1               5                   10

<210> SEQ ID NO 24
<211> LENGTH: 235
<212> TYPE: PRT
<213> ORGANISM: Artificial
<220> FEATURE:
<223> OTHER INFORMATION: heavy chain variable region of an antigen
      binder

<400> SEQUENCE: 24

Gln Val Gln Leu Gln Gln Ser Gly Pro Gly Leu Val Lys Pro Ser Gln
1               5                   10                  15
Thr Leu Ser Leu Thr Cys Ala Ile Ser Gly Asp Ser Val Ser Ser Asn
            20                  25                  30
Ser Ala Ala Trp Asn Trp Ile Arg Gln Ser Pro Ser Arg Gly Leu Glu
        35                  40                  45
Trp Leu Gly Arg Thr Tyr Tyr Arg Ser Lys Trp Tyr Asn Asp Tyr Ala
    50                  55                  60
Val Ser Val Lys Ser Arg Ile Thr Ile Asn Pro Asp Thr Ser Lys Asn
65                  70                  75                  80
Gln Phe Ser Leu Gln Leu Asn Ser Val Thr Pro Glu Asp Thr Ala Val
                85                  90                  95
Tyr Tyr Cys Ala Arg Glu Gln Gln Leu Val Pro His Tyr Tyr Tyr
            100                 105                 110
Tyr Gly Met Asp Val Trp Gly Gln Gly Thr Thr Val Thr Val Ser Ser
        115                 120                 125
Ala Ser Thr Lys Gly Pro Ser Val Phe Pro Leu Ala Pro Ser Ser Lys
    130                 135                 140
Ser Thr Ser Gly Gly Thr Ala Ala Leu Gly Cys Leu Val Lys Asp Tyr
145                 150                 155                 160
Phe Pro Glu Pro Val Thr Val Ser Trp Asn Ser Gly Ala Leu Thr Ser
                165                 170                 175
Gly Val His Thr Phe Pro Ala Val Leu Gln Ser Ser Gly Leu Tyr Ser
            180                 185                 190
Leu Ser Ser Val Val Thr Val Pro Ser Ser Ser Leu Gly Thr Gln Thr
        195                 200                 205
Tyr Ile Cys Asn Val Asn His Lys Pro Ser Asn Thr Lys Val Asp Lys
    210                 215                 220
```

Lys Val Glu Pro Lys Ser Cys Asp Lys Thr Ser
225                 230                 235

<210> SEQ ID NO 25
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 25

Thr Gly Thr Thr Ser Asp Val Gly Gly Tyr Asn Tyr Val Ser
1               5                   10

<210> SEQ ID NO 26
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 26

Glu Val Ser Lys Arg Pro Ser
1               5

<210> SEQ ID NO 27
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 27

Ser Ser Tyr Thr Ser Ser Ser Thr Leu
1               5

<210> SEQ ID NO 28
<211> LENGTH: 22
<212> TYPE: PRT
<213> ORGANISM: Artificial
<220> FEATURE:
<223> OTHER INFORMATION: framework region of an antigen binder

<400> SEQUENCE: 28

Asp Val Val Met Thr Gln Ser Pro Ser Val Ser Gly Ser Pro Gly Gln
1               5                   10                  15

Ser Val Thr Ile Ser Cys
            20

<210> SEQ ID NO 29
<211> LENGTH: 15
<212> TYPE: PRT
<213> ORGANISM: Artificial
<220> FEATURE:
<223> OTHER INFORMATION: framework region of an antigen binder

<400> SEQUENCE: 29

Trp Tyr Gln Gln Arg Pro Gly Lys Ala Pro Lys Leu Met Ile Tyr
1               5                   10                  15

<210> SEQ ID NO 30
<211> LENGTH: 32
<212> TYPE: PRT

```
<213> ORGANISM: Artificial
<220> FEATURE:
<223> OTHER INFORMATION: framework region of an antigen binder

<400> SEQUENCE: 30

Gly Val Pro Asp Arg Phe Ser Gly Ser Lys Ser Gly Asn Thr Ala Ser
1               5                   10                  15

Leu Thr Val Ser Gly Leu Gln Ala Glu Asp Glu Ala Asp Tyr Tyr Cys
            20                  25                  30

<210> SEQ ID NO 31
<211> LENGTH: 11
<212> TYPE: PRT
<213> ORGANISM: Artificial
<220> FEATURE:
<223> OTHER INFORMATION: framework region of an antigen binder

<400> SEQUENCE: 31

Phe Gly Thr Gly Thr Lys Leu Thr Val Leu Gly
1               5                   10

<210> SEQ ID NO 32
<211> LENGTH: 215
<212> TYPE: PRT
<213> ORGANISM: Artificial
<220> FEATURE:
<223> OTHER INFORMATION: light chain variable region of an antigen
      binder

<400> SEQUENCE: 32

Asp Val Val Met Thr Gln Ser Pro Ser Val Ser Gly Ser Pro Gly Gln
1               5                   10                  15

Ser Val Thr Ile Ser Cys Thr Gly Thr Ser Asp Val Gly Gly Tyr
            20                  25                  30

Asn Tyr Val Ser Trp Tyr Gln Gln Arg Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Phe Gly Thr Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

```
<210> SEQ ID NO 33
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 33

Gly Phe Thr Phe Ser Ser Tyr Ala
1               5

<210> SEQ ID NO 34
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 34

Ile Ser Thr Asp Gly Gly Ser Thr
1               5

<210> SEQ ID NO 35
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 35

Ala Lys Thr Tyr Tyr Asp Phe Trp Arg Thr Tyr Tyr Gly Met Asp Val
1               5                   10                  15

<210> SEQ ID NO 36
<211> LENGTH: 25
<212> TYPE: PRT
<213> ORGANISM: Artificial
<220> FEATURE:
<223> OTHER INFORMATION: framework region of an antigen binder

<400> SEQUENCE: 36

Glu Val Gln Leu Val Gln Ser Gly Gly Gly Leu Val Gln Pro Gly Gly
1               5                   10                  15

Ser Leu Arg Leu Ser Cys Ser Ala Ser
            20                  25

<210> SEQ ID NO 37
<211> LENGTH: 17
<212> TYPE: PRT
<213> ORGANISM: Artificial
<220> FEATURE:
<223> OTHER INFORMATION: framework region of an antigen binder

<400> SEQUENCE: 37

Met His Trp Val Arg Gln Ala Pro Gly Lys Gly Leu Glu Tyr Val Ser
1               5                   10                  15

Ala

<210> SEQ ID NO 38
<211> LENGTH: 38
<212> TYPE: PRT
<213> ORGANISM: Artificial
<220> FEATURE:
<223> OTHER INFORMATION: framework region of an antigen binder
```

<400> SEQUENCE: 38

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 39
<211> LENGTH: 11
<212> TYPE: PRT
<213> ORGANISM: Artificial
<220> FEATURE:
<223> OTHER INFORMATION: framework region of an antigen binder

<400> SEQUENCE: 39

Trp Gly Gln Gly Thr Met Val Thr Val Ser Ser
1               5                   10

<210> SEQ ID NO 40
<211> LENGTH: 123
<212> TYPE: PRT
<213> ORGANISM: Artificial
<220> FEATURE:
<223> OTHER INFORMATION: heavy chain variable region of an antigen
      binder

<400> SEQUENCE: 40

Glu Val Gln Leu Val Gln Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Thr Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Tyr Tyr Asp Phe Trp Arg Thr Tyr Tyr Gly Met Asp Val
            100                 105                 110

Trp Gly Gln Gly Thr Met Val Thr Val Ser Ser
        115                 120

<210> SEQ ID NO 41
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 41

Gln Ser Ile Ser Ser Tyr
1               5

<210> SEQ ID NO 42
<211> LENGTH: 3
<212> TYPE: PRT
<213> ORGANISM: Artificial

```
<220> FEATURE:
<223> OTHER INFORMATION: complementary determining region of an antigen
      binder

<400> SEQUENCE: 42

Ala Ala Ser
1

<210> SEQ ID NO 43
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 43

Gln Gln Ser Tyr Ser Thr Pro Tyr Thr
1               5

<210> SEQ ID NO 44
<211> LENGTH: 26
<212> TYPE: PRT
<213> ORGANISM: Artificial
<220> FEATURE:
<223> OTHER INFORMATION: framework region of an antigen binder

<400> SEQUENCE: 44

Glu Ala Thr Leu Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 45
<211> LENGTH: 17
<212> TYPE: PRT
<213> ORGANISM: Artificial
<220> FEATURE:
<223> OTHER INFORMATION: framework region of an antigen binder

<400> SEQUENCE: 45

Leu Asn Trp Tyr Gln Gln Lys Pro Gly Arg Ala Pro Lys Leu Leu Ile
1               5                   10                  15

Tyr

<210> SEQ ID NO 46
<211> LENGTH: 36
<212> TYPE: PRT
<213> ORGANISM: Artificial
<220> FEATURE:
<223> OTHER INFORMATION: framework region of an antigen binder

<400> SEQUENCE: 46

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 47
<211> LENGTH: 11
<212> TYPE: PRT
<213> ORGANISM: Artificial
<220> FEATURE:
```

<223> OTHER INFORMATION: framework region of an antigen binder

<400> SEQUENCE: 47

Phe Gly Gln Gly Thr Arg Leu Glu Ile Lys Arg
1               5                   10

<210> SEQ ID NO 48
<211> LENGTH: 108
<212> TYPE: PRT
<213> ORGANISM: Artificial
<220> FEATURE:
<223> OTHER INFORMATION: light chain variable region of an antigen
      binder

<400> SEQUENCE: 48

Glu Ala Thr Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Arg Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Arg Leu Glu Ile Lys Arg
            100                 105

<210> SEQ ID NO 49
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 49

Gly Phe Thr Phe Ser Asn Tyr Ala
1               5

<210> SEQ ID NO 50
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 50

Ile Ala Gly Ser Gly Asp Asn Thr
1               5

<210> SEQ ID NO 51
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 51

Ala Arg Asp Arg Tyr Tyr Thr Met Asp Val

```
1               5                   10
```

<210> SEQ ID NO 52
<211> LENGTH: 25
<212> TYPE: PRT
<213> ORGANISM: Artificial
<220> FEATURE:
<223> OTHER INFORMATION: framework region of an antigen binder

<400> SEQUENCE: 52

```
Glu Val Gln Leu Val Gln Ser Gly Gly Gly Leu Val Gln Pro Gly Gly
1               5                   10                  15

Ser Leu Arg Leu Ser Cys Ala Ala Ser
            20                  25
```

<210> SEQ ID NO 53
<211> LENGTH: 17
<212> TYPE: PRT
<213> ORGANISM: Artificial
<220> FEATURE:
<223> OTHER INFORMATION: framework region of an antigen binder

<400> SEQUENCE: 53

```
Met Thr Trp Val Arg Gln Ala Pro Gly Lys Gly Leu Glu Trp Val Ser
1               5                   10                  15

Thr
```

<210> SEQ ID NO 54
<211> LENGTH: 38
<212> TYPE: PRT
<213> ORGANISM: Artificial
<220> FEATURE:
<223> OTHER INFORMATION: framework region of an antigen binder

<400> SEQUENCE: 54

```
Tyr Tyr Ala Asp Ser Val Lys Gly Arg Phe Thr Ile Ser Arg Asp Asn
1               5                   10                  15

Asp Lys Asn Thr Leu Tyr Leu Gln Met Asn Ser Leu Arg Ala Asp Asp
            20                  25                  30

Thr Ala Val Tyr Tyr Cys
        35
```

<210> SEQ ID NO 55
<211> LENGTH: 11
<212> TYPE: PRT
<213> ORGANISM: Artificial
<220> FEATURE:
<223> OTHER INFORMATION: framework region of an antigen binder

<400> SEQUENCE: 55

```
Trp Gly Gln Gly Thr Leu Val Thr Val Ser Ser
1               5                   10
```

<210> SEQ ID NO 56
<211> LENGTH: 117
<212> TYPE: PRT
<213> ORGANISM: Artificial
<220> FEATURE:
<223> OTHER INFORMATION: heavy chain variable region of an antigen
      binder

<400> SEQUENCE: 56

```
Glu Val Gln Leu Val Gln Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Thr Ile Ala Gly Ser Gly Asp Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Asp Arg Tyr Tyr Thr Met Asp Val Trp Gly Gln Gly Thr Leu
            100                 105                 110

Val Thr Val Ser Ser
            115

<210> SEQ ID NO 57
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 57

Ser Ser Asp Val Gly Gly Tyr Asn His
1               5

<210> SEQ ID NO 58
<211> LENGTH: 3
<212> TYPE: PRT
<213> ORGANISM: Artificial
<220> FEATURE:
<223> OTHER INFORMATION: complementary determining region of an antigen
      binder

<400> SEQUENCE: 58

Glu Val Ser
1

<210> SEQ ID NO 59
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 59

Gln Ser Tyr Asp Ser Ser Leu Ser Gly Ser Leu
1               5                   10

<210> SEQ ID NO 60
<211> LENGTH: 25
<212> TYPE: PRT
<213> ORGANISM: Artificial
<220> FEATURE:
<223> OTHER INFORMATION: framework region of an antigen binder

<400> SEQUENCE: 60

Gln Ser Val Val Thr Gln Pro Pro Ser Ala Ser Gly Ser Pro Gly Gln
1               5                   10                  15

Ser Val Thr Ile Ser Cys Thr Gly Thr
            20                  25
```

```
<210> SEQ ID NO 61
<211> LENGTH: 17
<212> TYPE: PRT
<213> ORGANISM: Artificial
<220> FEATURE:
<223> OTHER INFORMATION: framework region of an antigen binder

<400> SEQUENCE: 61

Val Ser Trp Tyr Gln Gln His Pro Gly Lys Ala Pro Lys Leu Leu Ile
1               5                   10                  15

Tyr

<210> SEQ ID NO 62
<211> LENGTH: 36
<212> TYPE: PRT
<213> ORGANISM: Artificial
<220> FEATURE:
<223> OTHER INFORMATION: framework region of an antigen binder

<400> SEQUENCE: 62

Glu Arg Pro Ser Gly Val Pro Asp Arg Phe Ser Gly Ser Lys Ser Asp
1               5                   10                  15

Asn Lys Ala Ser Leu Thr Ile Ile Gly Leu Gln Thr Glu Asp Glu Ala
            20                  25                  30

Asp Tyr Tyr Cys
        35

<210> SEQ ID NO 63
<211> LENGTH: 11
<212> TYPE: PRT
<213> ORGANISM: Artificial
<220> FEATURE:
<223> OTHER INFORMATION: framework region of an antigen binder

<400> SEQUENCE: 63

Phe Gly Thr Gly Thr Lys Leu Thr Val Leu Arg
1               5                   10

<210> SEQ ID NO 64
<211> LENGTH: 112
<212> TYPE: PRT
<213> ORGANISM: Artificial
<220> FEATURE:
<223> OTHER INFORMATION: light chain variable region of an antigen
      binder

<400> SEQUENCE: 64

Gln Ser Val Val Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn His Val Ser Trp Tyr Gln Gln His Pro Gly Lys Ala Pro Lys Leu
        35                  40                  45

Leu Ile Tyr Glu Val Ser Glu Arg Pro Ser Gly Val Pro Asp Arg Phe
    50                  55                  60

Ser Gly Ser Lys Ser Asp Asn Lys Ala Ser Leu Thr Ile Ile Gly Leu
65                  70                  75                  80

Gln Thr Glu Asp Glu Ala Asp Tyr Tyr Cys Gln Ser Tyr Asp Ser Ser
                85                  90                  95

Leu Ser Gly Ser Leu Phe Gly Thr Gly Thr Lys Leu Thr Val Leu Arg
            100                 105                 110
```

```
<210> SEQ ID NO 65
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 65

Gly Gly Ser Phe Ser Gly Tyr Tyr
1               5

<210> SEQ ID NO 66
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 66

Ile Asn His Ser Gly Ser Thr
1               5

<210> SEQ ID NO 67
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 67

Tyr Cys Val Arg Leu Pro Met Ile Lys Lys Ser Phe Asp Ile
1               5                   10

<210> SEQ ID NO 68
<211> LENGTH: 25
<212> TYPE: PRT
<213> ORGANISM: Artificial
<220> FEATURE:
<223> OTHER INFORMATION: framework region of an antigen binder

<400> SEQUENCE: 68

Lys Val Gln Leu Gln Gln Trp Gly Ala Gly Leu Leu Lys Pro Ser Glu
1               5                   10                  15

Thr Leu Ser Leu Thr Cys Ala Val Tyr
            20                  25

<210> SEQ ID NO 69
<211> LENGTH: 17
<212> TYPE: PRT
<213> ORGANISM: Artificial
<220> FEATURE:
<223> OTHER INFORMATION: framework region of an antigen binder

<400> SEQUENCE: 69

Trp Ser Trp Ile Arg Gln Pro Pro Gly Lys Gly Leu Glu Trp Ile Gly
1               5                   10                  15

Glu

<210> SEQ ID NO 70
<211> LENGTH: 36
<212> TYPE: PRT
<213> ORGANISM: Artificial
<220> FEATURE:
```

<223> OTHER INFORMATION: framework region of an antigen binder

<400> SEQUENCE: 70

Asn Tyr Asn Pro Ser Leu Lys Ser Arg Val Thr Ile Ser Val Asp Thr
1               5                   10                  15

Ser Lys Asn Gln Phe Ser Leu Lys Leu Ser Ser Val Thr Ala Ala Asp
            20                  25                  30

Thr Ala Val Tyr
        35

<210> SEQ ID NO 71
<211> LENGTH: 11
<212> TYPE: PRT
<213> ORGANISM: Artificial
<220> FEATURE:
<223> OTHER INFORMATION: framework region of an antigen binder

<400> SEQUENCE: 71

Trp Gly Pro Gly Thr Leu Val Thr Val Ser Ser
1               5                   10

<210> SEQ ID NO 72
<211> LENGTH: 118
<212> TYPE: PRT
<213> ORGANISM: Artificial
<220> FEATURE:
<223> OTHER INFORMATION: heavy chain variable region of an antigen
      binder

<400> SEQUENCE: 72

Lys Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Arg Leu Pro Met Ile Lys Lys Ser Phe Asp Ile Trp Gly Pro Gly Thr
            100                 105                 110

Leu Val Thr Val Ser Ser
        115

<210> SEQ ID NO 73
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 73

Gly Phe Thr Phe Ser Ser Tyr Ala
1               5

<210> SEQ ID NO 74
<211> LENGTH: 7
<212> TYPE: PRT

```
<213> ORGANISM: Artificial
<220> FEATURE:
<223> OTHER INFORMATION: complementary determining region of an antigen
      binder

<400> SEQUENCE: 74

Ile Tyr His Asp Gly Ser Thr
1               5

<210> SEQ ID NO 75
<211> LENGTH: 13
<212> TYPE: PRT
<213> ORGANISM: Artificial
<220> FEATURE:
<223> OTHER INFORMATION: complementary determining region of an antigen
      binder

<400> SEQUENCE: 75

Ala Arg Val Trp Leu Tyr Gly Ser Gly Tyr Met Asp Val
1               5                   10

<210> SEQ ID NO 76
<211> LENGTH: 25
<212> TYPE: PRT
<213> ORGANISM: Artificial
<220> FEATURE:
<223> OTHER INFORMATION: framework region of an antigen binder

<400> SEQUENCE: 76

Glu Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 77
<211> LENGTH: 17
<212> TYPE: PRT
<213> ORGANISM: Artificial
<220> FEATURE:
<223> OTHER INFORMATION: framework region of an antigen binder

<400> SEQUENCE: 77

Met His Trp Val Arg Gln Ala Pro Gly Lys Gly Leu Glu Trp Ile Gly
1               5                   10                  15

Asn

<210> SEQ ID NO 78
<211> LENGTH: 38
<212> TYPE: PRT
<213> ORGANISM: Artificial
<220> FEATURE:
<223> OTHER INFORMATION: framework region of an antigen binder

<400> SEQUENCE: 78

Phe Tyr Asn Pro Ser Leu Lys Ser Leu Val Thr Ile Ser Arg Asp Asp
1               5                   10                  15

Ser Thr Asn Thr Leu Tyr Leu Gln Met Asn Ser Leu Arg Ala Glu Asp
            20                  25                  30

Thr Ala Ile Tyr Tyr Cys
            35

<210> SEQ ID NO 79
<211> LENGTH: 11
<212> TYPE: PRT
<213> ORGANISM: Artificial
```

<220> FEATURE:
<223> OTHER INFORMATION: framework region of an antigen binder

<400> SEQUENCE: 79

Trp Gly Lys Gly Thr Leu Val Thr Val Ser Ser
1               5                   10

<210> SEQ ID NO 80
<211> LENGTH: 119
<212> TYPE: PRT
<213> ORGANISM: Artificial
<220> FEATURE:
<223> OTHER INFORMATION: heavy chain variable region of an antigen
      binder

<400> SEQUENCE: 80

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Ile
            35                  40                  45

Gly Asn Ile Tyr His Asp Gly Ser Thr Phe Tyr Asn Pro Ser Leu Lys
        50                  55                  60

Ser Leu Val Thr Ile Ser Arg Asp Asp Ser Thr Asn Thr Leu Tyr Leu
65                  70                  75                  80

Gln Met Asn Ser Leu Arg Ala Glu Asp Thr Ala Ile Tyr Tyr Cys Ala
                85                  90                  95

Arg Val Trp Leu Tyr Gly Ser Gly Tyr Met Asp Val Trp Gly Lys Gly
            100                 105                 110

Thr Leu Val Thr Val Ser Ser
        115

<210> SEQ ID NO 81
<211> LENGTH: 5
<212> TYPE: PRT
<213> ORGANISM: Artificial
<220> FEATURE:
<223> OTHER INFORMATION: complementary determining region of an antigen
      binder

<400> SEQUENCE: 81

Asp Tyr Glu Met Ser
1               5

<210> SEQ ID NO 82
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 82

Glu Ile His His Ser Gly Ser Thr Tyr Tyr Asn Pro Ser Leu Lys Gly
1               5                   10                  15

<210> SEQ ID NO 83
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 83

Asp Val Ser Tyr His Ala Asp Val
1               5

<210> SEQ ID NO 84
<211> LENGTH: 30
<212> TYPE: PRT
<213> ORGANISM: Artificial
<220> FEATURE:
<223> OTHER INFORMATION: framework region of an antigen binder

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Ala Phe Asp Phe Tyr
            20                  25                  30

<210> SEQ ID NO 85
<211> LENGTH: 14
<212> TYPE: PRT
<213> ORGANISM: Artificial
<220> FEATURE:
<223> OTHER INFORMATION: framework region of an antigen binder

<400> SEQUENCE: 85

Trp Val Arg Gln Ala Pro Gly Lys Ala Leu Glu Trp Ile Gly
1               5                   10

<210> SEQ ID NO 86
<211> LENGTH: 32
<212> TYPE: PRT
<213> ORGANISM: Artificial
<220> FEATURE:
<223> OTHER INFORMATION: framework region of an antigen binder

<400> SEQUENCE: 86

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 87
<211> LENGTH: 11
<212> TYPE: PRT
<213> ORGANISM: Artificial
<220> FEATURE:
<223> OTHER INFORMATION: framework region of an antigen binder

<400> SEQUENCE: 87

Trp Gly Gln Gly Thr Thr Val Thr Val Ser Ser
1               5                   10

<210> SEQ ID NO 88
<211> LENGTH: 116
<212> TYPE: PRT
<213> ORGANISM: Artificial
<220> FEATURE:
<223> OTHER INFORMATION: heavy chain variable region of an antigen
      binder

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Ala Phe Asp Phe Tyr Asp Tyr

```
                    20                  25                  30

Glu Met Ser Trp Val Arg Gln Ala Pro Gly Lys Ala Leu Glu Trp Ile
            35                  40                  45

Gly Glu Ile His His Ser Gly Ser Thr Tyr Tyr Asn Pro Ser Leu Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Val Ser Tyr His Ala Asp Val Trp Gly Gln Gly Thr Thr Val
                100                 105                 110

Thr Val Ser Ser
        115

<210> SEQ ID NO 89
<211> LENGTH: 5
<212> TYPE: PRT
<213> ORGANISM: Artificial
<220> FEATURE:
<223> OTHER INFORMATION: complementary determining region of an antigen
      binder

<400> SEQUENCE: 89

Asp Tyr Ala Met Ser
1               5

<210> SEQ ID NO 90
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 90

Arg Met Tyr Asn Asn Gly Arg Thr Ser Tyr Asn Pro Ser Leu Lys Ser
1               5                   10                  15

<210> SEQ ID NO 91
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 91

Asp Asn Leu Gly Tyr Arg Pro Ser Glu Asn Leu Tyr Gly Met Asp Val
1               5                   10                  15

<210> SEQ ID NO 92
<211> LENGTH: 30
<212> TYPE: PRT
<213> ORGANISM: Artificial
<220> FEATURE:
<223> OTHER INFORMATION: framework region of an antigen binder

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp
            20                  25                  30
```

```
<210> SEQ ID NO 93
<211> LENGTH: 14
<212> TYPE: PRT
<213> ORGANISM: Artificial
<220> FEATURE:
<223> OTHER INFORMATION: framework region of an antigen binder

<400> SEQUENCE: 93

Trp Val Arg Gln Ala Pro Gly Lys Gly Leu Glu Trp Ile Gly
1               5                   10

<210> SEQ ID NO 94
<211> LENGTH: 32
<212> TYPE: PRT
<213> ORGANISM: Artificial
<220> FEATURE:
<223> OTHER INFORMATION: framework region of an antigen binder

<400> SEQUENCE: 94

Leu Val Thr Ile Ser Arg Asp Asn Ser Lys Asn Thr Leu Tyr Leu Gln
1               5                   10                  15

Met Asn Ser Leu Arg Ala Glu Asp Thr Ala Thr Tyr Tyr Cys Ala Arg
                20                  25                  30

<210> SEQ ID NO 95
<211> LENGTH: 11
<212> TYPE: PRT
<213> ORGANISM: Artificial
<220> FEATURE:
<223> OTHER INFORMATION: framework region of an antigen binder

<400> SEQUENCE: 95

Trp Gly Gln Gly Thr Thr Val Thr Val Ser Ser
1               5                   10

<210> SEQ ID NO 96
<211> LENGTH: 124
<212> TYPE: PRT
<213> ORGANISM: Artificial
<220> FEATURE:
<223> OTHER INFORMATION: heavy chain variable region of an antigen
      binder

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
                20                  25                  30

Ala Met Ser Trp Val Arg Gln Ala Pro Gly Lys Gly Leu Glu Trp Ile
            35                  40                  45

Gly Arg Met Tyr Asn Asn Gly Arg Thr Ser Tyr Asn Pro Ser Leu Lys
    50                  55                  60

Ser Leu Val Thr Ile Ser Arg Asp Asn Ser Lys Asn Thr Leu Tyr Leu
65                  70                  75                  80

Gln Met Asn Ser Leu Arg Ala Glu Asp Thr Ala Thr Tyr Tyr Cys Ala
                85                  90                  95

Arg Asp Asn Leu Gly Tyr Arg Pro Ser Glu Asn Leu Tyr Gly Met Asp
            100                 105                 110

Val Trp Gly Gln Gly Thr Thr Val Thr Val Ser Ser
        115                 120

<210> SEQ ID NO 97
<211> LENGTH: 5
```

```
<212> TYPE: PRT
<213> ORGANISM: Artificial
<220> FEATURE:
<223> OTHER INFORMATION: complementary determining region of an antigen
      binder

<400> SEQUENCE: 97

Asp Tyr Tyr Ile Gly
1               5

<210> SEQ ID NO 98
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 98

Ser Met Tyr His Ser Gly Arg Thr Tyr Ile Asn Pro Ser Leu Lys Ser
1               5                  10                  15

<210> SEQ ID NO 99
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 99

Gly Gly Ile Thr Gly Thr Thr Pro Ile Asp Tyr
1               5                  10

<210> SEQ ID NO 100
<211> LENGTH: 30
<212> TYPE: PRT
<213> ORGANISM: Artificial
<220> FEATURE:
<223> OTHER INFORMATION: framework region of an antigen binder

<400> SEQUENCE: 100

Glu Val Gln Leu Val Glu Ser Gly Gly Gly Leu Val Gln Pro Gly Gly
1               5                  10                  15

Ser Leu Arg Leu Ser Cys Lys Gly Ser Gly Phe Thr Leu Ser
            20                  25                  30

<210> SEQ ID NO 101
<211> LENGTH: 14
<212> TYPE: PRT
<213> ORGANISM: Artificial
<220> FEATURE:
<223> OTHER INFORMATION: framework region of an antigen binder

<400> SEQUENCE: 101

Trp Val Arg Gln Ala Pro Gly Lys Gly Leu Glu Trp Ile Gly
1               5                  10

<210> SEQ ID NO 102
<211> LENGTH: 32
<212> TYPE: PRT
<213> ORGANISM: Artificial
<220> FEATURE:
<223> OTHER INFORMATION: framework region of an antigen binder

<400> SEQUENCE: 102

Arg Val Thr Ile Ser Arg Asp Asn Ser Lys Asn Thr Leu Tyr Leu Gln
```

```
                1               5                  10                 15
Met Asn Ser Leu Arg Ala Glu Asp Thr Ala Val Tyr Tyr Cys Ala Arg
                20                 25                 30
```

<210> SEQ ID NO 103
<211> LENGTH: 11
<212> TYPE: PRT
<213> ORGANISM: Artificial
<220> FEATURE:
<223> OTHER INFORMATION: framework region of an antigen binder

<400> SEQUENCE: 103

```
Trp Gly Gln Gly Thr Leu Val Thr Val Ser Ser
1               5                  10
```

<210> SEQ ID NO 104
<211> LENGTH: 119
<212> TYPE: PRT
<213> ORGANISM: Artificial
<220> FEATURE:
<223> OTHER INFORMATION: heavy chain variable region of an antigen
      binder

<400> SEQUENCE: 104

```
Glu Val Gln Leu Val Glu Ser Gly Gly Gly Leu Val Gln Pro Gly Gly
1               5                  10                 15

Ser Leu Arg Leu Ser Cys Lys Gly Ser Gly Phe Thr Leu Ser Asp Tyr
                20                 25                 30

Tyr Ile Gly Trp Val Arg Gln Ala Pro Gly Lys Gly Leu Glu Trp Ile
            35                 40                 45

Gly Ser Met Tyr His Ser Gly Arg Thr Tyr Ile Asn Pro Ser Leu Lys
        50                 55                 60

Ser Arg Val Thr Ile Ser Arg Asp Asn Ser Lys Asn Thr Leu Tyr Leu
65                  70                 75                 80

Gln Met Asn Ser Leu Arg Ala Glu Asp Thr Ala Val Tyr Tyr Cys Ala
                85                 90                 95

Arg Gly Gly Ile Thr Gly Thr Thr Pro Ile Asp Tyr Trp Gly Gln Gly
            100                105                110

Thr Leu Val Thr Val Ser Ser
        115
```

<210> SEQ ID NO 105
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 105

```
Ser Ser Asn Tyr Met Ser
1               5
```

<210> SEQ ID NO 106
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 106

```
Val Ser Ser Asn Tyr Met Ser
```

```
1               5

<210> SEQ ID NO 107
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 107

Thr Val Ser Ser Asn Tyr Met Ser
1               5

<210> SEQ ID NO 108
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 108

Phe Thr Val Ser Ser Asn Tyr Met Ser
1               5

<210> SEQ ID NO 109
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 109

Gly Phe Thr Val Ser Ser Asn Tyr Met Ser
1               5                   10

<210> SEQ ID NO 110
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 110

Gly Phe Thr Val Ser Ser Asn Tyr Met His
1               5                   10

<210> SEQ ID NO 111
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 111

Gly Phe Thr Phe Ser Ser Asn Tyr Met Ser
1               5                   10

<210> SEQ ID NO 112
<211> LENGTH: 10
<212> TYPE: PRT
<213> ORGANISM: Artificial
<220> FEATURE:
<223> OTHER INFORMATION: complementary determining region of an antigen
``` binder

<400> SEQUENCE: 112

Gly Leu Thr Val Ser Ser Asn Tyr Met Ser
1               5                   10

<210> SEQ ID NO 113
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 113

Ser Ser Asn Tyr Met Gly
1               5

<210> SEQ ID NO 114
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 114

Val Ser Ser Asn Tyr Met Gly
1               5

<210> SEQ ID NO 115
<211> LENGTH: 17
<212> TYPE: PRT
<213> ORGANISM: Artificial
<220> FEATURE:
<223> OTHER INFORMATION: complementary determining region of an antigen
      binder

<400> SEQUENCE: 115

Val Ile Tyr Ser Gly Gly Ser Thr Tyr Tyr Ala Asp Ser Val Lys Ser
1               5                   10                  15

Asp

<210> SEQ ID NO 116
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 116

Val Ile Tyr Ser Gly Gly Ser Thr Tyr Tyr Ala Asp Ser Val Lys Asp
1               5                   10                  15

<210> SEQ ID NO 117
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 117

Val Ile Tyr Ser Gly Gly Ser Thr Tyr Tyr Ala Asp Ser Val Gln Gly
1               5                   10                  15

<210> SEQ ID NO 118
<211> LENGTH: 16
<212> TYPE: PRT
<213> ORGANISM: Artificial
<220> FEATURE:
<223> OTHER INFORMATION: complementary determining region of an antigen binder

<400> SEQUENCE: 118

Val Ile Tyr Ser Gly Gly Ser Thr Tyr Tyr Ala Asp Ser Val Gln Asp
1               5                   10                  15

<210> SEQ ID NO 119
<211> LENGTH: 16
<212> TYPE: PRT
<213> ORGANISM: Artificial
<220> FEATURE:
<223> OTHER INFORMATION: complementary determining region of an antigen binder

<400> SEQUENCE: 119

Val Ile Tyr Ser Gly Gly Ser Thr Tyr Tyr Asn Asp Ser Val Gln Asp
1               5                   10                  15

<210> SEQ ID NO 120
<211> LENGTH: 16
<212> TYPE: PRT
<213> ORGANISM: Artificial
<220> FEATURE:
<223> OTHER INFORMATION: complementary determining region of an antigen binder

<400> SEQUENCE: 120

Val Ile Tyr Ser Gly Gly Ser Thr Tyr Tyr Asn Asp Lys Val Gln Asp
1               5                   10                  15

<210> SEQ ID NO 121
<211> LENGTH: 16
<212> TYPE: PRT
<213> ORGANISM: Artificial
<220> FEATURE:
<223> OTHER INFORMATION: complementary determining region of an antigen binder

<400> SEQUENCE: 121

Val Ile Tyr Ser Gly Gly Ser Thr Tyr Tyr Ala Asp Ser Phe Lys Ser
1               5                   10                  15

<210> SEQ ID NO 122
<211> LENGTH: 16
<212> TYPE: PRT
<213> ORGANISM: Artificial
<220> FEATURE:
<223> OTHER INFORMATION: complementary determining region of an antigen binder

<400> SEQUENCE: 122

Val Ile Tyr Ser Gly Gly Ser Thr Tyr Tyr Ala Asp Lys Phe Lys Ser
1               5                   10                  15

<210> SEQ ID NO 123
<211> LENGTH: 16
<212> TYPE: PRT
<213> ORGANISM: Artificial
<220> FEATURE:
<223> OTHER INFORMATION: complementary determining region of an antigen binder

```
<400> SEQUENCE: 123

Val Ile Tyr Ser Gly Gly Ser Thr Tyr Tyr Ala Glu Lys Phe Lys Ser
1               5                   10                  15

<210> SEQ ID NO 124
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 124

Val Ile Tyr Ser Gly Gly Ser Thr Tyr Tyr Ala Glu Lys Val Gln Asp
1               5                   10                  15

<210> SEQ ID NO 125
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 125

Ala Gly Tyr Gly Asp Tyr Tyr Phe Asp Tyr
1               5                   10

<210> SEQ ID NO 126
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 126

Arg Gly Tyr Gly Asp Tyr Tyr Phe Asp Tyr
1               5                   10

<210> SEQ ID NO 127
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 127

Ala Arg Gly Tyr Gly Asp Tyr Tyr Phe Asp Tyr
1               5                   10

<210> SEQ ID NO 128
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 128

Ala Lys Gly Tyr Gly Asp Tyr Tyr Phe Asp Tyr
1               5                   10

<210> SEQ ID NO 129
<211> LENGTH: 11
<212> TYPE: PRT
```

<213> ORGANISM: Artificial
<220> FEATURE:
<223> OTHER INFORMATION: complementary determining region of an antigen binder

<400> SEQUENCE: 129

Gly Arg Gly Tyr Gly Asp Tyr Tyr Phe Asp Tyr
1               5                   10

<210> SEQ ID NO 130
<211> LENGTH: 11
<212> TYPE: PRT
<213> ORGANISM: Artificial
<220> FEATURE:
<223> OTHER INFORMATION: complementary determining region of an antigen binder

<400> SEQUENCE: 130

Thr Arg Gly Tyr Gly Asp Tyr Tyr Phe Asp Tyr
1               5                   10

<210> SEQ ID NO 131
<211> LENGTH: 11
<212> TYPE: PRT
<213> ORGANISM: Artificial
<220> FEATURE:
<223> OTHER INFORMATION: complementary determining region of an antigen binder

<400> SEQUENCE: 131

Ser Arg Gly Tyr Gly Asp Tyr Tyr Phe Asp Tyr
1               5                   10

<210> SEQ ID NO 132
<211> LENGTH: 11
<212> TYPE: PRT
<213> ORGANISM: Artificial
<220> FEATURE:
<223> OTHER INFORMATION: complementary determining region of an antigen binder

<400> SEQUENCE: 132

Glu Arg Gly Tyr Gly Asp Tyr Tyr Phe Asp Tyr
1               5                   10

<210> SEQ ID NO 133
<211> LENGTH: 11
<212> TYPE: PRT
<213> ORGANISM: Artificial
<220> FEATURE:
<223> OTHER INFORMATION: complementary determining region of an antigen binder

<400> SEQUENCE: 133

Ala Ser Gly Tyr Gly Asp Tyr Tyr Phe Asp Tyr
1               5                   10

<210> SEQ ID NO 134
<211> LENGTH: 11
<212> TYPE: PRT
<213> ORGANISM: Artificial
<220> FEATURE:
<223> OTHER INFORMATION: complementary determining region of an antigen binder

<400> SEQUENCE: 134

Ala Thr Gly Tyr Gly Asp Tyr Tyr Phe Asp Tyr
1               5                   10

<210> SEQ ID NO 135
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 135

Arg Val Ser Gln Ser Val Ser Ser Tyr Leu Ala
1               5                   10

<210> SEQ ID NO 136
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 136

Arg Met Ser Gln Ser Val Ser Ser Tyr Leu Ala
1               5                   10

<210> SEQ ID NO 137
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 137

Arg Ser Ser Gln Ser Val Ser Ser Tyr Leu Ala
1               5                   10

<210> SEQ ID NO 138
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 138

Lys Ser Ser Gln Ser Val Ser Ser Tyr Leu Ala
1               5                   10

<210> SEQ ID NO 139
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 139

Arg Ala Arg Gln Ser Val Ser Ser Tyr Leu Ala
1               5                   10

<210> SEQ ID NO 140
<211> LENGTH: 11
<212> TYPE: PRT
<213> ORGANISM: Artificial
<220> FEATURE:
<223> OTHER INFORMATION: complementary determining region of an antigen
      binder -continued

<400> SEQUENCE: 140

Arg Ala Ser Gln Ser Val Ser Ser Tyr Leu His
1               5                   10

<210> SEQ ID NO 141
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 141

Arg Ala Ser Gln Ser Val Ser Ser Tyr Leu Ser
1               5                   10

<210> SEQ ID NO 142
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 142

Arg Ala Ser Gln Ser Val Ser Ser Tyr Leu Asp
1               5                   10

<210> SEQ ID NO 143
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 143

Arg Ala Ser Gln Ser Val Ser Ser Tyr Leu Asn
1               5                   10

<210> SEQ ID NO 144
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 144

Arg Ala Ser Gln Ser Val Ser Ser Tyr Leu Thr
1               5                   10

<210> SEQ ID NO 145
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 145

Tyr Ala Ser Thr Arg Glu Ser
1               5

<210> SEQ ID NO 146
<211> LENGTH: 7

```
<212> TYPE: PRT
<213> ORGANISM: Artificial
<220> FEATURE:
<223> OTHER INFORMATION: complementary determining region of an antigen
      binder

<400> SEQUENCE: 146

Trp Ala Ser Thr Arg Ala Ser
1               5

<210> SEQ ID NO 147
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 147

Trp Ala Ser Thr Arg Glu Thr
1               5

<210> SEQ ID NO 148
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 148

Trp Ala Ser Thr Arg Ala Thr
1               5

<210> SEQ ID NO 149
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 149

Asp Ala Ser Thr Arg Ala Thr
1               5

<210> SEQ ID NO 150
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 150

Asp Ala Ser Thr Arg Glu Thr
1               5

<210> SEQ ID NO 151
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 151

Trp Ala Ser Thr Arg Glu Ser Gly
```

```
1               5
```

<210> SEQ ID NO 152
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 152

```
Trp Ala Ser Thr Arg Glu Ser Gly Val
1               5
```

<210> SEQ ID NO 153
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 153

```
Gly Ala Ser Thr Arg Ala Thr
1               5
```

<210> SEQ ID NO 154
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 154

```
Asp Ala Ser Ser Arg Ala Thr
1               5
```

<210> SEQ ID NO 155
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 155

```
Lys Gln Tyr Gly Ser Ser Pro Leu Thr
1               5
```

<210> SEQ ID NO 156
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 156

```
Leu Gln Tyr Gly Ser Ser Pro Leu Thr
1               5
```

<210> SEQ ID NO 157
<211> LENGTH: 9
<212> TYPE: PRT
<213> ORGANISM: Artificial
<220> FEATURE:
<223> OTHER INFORMATION: complementary determining region of an antigen binder

<400> SEQUENCE: 157

Glu Gln Tyr Gly Ser Ser Pro Leu Thr
1               5

<210> SEQ ID NO 158
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 158

Met Gln Tyr Gly Ser Ser Pro Leu Thr
1               5

<210> SEQ ID NO 159
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 159

Thr Gln Tyr Gly Ser Ser Pro Leu Thr
1               5

<210> SEQ ID NO 160
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 160

His Gln Tyr Gly Ser Ser Pro Leu Thr
1               5

<210> SEQ ID NO 161
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 161

Gln Lys Tyr Gly Ser Ser Pro Leu Thr
1               5

<210> SEQ ID NO 162
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 162

Gln Arg Tyr Gly Ser Ser Pro Leu Thr
1               5

<210> SEQ ID NO 163

```
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 163

Glu Lys Tyr Gly Ser Ser Pro Leu Thr
1               5

<210> SEQ ID NO 164
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 164

Asn Gln Tyr Gly Ser Ser Pro Leu Thr
1               5

<210> SEQ ID NO 165
<211> LENGTH: 12
<212> TYPE: PRT
<213> ORGANISM: Artificial
<220> FEATURE:
<223> OTHER INFORMATION: complementary determining region of an antigen
      binder

<400> SEQUENCE: 165

Gly Asp Ser Val Ser Ser Asn Ser Ala Ala Trp Asn
1               5                   10

<210> SEQ ID NO 166
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 166

Asp Ser Val Ser Ser Asn Ser Ala Ala Trp Asn
1               5                   10

<210> SEQ ID NO 167
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 167

Ser Val Ser Ser Asn Ser Ala Ala Trp Asn
1               5                   10

<210> SEQ ID NO 168
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 168
```

```
Val Ser Ser Asn Ser Ala Ala Trp Asn
1               5
```

<210> SEQ ID NO 169
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 169

```
Ser Ser Asn Ser Ala Ala Trp Asn
1               5
```

<210> SEQ ID NO 170
<211> LENGTH: 12
<212> TYPE: PRT
<213> ORGANISM: Artificial
<220> FEATURE:
<223> OTHER INFORMATION: complementary determining region of an antigen
      binder

<400> SEQUENCE: 170

```
Gly Gly Ser Val Ser Ser Asn Ser Ala Ala Trp Asn
1               5                   10
```

<210> SEQ ID NO 171
<211> LENGTH: 12
<212> TYPE: PRT
<213> ORGANISM: Artificial
<220> FEATURE:
<223> OTHER INFORMATION: complementary determining region of an antigen
      binder

<400> SEQUENCE: 171

```
Gly Asp Ser Val Ser Ser Ile Ser Ala Ala Trp Asn
1               5                   10
```

<210> SEQ ID NO 172
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 172

```
Ser Ile Ser Ala Ala Trp Asn
1               5
```

<210> SEQ ID NO 173
<211> LENGTH: 12
<212> TYPE: PRT
<213> ORGANISM: Artificial
<220> FEATURE:
<223> OTHER INFORMATION: complementary determining region of an antigen
      binder

<400> SEQUENCE: 173

```
Gly Gly Ser Val Ser Ser Ile Ser Ala Ala Trp Asn
1               5                   10
```

<210> SEQ ID NO 174
<211> LENGTH: 12
<212> TYPE: PRT
<213> ORGANISM: Artificial
<220> FEATURE:

```
<223> OTHER INFORMATION: complementary determining region of an antigen
      binder

<400> SEQUENCE: 174

Gly Tyr Ser Val Ser Ser Ile Ser Ala Ala Trp Asn
1               5                   10

<210> SEQ ID NO 175
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 175

Ile Thr Tyr Tyr Arg Ser Lys Trp Tyr Asn Asp Tyr Ala Val Ser Val
1               5                   10                  15

Lys Ser

<210> SEQ ID NO 176
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 176

Ser Thr Tyr Tyr Arg Ser Lys Trp Tyr Asn Asp Tyr Ala Val Ser Val
1               5                   10                  15

Lys Ser

<210> SEQ ID NO 177
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 177

Arg Thr Tyr Tyr Arg Ser Lys Trp Tyr Asn Asp Tyr Ala Val Ser Leu
1               5                   10                  15

Lys Ser

<210> SEQ ID NO 178
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 178

Arg Thr Tyr Tyr Arg Ser Lys Trp Tyr Asn Asp Tyr Ala Val Ser Val
1               5                   10                  15

Lys Gly

<210> SEQ ID NO 179
<211> LENGTH: 18
<212> TYPE: PRT
<213> ORGANISM: Artificial
<220> FEATURE:
<223> OTHER INFORMATION: complementary determining region of an antigen
```

```
                              binder

<400> SEQUENCE: 179

Arg Thr Tyr Tyr Arg Ser Lys Trp Tyr Asn Tyr Ala Val Ser Val
1               5                   10                  15

Lys Ser

<210> SEQ ID NO 180
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 180

Arg Thr Tyr Tyr Arg Ser Lys Trp Tyr Asn Asp Tyr Ala Asp Ser Val
1               5                   10                  15

Lys Ser

<210> SEQ ID NO 181
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 181

Arg Thr Tyr Tyr Arg Ser Lys Trp Tyr Asn Tyr Ala Asp Ser Val
1               5                   10                  15

Lys Ser

<210> SEQ ID NO 182
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 182

Tyr Thr Tyr Tyr Arg Ser Lys Trp Tyr Asn Asp Tyr Ala Val Ser Val
1               5                   10                  15

Lys Ser

<210> SEQ ID NO 183
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 183

Glu Thr Tyr Tyr Arg Ser Lys Trp Tyr Asn Asp Tyr Ala Val Ser Val
1               5                   10                  15

Lys Ser

<210> SEQ ID NO 184
<211> LENGTH: 18
<212> TYPE: PRT
<213> ORGANISM: Artificial
<220> FEATURE:
```

```
<223> OTHER INFORMATION: complementary determining region of an antigen
      binder

<400> SEQUENCE: 184

Asp Thr Tyr Tyr Arg Ser Lys Trp Tyr Asn Asp Tyr Ala Val Ser Val
1               5                   10                  15

Lys Ser

<210> SEQ ID NO 185
<211> LENGTH: 17
<212> TYPE: PRT
<213> ORGANISM: Artificial
<220> FEATURE:
<223> OTHER INFORMATION: complementary determining region of an antigen
      binder

<400> SEQUENCE: 185

Arg Glu Gln Gln Gln Leu Val Pro His Tyr Tyr Tyr Gly Met Asp
1               5                   10                  15

Val

<210> SEQ ID NO 186
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 186

Ala Arg Glu Gln Gln Gln Leu Val Pro His Tyr Tyr Tyr Gly Met
1               5                   10                  15

Asp Val

<210> SEQ ID NO 187
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 187

Ala Thr Glu Gln Gln Gln Leu Val Pro His Tyr Tyr Tyr Gly Met
1               5                   10                  15

Asp Val

<210> SEQ ID NO 188
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 188

Ala Ala Glu Gln Gln Gln Leu Val Pro His Tyr Tyr Tyr Gly Met
1               5                   10                  15

Asp Val

<210> SEQ ID NO 189
<211> LENGTH: 18
<212> TYPE: PRT
<213> ORGANISM: Artificial
```

```
<220> FEATURE:
<223> OTHER INFORMATION: complementary determining region of an antigen
      binder

<400> SEQUENCE: 189

Ala Gly Glu Gln Gln Gln Leu Val Pro His Tyr Tyr Tyr Tyr Gly Met
1               5                   10                  15

Asp Val

<210> SEQ ID NO 190
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 190

Thr Arg Glu Gln Gln Gln Leu Val Pro His Tyr Tyr Tyr Tyr Gly Met
1               5                   10                  15

Asp Val

<210> SEQ ID NO 191
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 191

Ala Arg Glu Gln Gln Gln Leu Val Pro His Tyr Tyr Tyr Tyr Gly Met
1               5                   10                  15

Asp Val

<210> SEQ ID NO 192
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 192

Val Arg Glu Gln Gln Gln Leu Val Pro His Tyr Tyr Tyr Tyr Gly Met
1               5                   10                  15

Asp Val

<210> SEQ ID NO 193
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 193

Thr Arg Glu Gln Gln Gln Leu Val Pro His Tyr Tyr Tyr Tyr Gly Met
1               5                   10                  15

Asp Val

<210> SEQ ID NO 194
<211> LENGTH: 18
<212> TYPE: PRT
```

```
<213> ORGANISM: Artificial
<220> FEATURE:
<223> OTHER INFORMATION: complementary determining region of an antigen
      binder

<400> SEQUENCE: 194

Met Arg Glu Gln Gln Gln Leu Val Pro His Tyr Tyr Tyr Tyr Gly Met
1               5                   10                  15

Asp Val

<210> SEQ ID NO 195
<211> LENGTH: 15
<212> TYPE: PRT
<213> ORGANISM: Artificial
<220> FEATURE:
<223> OTHER INFORMATION: complementary determining region of an antigen
      binder

<400> SEQUENCE: 195

Thr Gly Thr Ser Ser Asp Val Gly Gly Tyr Asp Asn Tyr Val Ser
1               5                   10                  15

<210> SEQ ID NO 196
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 196

Ser Gly Thr Thr Ser Asp Val Gly Gly Tyr Asn Tyr Val Ser
1               5                   10

<210> SEQ ID NO 197
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 197

Thr Gly Ser Thr Ser Asp Val Gly Gly Tyr Asn Tyr Val Ser
1               5                   10

<210> SEQ ID NO 198
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 198

Ser Gly Ser Thr Ser Asp Val Gly Gly Tyr Asn Tyr Val Ser
1               5                   10

<210> SEQ ID NO 199
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 199
```

Thr Gly Thr Ser Ser Asp Val Gly Gly Tyr Asn Tyr Val Ser
1               5                   10

<210> SEQ ID NO 200
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 200

Thr Gly Thr Ser Ser Asn Val Gly Gly Tyr Asn Tyr Val Ser
1               5                   10

<210> SEQ ID NO 201
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 201

Thr Gly Thr Thr Ser Asp Ile Gly Gly Tyr Asn Tyr Val Ser
1               5                   10

<210> SEQ ID NO 202
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 202

Thr Gly Thr Thr Ser Asp Val Gly Ser Tyr Asn Tyr Val Ser
1               5                   10

<210> SEQ ID NO 203
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 203

Thr Gly Thr Thr Ser Asp Val Gly Gly Tyr Asp Tyr Val Ser
1               5                   10

<210> SEQ ID NO 204
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 204

Thr Gly Ser Thr Ser Asp Val Gly Gly Tyr Asp Tyr Val Ser
1               5                   10

<210> SEQ ID NO 205
<211> LENGTH: 7
<212> TYPE: PRT
<213> ORGANISM: Artificial
<220> FEATURE:

```
<223> OTHER INFORMATION: complementary determining region of an antigen
      binder

<400> SEQUENCE: 205

Asp Val Ser Lys Arg Pro Ser
1               5

<210> SEQ ID NO 206
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 206

Glu Val Asn Lys Arg Pro Ser
1               5

<210> SEQ ID NO 207
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 207

Glu Val Ser Asn Arg Pro Ser
1               5

<210> SEQ ID NO 208
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 208

Asp Val Ser Asn Arg Pro Ser
1               5

<210> SEQ ID NO 209
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 209

Glu Gly Ser Lys Arg Pro Ser
1               5

<210> SEQ ID NO 210
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 210

Asp Asn Asn Lys Arg Pro Ser
1               5
```

```
<210> SEQ ID NO 211
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 211

Glu Asn Asn Lys Arg Pro Ser
1               5

<210> SEQ ID NO 212
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 212

Gln Asp Ser Lys Arg Pro Ser
1               5

<210> SEQ ID NO 213
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 213

Asn Val Asn Lys Arg Pro Ser
1               5

<210> SEQ ID NO 214
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 214

Glu Asp Ser Lys Arg Pro Ser
1               5

<210> SEQ ID NO 215
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 215

Ser Leu Tyr Thr Ser Ser Ser Thr Leu
1               5

<210> SEQ ID NO 216
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 216
```

```
Ser Ser Tyr Ala Ser Ser Ser Thr Leu
1               5

<210> SEQ ID NO 217
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 217

Ser Ser Tyr Ser Ser Ser Ser Thr Leu
1               5

<210> SEQ ID NO 218
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 218

Ser Ser Tyr Thr Ser Ser Ser Thr Phe
1               5

<210> SEQ ID NO 219
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 219

Ser Ser Tyr Thr Gly Ser Ser Thr Leu
1               5

<210> SEQ ID NO 220
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 220

Ser Ser Tyr Thr Gly Ser Ser Thr Phe
1               5

<210> SEQ ID NO 221
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 221

Ser Leu Tyr Thr Ser Ser Ser Thr Phe
1               5

<210> SEQ ID NO 222
<211> LENGTH: 9
<212> TYPE: PRT
<213> ORGANISM: Artificial
```

```
<220> FEATURE:
<223> OTHER INFORMATION: complementary determining region of an antigen
      binder

<400> SEQUENCE: 222

Ser Leu Tyr Ala Ser Ser Ser Thr Leu
1               5

<210> SEQ ID NO 223
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 223

Ser Leu Tyr Ala Ser Ser Ser Thr Phe
1               5

<210> SEQ ID NO 224
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 224

Ser Ser Tyr Ala Gly Ser Ser Thr Phe
1               5

<210> SEQ ID NO 225
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 225

Gly Phe Thr Phe Ser Ser Tyr Thr
1               5

<210> SEQ ID NO 226
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 226

Gly Phe Thr Phe Ser Ser Tyr Trp
1               5

<210> SEQ ID NO 227
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 227

Gly Phe Thr Phe Ser Ser Tyr Ser
1               5
```

<210> SEQ ID NO 228
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 228

Gly Phe Thr Phe Ser Ser Tyr Gly
1               5

<210> SEQ ID NO 229
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 229

Gly Phe Thr Phe Ser Ser Ser Ala
1               5

<210> SEQ ID NO 230
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 230

Gly Phe Thr Phe Asp Asp Tyr Thr
1               5

<210> SEQ ID NO 231
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 231

Gly Phe Thr Phe Asp Asp Tyr Ala
1               5

<210> SEQ ID NO 232
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 232

Gly Phe Thr Phe Ser Ser Tyr Asp
1               5

<210> SEQ ID NO 233
<211> LENGTH: 8
<212> TYPE: PRT
<213> ORGANISM: Artificial
<220> FEATURE:
<223> OTHER INFORMATION: complementary determining region of an antigen
      binder

```
<400> SEQUENCE: 233

Gly Phe Thr Phe Asp Asp Tyr Thr
1               5

<210> SEQ ID NO 234
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 234

Gly Phe Thr Phe Ser Ser Ser Trp
1               5

<210> SEQ ID NO 235
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 235

Ile Ser Thr Asp Gly Gly Ser Thr Ile
1               5

<210> SEQ ID NO 236
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 236

Ile Ser Ser Ser Gly Ser Thr Ile
1               5

<210> SEQ ID NO 237
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 237

Ile Gly Thr Ala Gly Asp Thr
1               5

<210> SEQ ID NO 238
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 238

Ile Ser Gly Ser Gly Gly Ser Thr
1               5

<210> SEQ ID NO 239
<211> LENGTH: 8
<212> TYPE: PRT
```

```
<213> ORGANISM: Artificial
<220> FEATURE:
<223> OTHER INFORMATION: complementary determining region of an antigen
      binder

<400> SEQUENCE: 239

Ile Ser Gly Ser Gly Gly Ser Thr
1               5

<210> SEQ ID NO 240
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 240

Ile Gly Thr Gly Gly Asp Thr
1               5

<210> SEQ ID NO 241
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 241

Ile Ser Ser Asn Gly Gly Ser Thr
1               5

<210> SEQ ID NO 242
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 242

Ile Ser Trp Asp Gly Gly Ser Thr
1               5

<210> SEQ ID NO 243
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 243

Ile Ser Ser Ser Ser Ser Tyr Ile
1               5

<210> SEQ ID NO 244
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 244

Ile Ser Gly Gly Ser Thr
1               5
```

<210> SEQ ID NO 245
<211> LENGTH: 17
<212> TYPE: PRT
<213> ORGANISM: Artificial
<220> FEATURE:
<223> OTHER INFORMATION: complementary determining region of an antigen
      binder

<400> SEQUENCE: 245

Ala Lys Arg Thr Tyr Tyr Asp Phe Trp Arg Thr Tyr Tyr Gly Met Asp
1               5                   10                  15
Val

<210> SEQ ID NO 246
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 246

Ala Arg Thr Tyr Tyr Asp Phe Trp Arg Thr Tyr Tyr Gly Met Asp Val
1               5                   10                  15

<210> SEQ ID NO 247
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 247

Val Lys Thr Tyr Tyr Asp Phe Trp Arg Thr Tyr Tyr Gly Met Asp Val
1               5                   10                  15

<210> SEQ ID NO 248
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 248

Lys Lys Thr Tyr Tyr Asp Phe Trp Arg Thr Tyr Tyr Gly Met Asp Val
1               5                   10                  15

<210> SEQ ID NO 249
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 249

Val Arg Thr Tyr Tyr Asp Phe Trp Arg Thr Tyr Tyr Gly Met Asp Val
1               5                   10                  15

<210> SEQ ID NO 250
<211> LENGTH: 16
<212> TYPE: PRT
<213> ORGANISM: Artificial
<220> FEATURE:

<223> OTHER INFORMATION: complementary determining region of an antigen
      binder

<400> SEQUENCE: 250

Thr Arg Thr Tyr Tyr Asp Phe Trp Arg Thr Tyr Tyr Gly Met Asp Val
1               5                   10                  15

<210> SEQ ID NO 251
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 251

Ser Arg Thr Tyr Tyr Asp Phe Trp Arg Thr Tyr Tyr Gly Met Asp Val
1               5                   10                  15

<210> SEQ ID NO 252
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 252

Ala Thr Thr Tyr Tyr Asp Phe Trp Arg Thr Tyr Tyr Gly Met Asp Val
1               5                   10                  15

<210> SEQ ID NO 253
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 253

Ala Ala Thr Tyr Tyr Asp Phe Trp Arg Thr Tyr Tyr Gly Met Asp Val
1               5                   10                  15

<210> SEQ ID NO 254
<211> LENGTH: 17
<212> TYPE: PRT
<213> ORGANISM: Artificial
<220> FEATURE:
<223> OTHER INFORMATION: complementary determining region of an antigen
      binder

<400> SEQUENCE: 254

Ala Arg Arg Thr Tyr Tyr Asp Phe Trp Arg Thr Tyr Tyr Gly Met Asp
1               5                   10                  15

Val

<210> SEQ ID NO 255
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 255

Gln Asp Ile Ser Ser Trp
1               5

```
<210> SEQ ID NO 256
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 256

Gln Gly Ile Ser Ser Trp
1               5

<210> SEQ ID NO 257
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 257

Gln Gly Ile Ser Ser Ala
1               5

<210> SEQ ID NO 258
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 258

Gln Asp Ile Ser Asn Tyr
1               5

<210> SEQ ID NO 259
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 259

Gln Gly Ile Ser Ser Tyr
1               5

<210> SEQ ID NO 260
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 260

Gln Ser Ile Ser Ser Trp
1               5

<210> SEQ ID NO 261
<211> LENGTH: 6
<212> TYPE: PRT
<213> ORGANISM: Artificial
<220> FEATURE:
<223> OTHER INFORMATION: complementary determining region of an antigen
      binder
```

-continued

```
<400> SEQUENCE: 261

Gln Gly Ile Ser Asn Tyr
1               5

<210> SEQ ID NO 262
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 262

Gln Gly Ile Arg Asn Asp
1               5

<210> SEQ ID NO 263
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 263

Gln Ser Ile Ser Ser Tyr
1               5

<210> SEQ ID NO 264
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 264

Gln Gly Ile Ser Asn Ser
1               5

<210> SEQ ID NO 265
<211> LENGTH: 3
<212> TYPE: PRT
<213> ORGANISM: Artificial
<220> FEATURE:
<223> OTHER INFORMATION: complementary determining region of an antigen
      binder

<400> SEQUENCE: 265

Asp Ala Ser
1

<210> SEQ ID NO 266
<211> LENGTH: 3
<212> TYPE: PRT
<213> ORGANISM: Artificial
<220> FEATURE:
<223> OTHER INFORMATION: complementary determining region of an antigen
      binder

<400> SEQUENCE: 266

Ser Ala Ser
1

<210> SEQ ID NO 267
<211> LENGTH: 3
```

```
<212> TYPE: PRT
<213> ORGANISM: Artificial
<220> FEATURE:
<223> OTHER INFORMATION: complementary determining region of an antigen
      binder

<400> SEQUENCE: 267

Asp Ala Lys
1

<210> SEQ ID NO 268
<211> LENGTH: 3
<212> TYPE: PRT
<213> ORGANISM: Artificial
<220> FEATURE:
<223> OTHER INFORMATION: complementary determining region of an antigen
      binder

<400> SEQUENCE: 268

Tyr Ala Ser
1

<210> SEQ ID NO 269
<211> LENGTH: 4
<212> TYPE: PRT
<213> ORGANISM: Artificial
<220> FEATURE:
<223> OTHER INFORMATION: complementary determining region of an antigen
      binder

<400> SEQUENCE: 269

Tyr Ala Ser Ser
1

<210> SEQ ID NO 270
<211> LENGTH: 5
<212> TYPE: PRT
<213> ORGANISM: Artificial
<220> FEATURE:
<223> OTHER INFORMATION: complementary determining region of an antigen
      binder

<400> SEQUENCE: 270

Tyr Tyr Ala Ser Ser
1               5

<210> SEQ ID NO 271
<211> LENGTH: 3
<212> TYPE: PRT
<213> ORGANISM: Artificial
<220> FEATURE:
<223> OTHER INFORMATION: complementary determining region of an antigen
      binder

<400> SEQUENCE: 271

Asp Ala Lys
1

<210> SEQ ID NO 272
<211> LENGTH: 4
<212> TYPE: PRT
<213> ORGANISM: Artificial
<220> FEATURE:
<223> OTHER INFORMATION: complementary determining region of an antigen
      binder

<400> SEQUENCE: 272

Asp Ala Ser Gly
```

```
<210> SEQ ID NO 273
<211> LENGTH: 4
<212> TYPE: PRT
<213> ORGANISM: Artificial
<220> FEATURE:
<223> OTHER INFORMATION: complementary determining region of an antigen
      binder

<400> SEQUENCE: 273

Gly Asp Ala Ser
1

<210> SEQ ID NO 274
<211> LENGTH: 5
<212> TYPE: PRT
<213> ORGANISM: Artificial
<220> FEATURE:
<223> OTHER INFORMATION: complementary determining region of an antigen
      binder

<400> SEQUENCE: 274

Ser Gly Asp Ala Ser
1               5

<210> SEQ ID NO 275
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 275

Gln Gln Tyr Tyr Ser Thr Pro Tyr Thr
1               5

<210> SEQ ID NO 276
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 276

Gln Gln Tyr Tyr Ser Phe Pro Tyr Thr
1               5

<210> SEQ ID NO 277
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 277

Gln Gln Tyr Tyr Ser Tyr Pro Tyr Thr
1               5

<210> SEQ ID NO 278
<211> LENGTH: 9
<212> TYPE: PRT
<213> ORGANISM: Artificial
<220> FEATURE:
<223> OTHER INFORMATION: complementary determining region of an antigen
```

```
                              binder

<400> SEQUENCE: 278

Gln Gln Tyr Asn Ser Tyr Pro Tyr Thr
1               5

<210> SEQ ID NO 279
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 279

Gln Gln Tyr Tyr Ser Thr Pro Tyr Thr Ser
1               5                   10

<210> SEQ ID NO 280
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 280

Gln Gln Tyr Tyr Ser Thr Pro Tyr Thr Gly
1               5                   10

<210> SEQ ID NO 281
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 281

Ser Gln Gln Tyr Tyr Ser Thr Pro Tyr Thr
1               5                   10

<210> SEQ ID NO 282
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 282

Gly Gln Gln Tyr Tyr Ser Thr Pro Tyr Thr
1               5                   10

<210> SEQ ID NO 283
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 283

Thr Gln Gln Tyr Tyr Ser Thr Pro Tyr Thr
1               5                   10

<210> SEQ ID NO 284
```

```
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 284

Gln Gln Tyr Tyr Ser Thr Pro Tyr Thr Pro
1               5                   10

<210> SEQ ID NO 285
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 285

Gly Phe Ser Phe Ser Asn Tyr Tyr
1               5

<210> SEQ ID NO 286
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 286

Gly Phe Thr Phe Ser Asp Tyr Tyr
1               5

<210> SEQ ID NO 287
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 287

Gly Phe Thr Phe Ser Asn Ala Trp
1               5

<210> SEQ ID NO 288
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 288

Gly Phe Thr Phe Asp Asp Tyr Gly
1               5

<210> SEQ ID NO 289
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 289
```

```
Gly Phe Thr Phe Ser Ser Tyr Ala
1               5

<210> SEQ ID NO 290
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 290

Gly Phe Thr Val Ser Ser Asn Glu
1               5

<210> SEQ ID NO 291
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 291

Gly Phe Thr Val Ser Ser Asn Tyr
1               5

<210> SEQ ID NO 292
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 292

Gly Phe Thr Phe Ser Ser Tyr Ser
1               5

<210> SEQ ID NO 293
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 293

Gly Phe Thr Phe Ser Ser Tyr Gly
1               5

<210> SEQ ID NO 294
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 294

Gly Phe Thr Phe Ser Tyr Tyr Tyr
1               5

<210> SEQ ID NO 295
<211> LENGTH: 8
<212> TYPE: PRT
<213> ORGANISM: Artificial
<220> FEATURE:
```

```
<223> OTHER INFORMATION: complementary determining region of an antigen
      binder

<400> SEQUENCE: 295

Ile Ala Gly Ser Gly Asp Tyr Thr
1               5

<210> SEQ ID NO 296
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 296

Ile Ser Ser Ser Gly Ser Thr Ile
1               5

<210> SEQ ID NO 297
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 297

Val Ser Trp Asn Gly Ser Arg Thr
1               5

<210> SEQ ID NO 298
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 298

Ile Asn Trp Asn Gly Gly Ser Thr
1               5

<210> SEQ ID NO 299
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 299

Ile Ser Ser Ser Ser Ser Tyr Ile
1               5

<210> SEQ ID NO 300
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 300

Ile Ser Gly Ser Gly Gly Ser Thr
1               5
```

```
<210> SEQ ID NO 301
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 301

Ile Ser Tyr Asp Gly Ser Asn Lys
1               5

<210> SEQ ID NO 302
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 302

Ile Trp Tyr Asp Gly Ser Asn Lys
1               5

<210> SEQ ID NO 303
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 303

Ile Ser Trp Asp Gly Gly Ser Thr
1               5

<210> SEQ ID NO 304
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 304

Ile Gly Thr Gly Gly Asp Thr
1               5

<210> SEQ ID NO 305
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 305

Thr Ser Arg Asp Arg Tyr Tyr Thr Met Asp Val
1               5                   10

<210> SEQ ID NO 306
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 306
```

Thr Arg Asp Arg Tyr Tyr Thr Met Asp Val
1               5                   10

<210> SEQ ID NO 307
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 307

Val Arg Asp Arg Tyr Tyr Thr Met Asp Val
1               5                   10

<210> SEQ ID NO 308
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 308

Ala Lys Asp Arg Tyr Tyr Thr Met Asp Val
1               5                   10

<210> SEQ ID NO 309
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 309

Ser Arg Asp Arg Tyr Tyr Thr Met Asp Val
1               5                   10

<210> SEQ ID NO 310
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 310

Thr Thr Asp Arg Tyr Tyr Thr Met Asp Val
1               5                   10

<210> SEQ ID NO 311
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 311

Thr Gly Asp Arg Tyr Tyr Thr Met Asp Val
1               5                   10

<210> SEQ ID NO 312
<211> LENGTH: 11
<212> TYPE: PRT
<213> ORGANISM: Artificial

```
<220> FEATURE:
<223> OTHER INFORMATION: complementary determining region of an antigen
      binder

<400> SEQUENCE: 312

Ala Arg Tyr Asp Arg Tyr Tyr Thr Met Asp Val
1               5                   10

<210> SEQ ID NO 313
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 313

Lys Lys Asp Arg Tyr Tyr Thr Met Asp Val
1               5                   10

<210> SEQ ID NO 314
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 314

Val Lys Asp Arg Tyr Tyr Thr Met Asp Val
1               5                   10

<210> SEQ ID NO 315
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 315

Ser Ser Asp Val Gly Ser Tyr Asp Tyr
1               5

<210> SEQ ID NO 316
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 316

Ser Ser Asp Val Gly Gly Tyr Asn Tyr
1               5

<210> SEQ ID NO 317
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 317

Ser Ser Asp Val Gly Ser Tyr Asn Arg
1               5
```

<210> SEQ ID NO 318
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 318

Ser Ser Asp Val Gly Ser Tyr Asn Leu
1               5

<210> SEQ ID NO 319
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 319

Ser Ser Asp Val Gly Asp Tyr Asp His
1               5

<210> SEQ ID NO 320
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 320

Ser Ser Asp Ile Gly Gly Tyr Asp Leu
1               5

<210> SEQ ID NO 321
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 321

Ser Ser Asp Val Gly Ser Tyr Asp Tyr Gly
1               5                   10

<210> SEQ ID NO 322
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 322

Gly Ser Ser Asp Val Gly Ser Tyr Asp Tyr
1               5                   10

<210> SEQ ID NO 323
<211> LENGTH: 10
<212> TYPE: PRT
<213> ORGANISM: Artificial
<220> FEATURE:
<223> OTHER INFORMATION: complementary determining region of an antigen
      binder

```
<400> SEQUENCE: 323

Val Ser Ser Asp Val Gly Ser Tyr Asp Tyr
1               5                   10

<210> SEQ ID NO 324
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 324

Ser Ser Asp Val Gly Ser Tyr Asp Tyr Val
1               5                   10

<210> SEQ ID NO 325
<211> LENGTH: 3
<212> TYPE: PRT
<213> ORGANISM: Artificial
<220> FEATURE:
<223> OTHER INFORMATION: complementary determining region of an antigen
      binder

<400> SEQUENCE: 325

Asp Val Ser
1

<210> SEQ ID NO 326
<211> LENGTH: 3
<212> TYPE: PRT
<213> ORGANISM: Artificial
<220> FEATURE:
<223> OTHER INFORMATION: complementary determining region of an antigen
      binder

<400> SEQUENCE: 326

Glu Gly Ser
1

<210> SEQ ID NO 327
<211> LENGTH: 3
<212> TYPE: PRT
<213> ORGANISM: Artificial
<220> FEATURE:
<223> OTHER INFORMATION: complementary determining region of an antigen
      binder

<400> SEQUENCE: 327

Asn Val Asn
1

<210> SEQ ID NO 328
<211> LENGTH: 3
<212> TYPE: PRT
<213> ORGANISM: Artificial
<220> FEATURE:
<223> OTHER INFORMATION: complementary determining region of an antigen
      binder

<400> SEQUENCE: 328

Asp Val Ala
1

<210> SEQ ID NO 329
<211> LENGTH: 3
<212> TYPE: PRT
```

```
<213> ORGANISM: Artificial
<220> FEATURE:
<223> OTHER INFORMATION: complementary determining region of an antigen
      binder

<400> SEQUENCE: 329

Asp Val Gly
1

<210> SEQ ID NO 330
<211> LENGTH: 4
<212> TYPE: PRT
<213> ORGANISM: Artificial
<220> FEATURE:
<223> OTHER INFORMATION: complementary determining region of an antigen
      binder

<400> SEQUENCE: 330

Asp Val Ser Gln
1

<210> SEQ ID NO 331
<211> LENGTH: 4
<212> TYPE: PRT
<213> ORGANISM: Artificial
<220> FEATURE:
<223> OTHER INFORMATION: complementary determining region of an antigen
      binder

<400> SEQUENCE: 331

Gln Asp Val Ser
1

<210> SEQ ID NO 332
<211> LENGTH: 4
<212> TYPE: PRT
<213> ORGANISM: Artificial
<220> FEATURE:
<223> OTHER INFORMATION: complementary determining region of an antigen
      binder

<400> SEQUENCE: 332

Gly Asp Val Ser
1

<210> SEQ ID NO 333
<211> LENGTH: 4
<212> TYPE: PRT
<213> ORGANISM: Artificial
<220> FEATURE:
<223> OTHER INFORMATION: complementary determining region of an antigen
      binder

<400> SEQUENCE: 333

Asp Val Ser Asp
1

<210> SEQ ID NO 334
<211> LENGTH: 4
<212> TYPE: PRT
<213> ORGANISM: Artificial
<220> FEATURE:
<223> OTHER INFORMATION: complementary determining region of an antigen
      binder

<400> SEQUENCE: 334

Asp Val Ser Gly
1
```

```
<210> SEQ ID NO 335
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 335

Cys Ser Tyr Asp Ser Ser Leu Ser Gly Ser Leu
1               5                   10

<210> SEQ ID NO 336
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 336

Ser Ser Tyr Asp Ser Ser Leu Ser Gly Ser Leu
1               5                   10

<210> SEQ ID NO 337
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 337

Ser Ser Tyr Asp Ser Ser Leu Ser Gly Ser Leu
1               5                   10

<210> SEQ ID NO 338
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 338

Ser Leu Tyr Asp Ser Ser Leu Ser Gly Ser Leu
1               5                   10

<210> SEQ ID NO 339
<211> LENGTH: 12
<212> TYPE: PRT
<213> ORGANISM: Artificial
<220> FEATURE:
<223> OTHER INFORMATION: complementary determining region of an antigen
      binder

<400> SEQUENCE: 339

Cys Gln Ser Tyr Asp Ser Ser Leu Ser Gly Ser Leu
1               5                   10

<210> SEQ ID NO 340
<211> LENGTH: 12
<212> TYPE: PRT
<213> ORGANISM: Artificial
<220> FEATURE:
<223> OTHER INFORMATION: complementary determining region of an antigen
      binder
```

<400> SEQUENCE: 340

Ser Gln Ser Tyr Asp Ser Ser Leu Ser Gly Ser Leu
1               5                   10

<210> SEQ ID NO 341
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 341

Gln Ser Tyr Asp Ser Ser Asn Ser Gly Ser Leu
1               5                   10

<210> SEQ ID NO 342
<211> LENGTH: 12
<212> TYPE: PRT
<213> ORGANISM: Artificial
<220> FEATURE:
<223> OTHER INFORMATION: complementary determining region of an antigen
      binder

<400> SEQUENCE: 342

Cys Ser Tyr Asp Ser Ser Leu Ser Gly Ser Leu Gly
1               5                   10

<210> SEQ ID NO 343
<211> LENGTH: 12
<212> TYPE: PRT
<213> ORGANISM: Artificial
<220> FEATURE:
<223> OTHER INFORMATION: complementary determining region of an antigen
      binder

<400> SEQUENCE: 343

Cys Ser Tyr Asp Ser Ser Leu Ser Gly Ser Leu Gln
1               5                   10

<210> SEQ ID NO 344
<211> LENGTH: 12
<212> TYPE: PRT
<213> ORGANISM: Artificial
<220> FEATURE:
<223> OTHER INFORMATION: complementary determining region of an antigen
      binder

<400> SEQUENCE: 344

Gly Cys Ser Tyr Asp Ser Ser Leu Ser Gly Ser Leu
1               5                   10

<210> SEQ ID NO 345
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 345

Gly Gly Ser Phe Ser Gly Tyr Trp
1               5

<210> SEQ ID NO 346
<211> LENGTH: 10

```
<212> TYPE: PRT
<213> ORGANISM: Artificial
<220> FEATURE:
<223> OTHER INFORMATION: complementary determining region of an antigen
      binder

<400> SEQUENCE: 346

Gly Gly Ser Ile Ser Ser Gly Gly Tyr Tyr
1               5                   10

<210> SEQ ID NO 347
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 347

Gly Tyr Ser Ile Ser Ser Gly Tyr Tyr
1               5

<210> SEQ ID NO 348
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 348

Gly Gly Ser Ile Ser Ser Tyr Tyr
1               5

<210> SEQ ID NO 349
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 349

Gly Gly Ser Ile Ser Ser Ser Ser Tyr Tyr
1               5                   10

<210> SEQ ID NO 350
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 350

Gly Tyr Ser Phe Thr Ser Tyr Trp
1               5

<210> SEQ ID NO 351
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 351

Gly Gly Ser Val Ser Ser Gly Ser Tyr Tyr
```

```
1               5                   10
```

<210> SEQ ID NO 352
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 352

Gly Phe Thr Phe Ser Ser Tyr Gly
1               5

<210> SEQ ID NO 353
<211> LENGTH: 11
<212> TYPE: PRT
<213> ORGANISM: Artificial
<220> FEATURE:
<223> OTHER INFORMATION: complementary determining region of an antigen
      binder

<400> SEQUENCE: 353

Gly Gly Ser Phe Ser Gly Tyr Tyr Trp Gly Trp
1               5                   10

<210> SEQ ID NO 354
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 354

Val Ser Gly Gly Ser Phe Ser Gly Tyr Tyr
1               5                   10

<210> SEQ ID NO 355
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 355

Ile Asn His Ser Gly Ser Thr Tyr
1               5

<210> SEQ ID NO 356
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 356

Ile Tyr His Ser Gly Ser Thr
1               5

<210> SEQ ID NO 357
<211> LENGTH: 7
<212> TYPE: PRT
<213> ORGANISM: Artificial
<220> FEATURE:
<223> OTHER INFORMATION: complementary determining region of an antigen

```
                            binder

<400> SEQUENCE: 357

Ile Tyr Tyr Ser Gly Ser Thr
1               5

<210> SEQ ID NO 358
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 358

Ile His His Ser Gly Ser Thr
1               5

<210> SEQ ID NO 359
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 359

Ile Tyr Ser Gly Gly Ser Thr
1               5

<210> SEQ ID NO 360
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 360

Gly Tyr Ile Asn His Ser Gly Ser Thr
1               5

<210> SEQ ID NO 361
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 361

Gly Ser Ile Asn His Ser Gly Ser Thr
1               5

<210> SEQ ID NO 362
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 362

Ile Asn His Ser Gly Ser Thr Tyr Tyr
1               5

<210> SEQ ID NO 363
```

```
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 363

Gly Tyr Ile Tyr Tyr Ser Gly Ser Thr
1               5

<210> SEQ ID NO 364
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 364

Gly Tyr Ile Tyr Tyr Ser Gly Ser Thr
1               5

<210> SEQ ID NO 365
<211> LENGTH: 15
<212> TYPE: PRT
<213> ORGANISM: Artificial
<220> FEATURE:
<223> OTHER INFORMATION: complementary determining region of an antigen
      binder

<400> SEQUENCE: 365

Tyr Tyr Cys Ala Arg Leu Pro Met Ile Lys Lys Ser Phe Asp Ile
1               5                   10                  15

<210> SEQ ID NO 366
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 366

Tyr Cys Ala Arg Leu Pro Met Ile Lys Lys Ser Phe Asp Ile
1               5                   10

<210> SEQ ID NO 367
<211> LENGTH: 15
<212> TYPE: PRT
<213> ORGANISM: Artificial
<220> FEATURE:
<223> OTHER INFORMATION: complementary determining region of an antigen
      binder

<400> SEQUENCE: 367

Tyr Cys Cys Ala Arg Leu Pro Met Ile Lys Lys Ser Phe Asp Ile
1               5                   10                  15

<210> SEQ ID NO 368
<211> LENGTH: 17
<212> TYPE: PRT
<213> ORGANISM: Artificial
<220> FEATURE:
<223> OTHER INFORMATION: complementary determining region of an antigen
      binder

<400> SEQUENCE: 368
```

Ala Met Tyr Tyr Cys Ala Arg Leu Pro Met Ile Lys Lys Ser Phe Asp
1               5                   10                  15

Ile

<210> SEQ ID NO 369
<211> LENGTH: 17
<212> TYPE: PRT
<213> ORGANISM: Artificial
<220> FEATURE:
<223> OTHER INFORMATION: complementary determining region of an antigen
      binder

<400> SEQUENCE: 369

Ala Met Tyr Tyr Cys Val Arg Leu Pro Met Ile Lys Lys Ser Phe Asp
1               5                   10                  15

Ile

<210> SEQ ID NO 370
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 370

Tyr Cys Thr Arg Leu Pro Met Ile Lys Lys Ser Phe Asp Ile
1               5                   10

<210> SEQ ID NO 371
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 371

Tyr Cys Met Arg Leu Pro Met Ile Lys Lys Ser Phe Asp Ile
1               5                   10

<210> SEQ ID NO 372
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 372

Tyr Cys Val Lys Leu Pro Met Ile Lys Lys Ser Phe Asp Ile
1               5                   10

<210> SEQ ID NO 373
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 373

Tyr Cys Val Ser Leu Pro Met Ile Lys Lys Ser Phe Asp Ile
1               5                   10

<210> SEQ ID NO 374

```
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 374

Tyr Cys Ala Ser Leu Pro Met Ile Lys Lys Ser Phe Asp Ile
1               5                   10

<210> SEQ ID NO 375
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 375

Gly Phe Thr Phe Thr Ser Tyr Ala
1               5

<210> SEQ ID NO 376
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 376

Gly Phe Thr Phe Thr Gly Tyr Tyr
1               5

<210> SEQ ID NO 377
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 377

Gly Phe Thr Phe Ser Ser Tyr Ser
1               5

<210> SEQ ID NO 378
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 378

Gly Phe Thr Phe Ser Ser Tyr Tyr
1               5

<210> SEQ ID NO 379
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 379
```

```
Gly Phe Thr Phe Ser Ser Tyr Asp
1               5

<210> SEQ ID NO 380
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 380

Gly Phe Thr Phe Ser Tyr Tyr Tyr
1               5

<210> SEQ ID NO 381
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 381

Gly Phe Thr Phe Ser Ser Tyr Gly
1               5

<210> SEQ ID NO 382
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 382

Gln Phe Thr Phe Ser Ser Tyr Tyr
1               5

<210> SEQ ID NO 383
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 383

Gly Phe Thr Phe Asp Asp Tyr Gly
1               5

<210> SEQ ID NO 384
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 384

Gly Phe Thr Phe Ser Asn Ser Asp
1               5

<210> SEQ ID NO 385
<211> LENGTH: 7
<212> TYPE: PRT
<213> ORGANISM: Artificial
<220> FEATURE:
```

<223> OTHER INFORMATION: complementary determining region of an antigen
      binder

<400> SEQUENCE: 385

Ile Tyr His Asp Gly Thr Thr
1               5

<210> SEQ ID NO 386
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 386

Ile Ser Gly Ser Gly Gly Ser Thr
1               5

<210> SEQ ID NO 387
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 387

Ile Ser Gly Gly Ser Thr
1               5

<210> SEQ ID NO 388
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 388

Ile Tyr Ser Gly Gly Ser Thr
1               5

<210> SEQ ID NO 389
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 389

Ile Ser Tyr Asp Gly Ser Asn Lys
1               5

<210> SEQ ID NO 390
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 390

Ile Tyr His Ser Gly Ser Thr
1               5

```
<210> SEQ ID NO 391
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 391

Ile Tyr Tyr Ser Gly Ser Thr
1               5

<210> SEQ ID NO 392
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 392

Ile His His Ser Gly Ser Thr
1               5

<210> SEQ ID NO 393
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 393

Ile Asn His Ser Gly Ser Thr
1               5

<210> SEQ ID NO 394
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 394

Ile Trp Tyr Asp Gly Ser Asn Lys
1               5

<210> SEQ ID NO 395
<211> LENGTH: 14
<212> TYPE: PRT
<213> ORGANISM: Artificial
<220> FEATURE:
<223> OTHER INFORMATION: complementary determining region of an antigen
      binder

<400> SEQUENCE: 395

Tyr Ala Arg Val Trp Leu Tyr Gly Ser Gly Tyr Met Asp Val
1               5                   10

<210> SEQ ID NO 396
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 396
```

Tyr Tyr Tyr Ala Arg Val Trp Leu Tyr Gly Ser Gly Tyr Met Asp Val
1               5                   10                  15

<210> SEQ ID NO 397
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 397

Tyr Tyr Trp Ala Arg Val Trp Leu Tyr Gly Ser Gly Tyr Met Asp Val
1               5                   10                  15

<210> SEQ ID NO 398
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 398

Tyr Tyr Cys Val Arg Val Trp Leu Tyr Gly Ser Gly Tyr Met Asp Val
1               5                   10                  15

<210> SEQ ID NO 399
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 399

Tyr Tyr Cys Thr Arg Val Trp Leu Tyr Gly Ser Gly Tyr Met Asp Val
1               5                   10                  15

<210> SEQ ID NO 400
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 400

Tyr Tyr Cys Met Arg Val Trp Leu Tyr Gly Ser Gly Tyr Met Asp Val
1               5                   10                  15

<210> SEQ ID NO 401
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 401

Tyr Tyr Cys Ala Thr Val Trp Leu Tyr Gly Ser Gly Tyr Met Asp Val
1               5                   10                  15

<210> SEQ ID NO 402
<211> LENGTH: 16
<212> TYPE: PRT
<213> ORGANISM: Artificial

```
<220> FEATURE:
<223> OTHER INFORMATION: complementary determining region of an antigen
      binder

<400> SEQUENCE: 402

Tyr Tyr Cys Ala Lys Val Trp Leu Tyr Gly Ser Gly Tyr Met Asp Val
1               5                   10                  15

<210> SEQ ID NO 403
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 403

Tyr Tyr Cys Ala Ser Val Trp Leu Tyr Gly Ser Gly Tyr Met Asp Val
1               5                   10                  15

<210> SEQ ID NO 404
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 404

Tyr Tyr Cys Ser Arg Val Trp Leu Tyr Gly Ser Gly Tyr Met Asp Val
1               5                   10                  15

<210> SEQ ID NO 405
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 405

Ala Phe Asp Phe Tyr Asp Tyr Glu Met Ser
1               5                   10

<210> SEQ ID NO 406
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 406

Phe Asp Phe Tyr Asp Tyr Glu Met Ser
1               5

<210> SEQ ID NO 407
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 407

Asp Phe Tyr Asp Tyr Glu Met Ser
1               5
```

```
<210> SEQ ID NO 408
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 408

Phe Tyr Asp Tyr Glu Met Ser
1               5

<210> SEQ ID NO 409
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 409

Tyr Asp Tyr Glu Met Ser
1               5

<210> SEQ ID NO 410
<211> LENGTH: 5
<212> TYPE: PRT
<213> ORGANISM: Artificial
<220> FEATURE:
<223> OTHER INFORMATION: complementary determining region of an antigen
      binder

<400> SEQUENCE: 410

Asp Tyr Glu Met His
1               5

<210> SEQ ID NO 411
<211> LENGTH: 5
<212> TYPE: PRT
<213> ORGANISM: Artificial
<220> FEATURE:
<223> OTHER INFORMATION: complementary determining region of an antigen
      binder

<400> SEQUENCE: 411

Asp Tyr Glu Met Gly
1               5

<210> SEQ ID NO 412
<211> LENGTH: 5
<212> TYPE: PRT
<213> ORGANISM: Artificial
<220> FEATURE:
<223> OTHER INFORMATION: complementary determining region of an antigen
      binder

<400> SEQUENCE: 412

Asp Tyr Ala Met Ser
1               5

<210> SEQ ID NO 413
<211> LENGTH: 5
<212> TYPE: PRT
<213> ORGANISM: Artificial
<220> FEATURE:
<223> OTHER INFORMATION: complementary determining region of an antigen
      binder
```

```
<400> SEQUENCE: 413

Asp Tyr Gly Met Ser
1               5

<210> SEQ ID NO 414
<211> LENGTH: 5
<212> TYPE: PRT
<213> ORGANISM: Artificial
<220> FEATURE:
<223> OTHER INFORMATION: complementary determining region of an antigen
      binder

<400> SEQUENCE: 414

Asp Tyr Tyr Met Ser
1               5

<210> SEQ ID NO 415
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 415

Glu Ile His His Ser Gly Ser Thr Tyr Tyr Asn Pro Ser Leu Lys Ser
1               5                   10                  15

<210> SEQ ID NO 416
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 416

Ser Ile His His Ser Gly Ser Thr Tyr Tyr Asn Pro Ser Leu Lys Gly
1               5                   10                  15

<210> SEQ ID NO 417
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 417

Glu Ile His His Ser Gly Ser Thr Asn Tyr Asn Pro Ser Leu Lys Gly
1               5                   10                  15

<210> SEQ ID NO 418
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 418

Tyr Ile His His Ser Gly Ser Thr Tyr Tyr Asn Pro Ser Leu Lys Gly
1               5                   10                  15

<210> SEQ ID NO 419
<211> LENGTH: 16
<212> TYPE: PRT
```

<213> ORGANISM: Artificial
<220> FEATURE:
<223> OTHER INFORMATION: complementary determining region of an antigen
      binder

<400> SEQUENCE: 419

Tyr Ile His His Ser Gly Ser Thr Tyr Tyr Asn Pro Ser Leu Lys Ser
1               5                   10                  15

<210> SEQ ID NO 420
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 420

Glu Ile Asn His Ser Gly Ser Thr Tyr Tyr Asn Pro Ser Leu Lys Gly
1               5                   10                  15

<210> SEQ ID NO 421
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 421

Glu Ile His Tyr Ser Gly Ser Thr Tyr Tyr Asn Pro Ser Leu Lys Gly
1               5                   10                  15

<210> SEQ ID NO 422
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 422

Tyr Ile Tyr Tyr Ser Gly Ser Thr Tyr Tyr Asn Pro Ser Leu Lys Gly
1               5                   10                  15

<210> SEQ ID NO 423
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 423

Glu Ile His Tyr Ser Gly Ser Thr Tyr Tyr Asn Pro Ser Leu Lys Ser
1               5                   10                  15

<210> SEQ ID NO 424
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 424

Glu Ile Asn His Ser Gly Ser Thr Tyr Tyr Asn Pro Ser Leu Lys Ser
1               5                   10                  15

<210> SEQ ID NO 425
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 425

Ser Asp Val Ser Tyr His Ala Asp Val
1               5

<210> SEQ ID NO 426
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 426

Lys Asp Val Ser Tyr His Ala Asp Val
1               5

<210> SEQ ID NO 427
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 427

Ala Lys Asp Val Ser Tyr His Ala Asp Val
1               5                   10

<210> SEQ ID NO 428
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 428

Val Lys Asp Val Ser Tyr His Ala Asp Val
1               5                   10

<210> SEQ ID NO 429
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 429

Ala Arg Asp Val Ser Tyr His Ala Asp Val
1               5                   10

<210> SEQ ID NO 430
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 430

Thr Arg Asp Val Ser Tyr His Ala Asp Val
1               5                   10

<210> SEQ ID NO 431
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 431

Met Arg Asp Val Ser Tyr His Ala Asp Val
1               5                   10

<210> SEQ ID NO 432
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 432

Ser Arg Asp Val Ser Tyr His Ala Asp Val
1               5                   10

<210> SEQ ID NO 433
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 433

Ala Thr Asp Val Ser Tyr His Ala Asp Val
1               5                   10

<210> SEQ ID NO 434
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 434

Thr Thr Asp Val Ser Tyr His Ala Asp Val
1               5                   10

<210> SEQ ID NO 435
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 435

Gly Phe Thr Phe Asp Asp Tyr Ala Met Ser
1               5                   10

<210> SEQ ID NO 436
<211> LENGTH: 9

```
<212> TYPE: PRT
<213> ORGANISM: Artificial
<220> FEATURE:
<223> OTHER INFORMATION: complementary determining region of an antigen
      binder

<400> SEQUENCE: 436

Phe Thr Phe Asp Asp Tyr Ala Met Ser
1               5

<210> SEQ ID NO 437
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 437

Thr Phe Asp Asp Tyr Ala Met Ser
1               5

<210> SEQ ID NO 438
<211> LENGTH: 7
<212> TYPE: PRT
<213> ORGANISM: Artificial
<220> FEATURE:
<223> OTHER INFORMATION: complementary determining region of an antigen
      binder

<400> SEQUENCE: 438

Phe Asp Asp Tyr Ala Met Ser
1               5

<210> SEQ ID NO 439
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 439

Asp Asp Tyr Ala Met Ser
1               5

<210> SEQ ID NO 440
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 440

Asp Asp Tyr Glu Met Ser
1               5

<210> SEQ ID NO 441
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 441

Asp Asp Tyr Ala Met His
```

```
1               5
```

<210> SEQ ID NO 442
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 442

```
Asp Asp Tyr Ala Met Gly
1               5
```

<210> SEQ ID NO 443
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 443

```
Asp Glu Tyr Ala Met Ser
1               5
```

<210> SEQ ID NO 444
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 444

```
Asp Asp Tyr Tyr Met Ser
1               5
```

<210> SEQ ID NO 445
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 445

```
Arg Met Tyr Asn Asn Gly Arg Thr Ser Tyr Asn Pro Ser Leu Lys Gly
1               5                   10                  15
```

<210> SEQ ID NO 446
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 446

```
Arg Met Tyr Asn Asn Gly Arg Thr Ser Tyr Asn Pro Ser Leu Lys Ser
1               5                   10                  15
```

<210> SEQ ID NO 447
<211> LENGTH: 16
<212> TYPE: PRT
<213> ORGANISM: Artificial
<220> FEATURE:
<223> OTHER INFORMATION: complementary determining region of an antigen

```
                       binder

<400> SEQUENCE: 447

Arg Met Tyr Asn Asn Gly Arg Thr Tyr Tyr Asn Pro Ser Leu Lys Ser
1               5                   10                  15

<210> SEQ ID NO 448
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 448

Lys Met Tyr Asn Asn Gly Arg Thr Ser Tyr Asn Pro Ser Leu Lys Ser
1               5                   10                  15

<210> SEQ ID NO 449
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 449

Arg Met Tyr Asn Asn Ala Arg Thr Ser Tyr Asn Pro Ser Leu Lys Ser
1               5                   10                  15

<210> SEQ ID NO 450
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 450

Arg Met Tyr Asn Asn Ser Arg Thr Ser Tyr Asn Pro Ser Leu Lys Ser
1               5                   10                  15

<210> SEQ ID NO 451
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 451

Arg Met Tyr Asn Asn Ser Arg Thr Ser Tyr Asn Pro Ser Leu Lys Gly
1               5                   10                  15

<210> SEQ ID NO 452
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 452

Lys Met Tyr Asn Asn Gly Arg Thr Ser Tyr Asn Pro Ser Leu Lys Gly
1               5                   10                  15

<210> SEQ ID NO 453
```

```
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 453

Arg Met Tyr Asn Asn Ala Arg Thr Ser Tyr Asn Pro Ser Leu Lys Gly
1               5                   10                  15

<210> SEQ ID NO 454
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 454

Ile Gly Arg Met Tyr Asn Asn Ala Arg Thr Ser Tyr Asn Pro Ser Leu
1               5                   10                  15

Lys Gly

<210> SEQ ID NO 455
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 455

Ile Thr Asp Asn Leu Gly Tyr Arg Pro Ser Glu Asn Leu Tyr Gly Met
1               5                   10                  15

Asp Val

<210> SEQ ID NO 456
<211> LENGTH: 17
<212> TYPE: PRT
<213> ORGANISM: Artificial
<220> FEATURE:
<223> OTHER INFORMATION: complementary determining region of an antigen
      binder

<400> SEQUENCE: 456

Arg Asp Asn Leu Gly Tyr Arg Pro Ser Glu Asn Leu Tyr Gly Met Asp
1               5                   10                  15

Val

<210> SEQ ID NO 457
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 457

Ala Arg Asp Asn Leu Gly Tyr Arg Pro Ser Glu Asn Leu Tyr Gly Met
1               5                   10                  15

Asp Val

<210> SEQ ID NO 458
<211> LENGTH: 18
```

```
<212> TYPE: PRT
<213> ORGANISM: Artificial
<220> FEATURE:
<223> OTHER INFORMATION: complementary determining region of an antigen
      binder

<400> SEQUENCE: 458

Ala Lys Asp Asn Leu Gly Tyr Arg Pro Ser Glu Asn Leu Tyr Gly Met
1               5                   10                  15
Asp Val

<210> SEQ ID NO 459
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 459

Ala Thr Asp Asn Leu Gly Tyr Arg Pro Ser Glu Asn Leu Tyr Gly Met
1               5                   10                  15
Asp Val

<210> SEQ ID NO 460
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 460

Thr Thr Asp Asn Leu Gly Tyr Arg Pro Ser Glu Asn Leu Tyr Gly Met
1               5                   10                  15
Asp Val

<210> SEQ ID NO 461
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 461

Ile Arg Asp Asn Leu Gly Tyr Arg Pro Ser Glu Asn Leu Tyr Gly Met
1               5                   10                  15
Asp Val

<210> SEQ ID NO 462
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 462

Val Arg Asp Asn Leu Gly Tyr Arg Pro Ser Glu Asn Leu Tyr Gly Met
1               5                   10                  15
Asp Val

<210> SEQ ID NO 463
```

<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 463

Thr Arg Asp Asn Leu Gly Tyr Arg Pro Ser Glu Asn Leu Tyr Gly Met
1               5                   10                  15

Asp Val

<210> SEQ ID NO 464
<211> LENGTH: 18
<212> TYPE: PRT
<213> ORGANISM: Artificial
<220> FEATURE:
<223> OTHER INFORMATION: complementary determining region of an antigen
      binder

<400> SEQUENCE: 464

Met Arg Asp Asn Leu Gly Tyr Arg Pro Ser Glu Asn Leu Tyr Gly Met
1               5                   10                  15

Asp Val

<210> SEQ ID NO 465
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 465

Gly Phe Thr Leu Ser Asp Tyr Tyr Ile Gly
1               5                   10

<210> SEQ ID NO 466
<211> LENGTH: 9
<212> TYPE: PRT
<213> ORGANISM: Artificial
<220> FEATURE:
<223> OTHER INFORMATION: complementary determining region of an antigen
      binder

<400> SEQUENCE: 466

Phe Thr Leu Ser Asp Tyr Tyr Ile Gly
1               5

<210> SEQ ID NO 467
<211> LENGTH: 8
<212> TYPE: PRT
<213> ORGANISM: Artificial
<220> FEATURE:
<223> OTHER INFORMATION: complementary determining region of an antigen
      binder

<400> SEQUENCE: 467

Thr Leu Ser Asp Tyr Tyr Ile Gly
1               5

<210> SEQ ID NO 468
<211> LENGTH: 7
<212> TYPE: PRT
<213> ORGANISM: Artificial
<220> FEATURE:
<223> OTHER INFORMATION: complementary determining region of an antigen binder

<400> SEQUENCE: 468

Leu Ser Asp Tyr Tyr Ile Gly
1               5

<210> SEQ ID NO 469
<211> LENGTH: 6
<212> TYPE: PRT
<213> ORGANISM: Artificial
<220> FEATURE:
<223> OTHER INFORMATION: complementary determining region of an antigen
      binder

<400> SEQUENCE: 469

Ser Asp Tyr Tyr Ile Gly
1               5

<210> SEQ ID NO 470
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 470

Gly Phe Thr Phe Ser Asp Tyr Tyr Ile Gly
1               5                   10

<210> SEQ ID NO 471
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 471

Gly Phe Thr Phe Ser Asp Tyr Tyr Glu Gly
1               5                   10

<210> SEQ ID NO 472
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 472

Gly Phe Thr Phe Ser Asp Tyr Tyr Ile Ser
1               5                   10

<210> SEQ ID NO 473
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 473

Gly Leu Thr Phe Ser Asp Tyr Tyr Ile Gly
1               5                   10

<210> SEQ ID NO 474

```
<211> LENGTH: 10
<212> TYPE: PRT
<213> ORGANISM: Artificial
<220> FEATURE:
<223> OTHER INFORMATION: complementary determining region of an antigen
      binder

<400> SEQUENCE: 474

Gly Phe Thr Phe Ser Asp Tyr Tyr Ile Ser
1               5                   10

<210> SEQ ID NO 475
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 475

Ser Met Tyr His Ser Gly Arg Thr Tyr Ile Asn Pro Ser Leu Lys Gly
1               5                   10                  15

<210> SEQ ID NO 476
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 476

Ser Met Tyr His Ser Gly Arg Thr Tyr Val Asn Pro Ser Leu Lys Ser
1               5                   10                  15

<210> SEQ ID NO 477
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 477

Ser Met Tyr His Ser Gly Arg Thr Tyr Val Asn Pro Ser Leu Lys Gly
1               5                   10                  15

<210> SEQ ID NO 478
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 478

Gly Met Tyr His Ser Gly Arg Thr Tyr Val Asn Pro Ser Leu Lys Ser
1               5                   10                  15

<210> SEQ ID NO 479
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 479
```

```
Ser Met Tyr His Ser Gly Arg Ser Tyr Val Asn Pro Ser Leu Lys Ser
1               5                   10                  15
```

<210> SEQ ID NO 480
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 480

```
Ser Met Tyr His Ser Gly Arg Ser Tyr Val Asn Pro Ser Leu Lys Gly
1               5                   10                  15
```

<210> SEQ ID NO 481
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 481

```
Gly Met Tyr His Ser Gly Arg Ser Tyr Val Asn Pro Ser Leu Lys Ser
1               5                   10                  15
```

<210> SEQ ID NO 482
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 482

```
Gly Met Tyr His Ser Gly Arg Ser Tyr Val Asn Pro Ser Leu Lys Gly
1               5                   10                  15
```

<210> SEQ ID NO 483
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 483

```
Ser Met Tyr His Ser Gly Lys Ser Tyr Val Asn Pro Ser Leu Lys Ser
1               5                   10                  15
```

<210> SEQ ID NO 484
<211> LENGTH: 16
<212> TYPE: PRT
<213> ORGANISM: Artificial
<220> FEATURE:
<223> OTHER INFORMATION: complementary determining region of an antigen
      binder

<400> SEQUENCE: 484

```
Ser Met Tyr His Ser Gly Lys Ser Tyr Val Asn Pro Ser Leu Lys Gly
1               5                   10                  15
```

<210> SEQ ID NO 485
<211> LENGTH: 13
<212> TYPE: PRT
<213> ORGANISM: Artificial
<220> FEATURE:

<223> OTHER INFORMATION: complementary determining region of an antigen
      binder

<400> SEQUENCE: 485

Ala Arg Gly Gly Ile Thr Gly Thr Thr Pro Ile Asp Tyr
1               5                   10

<210> SEQ ID NO 486
<211> LENGTH: 12
<212> TYPE: PRT
<213> ORGANISM: Artificial
<220> FEATURE:
<223> OTHER INFORMATION: complementary determining region of an antigen
      binder

<400> SEQUENCE: 486

Arg Gly Gly Ile Thr Gly Thr Thr Pro Ile Asp Tyr
1               5                   10

<210> SEQ ID NO 487
<211> LENGTH: 13
<212> TYPE: PRT
<213> ORGANISM: Artificial
<220> FEATURE:
<223> OTHER INFORMATION: complementary determining region of an antigen
      binder

<400> SEQUENCE: 487

Thr Arg Gly Gly Ile Thr Gly Thr Thr Pro Ile Asp Tyr
1               5                   10

<210> SEQ ID NO 488
<211> LENGTH: 13
<212> TYPE: PRT
<213> ORGANISM: Artificial
<220> FEATURE:
<223> OTHER INFORMATION: complementary determining region of an antigen
      binder

<400> SEQUENCE: 488

Val Arg Gly Gly Ile Thr Gly Thr Thr Pro Ile Asp Tyr
1               5                   10

<210> SEQ ID NO 489
<211> LENGTH: 13
<212> TYPE: PRT
<213> ORGANISM: Artificial
<220> FEATURE:
<223> OTHER INFORMATION: complementary determining region of an antigen
      binder

<400> SEQUENCE: 489

Met Arg Gly Gly Ile Thr Gly Thr Thr Pro Ile Asp Tyr
1               5                   10

<210> SEQ ID NO 490
<211> LENGTH: 13
<212> TYPE: PRT
<213> ORGANISM: Artificial
<220> FEATURE:
<223> OTHER INFORMATION: complementary determining region of an antigen
      binder

<400> SEQUENCE: 490

Ala Lys Gly Gly Ile Thr Gly Thr Thr Pro Ile Asp Tyr
1               5                   10

<210> SEQ ID NO 491
<211> LENGTH: 13
<212> TYPE: PRT
<213> ORGANISM: Artificial
<220> FEATURE:
<223> OTHER INFORMATION: complementary determining region of an antigen binder

<400> SEQUENCE: 491

Ala Thr Gly Gly Ile Thr Gly Thr Thr Pro Ile Asp Tyr
1 5 10

<210> SEQ ID NO 492
<211> LENGTH: 13
<212> TYPE: PRT
<213> ORGANISM: Artificial
<220> FEATURE:
<223> OTHER INFORMATION: complementary determining region of an antigen binder

<400> SEQUENCE: 492

Thr Thr Gly Gly Ile Thr Gly Thr Thr Pro Ile Asp Tyr
1 5 10

<210> SEQ ID NO 493
<211> LENGTH: 13
<212> TYPE: PRT
<213> ORGANISM: Artificial
<220> FEATURE:
<223> OTHER INFORMATION: complementary determining region of an antigen binder

<400> SEQUENCE: 493

Ala Gly Gly Gly Ile Thr Gly Thr Thr Pro Ile Asp Tyr
1 5 10

<210> SEQ ID NO 494
<211> LENGTH: 13
<212> TYPE: PRT
<213> ORGANISM: Artificial
<220> FEATURE:
<223> OTHER INFORMATION: complementary determining region of an antigen binder

<400> SEQUENCE: 494

Ile Arg Gly Gly Ile Thr Gly Thr Thr Pro Ile Asp Tyr
1 5 10

<210> SEQ ID NO 495
<211> LENGTH: 1273
<212> TYPE: PRT
<213> ORGANISM: Coronavirus

<400> SEQUENCE: 495

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu

```
                     85                  90                  95
Lys Ser Asn Ile Ile Arg Gly Trp Ile Phe Gly Thr Thr Leu Asp Ser
                100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
        130                 135                 140

Tyr His Lys Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510
```

```
Leu Ser Phe Glu Leu Leu His Ala Pro Ala Thr Val Cys Gly Pro Lys
            515                 520                 525
Lys Ser Thr Asn Leu Val Lys Asn Lys Cys Val Asn Phe Asn Phe Asn
        530                 535                 540
Gly Leu Thr Gly Thr Gly Val Leu Thr Glu Ser Asn Lys Lys Phe Leu
545                 550                 555                 560
Pro Phe Gln Gln Phe Gly Arg Asp Ile Ala Asp Thr Thr Asp Ala Val
                565                 570                 575
Arg Asp Pro Gln Thr Leu Glu Ile Leu Asp Ile Thr Pro Cys Ser Phe
            580                 585                 590
Gly Gly Val Ser Val Ile Thr Pro Gly Thr Asn Thr Ser Asn Gln Val
        595                 600                 605
Ala Val Leu Tyr Gln Asp Val Asn Cys Thr Glu Val Pro Val Ala Ile
    610                 615                 620
His Ala Asp Gln Leu Thr Pro Thr Trp Arg Val Tyr Ser Thr Gly Ser
625                 630                 635                 640
Asn Val Phe Gln Thr Arg Ala Gly Cys Leu Ile Gly Ala Glu His Val
                645                 650                 655
Asn Asn Ser Tyr Glu Cys Asp Ile Pro Ile Gly Ala Gly Ile Cys Ala
            660                 665                 670
Ser Tyr Gln Thr Gln Thr Asn Ser Pro Arg Arg Ala Arg Ser Val Ala
        675                 680                 685
Ser Gln Ser Ile Ile Ala Tyr Thr Met Ser Leu Gly Ala Glu Asn Ser
    690                 695                 700
Val Ala Tyr Ser Asn Asn Ser Ile Ala Ile Pro Thr Asn Phe Thr Ile
705                 710                 715                 720
Ser Val Thr Thr Glu Ile Leu Pro Val Ser Met Thr Lys Thr Ser Val
                725                 730                 735
Asp Cys Thr Met Tyr Ile Cys Gly Asp Ser Thr Glu Cys Ser Asn Leu
            740                 745                 750
Leu Leu Gln Tyr Gly Ser Phe Cys Thr Gln Leu Asn Arg Ala Leu Thr
        755                 760                 765
Gly Ile Ala Val Glu Gln Asp Lys Asn Thr Gln Glu Val Phe Ala Gln
    770                 775                 780
Val Lys Gln Ile Tyr Lys Thr Pro Pro Ile Lys Asp Phe Gly Gly Phe
785                 790                 795                 800
Asn Phe Ser Gln Ile Leu Pro Asp Pro Ser Lys Pro Ser Lys Arg Ser
                805                 810                 815
Phe Ile Glu Asp Leu Leu Phe Asn Lys Val Thr Leu Ala Asp Ala Gly
            820                 825                 830
Phe Ile Lys Gln Tyr Gly Asp Cys Leu Gly Asp Ile Ala Ala Arg Asp
        835                 840                 845
Leu Ile Cys Ala Gln Lys Phe Asn Gly Leu Thr Val Leu Pro Pro Leu
    850                 855                 860
Leu Thr Asp Glu Met Ile Ala Gln Tyr Thr Ser Ala Leu Leu Ala Gly
865                 870                 875                 880
Thr Ile Thr Ser Gly Trp Thr Phe Gly Ala Gly Ala Ala Leu Gln Ile
                885                 890                 895
Pro Phe Ala Met Gln Met Ala Tyr Arg Phe Asn Gly Ile Gly Val Thr
            900                 905                 910
Gln Asn Val Leu Tyr Glu Asn Gln Lys Leu Ile Ala Asn Gln Phe Asn
        915                 920                 925
```

Ser Ala Ile Gly Lys Ile Gln Asp Ser Leu Ser Ser Thr Ala Ser Ala
    930                 935                 940

Leu Gly Lys Leu Gln Asp Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270

<210> SEQ ID NO 496
<211> LENGTH: 203
<212> TYPE: PRT
<213> ORGANISM: Coronavirus

<400> SEQUENCE: 496

Pro Asn Ile Thr Asn Leu Cys Pro Phe Gly Glu Val Phe Asn Ala Thr
1               5                   10                  15

```
Arg Phe Ala Ser Val Tyr Ala Trp Asn Arg Lys Arg Ile Ser Asn Cys
            20                  25                  30

Val Ala Asp Tyr Ser Val Leu Tyr Asn Ser Ala Ser Phe Ser Thr Phe
        35                  40                  45

Lys Cys Tyr Gly Val Ser Pro Thr Lys Leu Asn Asp Leu Cys Phe Thr
    50                  55                  60

Asn Val Tyr Ala Asp Ser Phe Val Ile Arg Gly Asp Glu Val Arg Gln
65                  70                  75                  80

Ile Ala Pro Gly Gln Thr Gly Lys Ile Ala Asp Tyr Asn Tyr Lys Leu
                85                  90                  95

Pro Asp Asp Phe Thr Gly Cys Val Ile Ala Trp Asn Ser Asn Asn Leu
            100                 105                 110

Asp Ser Lys Val Gly Gly Asn Tyr Asn Tyr Leu Tyr Arg Leu Phe Arg
        115                 120                 125

Lys Ser Asn Leu Lys Pro Phe Glu Arg Asp Ile Ser Thr Glu Ile Tyr
    130                 135                 140

Gln Ala Gly Ser Thr Pro Cys Asn Gly Val Glu Gly Phe Asn Cys Tyr
145                 150                 155                 160

Phe Pro Leu Gln Ser Tyr Gly Phe Gln Pro Thr Asn Gly Val Gly Tyr
                165                 170                 175

Gln Pro Tyr Arg Val Val Val Leu Ser Phe Glu Leu Leu His Ala Pro
            180                 185                 190

Ala Thr Val Cys Gly Pro Lys Lys Ser Thr Asn
        195                 200

<210> SEQ ID NO 497
<211> LENGTH: 103
<212> TYPE: PRT
<213> ORGANISM: Artificial
<220> FEATURE:
<223> OTHER INFORMATION: heavy chain constant domain

<400> SEQUENCE: 497

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 498
<211> LENGTH: 107
<212> TYPE: PRT
<213> ORGANISM: Artificial
<220> FEATURE:
<223> OTHER INFORMATION: light chain constant domain

<400> SEQUENCE: 498

Arg Thr Val Ala Ala Pro Ser Val Phe Ile Phe Pro Pro Ser Asp Glu
```

```
              1               5                   10                  15
Gln Leu Lys Ser Gly Thr Ala Ser Val Val Cys Leu Leu Asn Asn Phe
              20                  25                  30

Tyr Pro Arg Glu Ala Lys Val Gln Trp Lys Val Asp Asn Ala Leu Gln
              35                  40                  45

Ser Gly Asn Ser Gln Glu Ser Val Thr Glu Gln Asp Ser Lys Asp Ser
              50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
              85                  90                  95

Pro Val Thr Lys Ser Phe Asn Arg Gly Glu Cys
              100                 105
```

<210> SEQ ID NO 499
<211> LENGTH: 107
<212> TYPE: PRT
<213> ORGANISM: Artificial
<220> FEATURE:
<223> OTHER INFORMATION: heavy chain constant domain

<400> SEQUENCE: 499

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
              20                  25                  30

Phe Pro Glu Pro Val Thr Val Ser Trp Asn Ser Gly Ala Leu Thr Ser
              35                  40                  45

Gly Val His Thr Phe Pro Ala Val Leu Gln Ser Ser Gly Leu Tyr Ser
              50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
              85                  90                  95

Lys Val Glu Pro Lys Ser Cys Asp Lys Thr Ser
              100                 105
```

<210> SEQ ID NO 500
<211> LENGTH: 105
<212> TYPE: PRT
<213> ORGANISM: Artificial
<220> FEATURE:
<223> OTHER INFORMATION: light chain constant domain

<400> SEQUENCE: 500

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
              20                  25                  30

Tyr Pro Gly Ala Val Thr Val Ala Trp Lys Ala Asp Ser Ser Pro Val
              35                  40                  45

Lys Ala Gly Val Glu Thr Thr Thr Pro Ser Lys Gln Ser Asn Asn Lys
              50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
              85                  90                  95
```

Lys Thr Val Ala Pro Thr Glu Cys Ser
                100                 105

<210> SEQ ID NO 501
<211> LENGTH: 660
<212> TYPE: DNA
<213> ORGANISM: Artificial
<220> FEATURE:
<223> OTHER INFORMATION: heavy chain region/domain

<400> SEQUENCE: 501

```
gaggtgcagc tggtggagtc tggaggaggc ttggtccagc ctggggggtc cctgagactc      60
tcctgtgcag cctctgggtt caccgtcagt agcaactaca tgagctgggt ccgccaggct     120
ccagggaagg gctggagtg gtctcagtt atttatagcg gtggtagcac atactacgca       180
gactccgtga aggccgatt caccatctcc agacacaatt ccaagaacac gctgtatctt     240
caaatgaaca gcctgagagc tgaggacacg gccgtgtatt actgtgcgag ggggtacggt     300
gactactact ttgactactg gggccaggga accctggtca ccgtctcctc agcctccacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660
```

<210> SEQ ID NO 502
<211> LENGTH: 642
<212> TYPE: DNA
<213> ORGANISM: Artificial
<220> FEATURE:
<223> OTHER INFORMATION: light chain region/domain

<400> SEQUENCE: 502

```
gatgttgtga tgactcagtc tccagccacc ctgtctttgt ctccagggga aaaagccacc      60
ctctcctgca gggccagtca gagtgttagc agctacttag cctggtacca gcagaaacca    120
ggacagcctc ctaagctgct catttactgg gcatctaccc gggaatccgg ggtccctgac    180
cgattcagtg gcagcgggtc tgggacagat ttcactctca ccatcagcag cctgcaggct    240
gaagatgtgg cagtttatta ctgtcagcag tatggtagct cacctctcac tttcggcgga    300
gggaccaagg tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                        642
```

<210> SEQ ID NO 503
<211> LENGTH: 693
<212> TYPE: DNA
<213> ORGANISM: Artificial
<220> FEATURE:
<223> OTHER INFORMATION: heavy chain region/domain

<400> SEQUENCE: 503

```
caggtacagc tgcagcagtc aggtccagga ctggtgaagc cctcgcagac cctctcactc      60
```

| | | |
|---|---|---|
| acctgtgcca tctccgggga cagtgtctct agcaacagtg ctgcttggaa ctggatcagg | 120 | |
| cagtccccat cgagaggcct tgagtggctg ggaaggacat actacaggtc caagtggtat | 180 | |
| aatgattatg cagtatctgt gaaaagtcga ataaccatca acccagacac atccaagaac | 240 | |
| cagttctccc tgcagctgaa ctctgtgact cccgaggaca cggctgtgta ttactgtgca | 300 | |
| agagagcagc agcagctggt accgcactac tactactacg gtatggacgt ctggggccaa | 360 | |
| gggaccacgg tcaccgtctc ctcagcctcc accaagggcc catcggtctt ccccctggca | 420 | |
| ccctcctcca agagcacctc tgggggcaca gcggccctgg gctgcctggt caaggactac | 480 | |
| ttccccgaac cggtgacggt gtcgtggaac tcaggcgccc tgaccagcgg cgtgcacacc | 540 | |
| ttcccggctg tcctacagtc ctcaggactc tactccctca gcagcgtggt gaccgtgccc | 600 | |
| tccagcagct gggcaccca gacctacatc tgcaacgtga atcacaagcc cagcaacacc | 660 | |
| aaggtggaca agaaagttga gcccaaatct tgt | 693 | |

```
<210> SEQ ID NO 504
<211> LENGTH: 645
<212> TYPE: DNA
<213> ORGANISM: Artificial
<220> FEATURE:
<223> OTHER INFORMATION: light chain region/domain

<400> SEQUENCE: 504
```

| | | |
|---|---|---|
| gatgttgtga tgactcagtc tccctccgtg tccgggtctc ctggacagtc agtcaccatc | 60 | |
| tcctgcactg gaaccaccag tgacgttggt ggctataact atgtctcctg gtaccaacag | 120 | |
| cgcccaggca agcccccaa actcatgatt tatgaggtca gtaagcggcc ctcaggggtc | 180 | |
| cctgatcgct tctctggctc caagtctggc aacacggcct ccctgaccgt ctctgggctc | 240 | |
| caggctgagg acgaggctga ttattactgc agctcatata caagcagcag cactctcttc | 300 | |
| ggaactggga ccaagctgac cgtcctaggt cagcccaagg ctgccccctc ggtcactctg | 360 | |
| ttcccgccct cctctgagga gcttcaagcc aacaaggcca cactggtgtg tctcataagt | 420 | |
| gacttctacc cgggagccgt gacagtggcc tggaaggcag atagcagccc cgtcaaggcg | 480 | |
| ggagtggaga ccaccacacc ctccaaacaa agcaacaaca gtacgcggc cagcagctat | 540 | |
| ctgagcctga cgcctgagca gtggaagtcc cacagaagct acagctgcca ggtcacgcat | 600 | |
| gaagggagca ccgtggagaa gacagtggcc cctacagaat gttca | 645 | |

```
<210> SEQ ID NO 505
<211> LENGTH: 369
<212> TYPE: DNA
<213> ORGANISM: Artificial
<220> FEATURE:
<223> OTHER INFORMATION: heavy chain region/domain

<400> SEQUENCE: 505
```

| | | |
|---|---|---|
| gaggtccagc tggtgcagtc tgggggggc ttggtccagc ctgggggtc cctgagactc | 60 | |
| tcctgttcag cctctggatt caccttcagt agctatgcta tgcactgggt ccgccaggct | 120 | |
| ccagggaagg gactggaata tgtttcagct attagtactg atggggtag cacatactac | 180 | |
| gcagactccg tgaagggcag attcaccatc tccagagaca attccaagaa cacgctgtat | 240 | |
| ctgcaaatga acagcctgag agctgaggac acggctgtgt attactgtgc gaaaacgtat | 300 | |
| tacgattttt ggaggaccta ctacggtatg gacgtctggg gccaagggac aatggtcacc | 360 | |
| gtctcttca | 369 | |

```
<210> SEQ ID NO 506
<211> LENGTH: 45
<212> TYPE: DNA
<213> ORGANISM: Artificial
<220> FEATURE:
<223> OTHER INFORMATION: linker sequence

<400> SEQUENCE: 506
ggaggtggcg ggtctggtgg tagcggaagc ggtggtggcg gatcc            45

<210> SEQ ID NO 507
<211> LENGTH: 324
<212> TYPE: DNA
<213> ORGANISM: Artificial
<220> FEATURE:
<223> OTHER INFORMATION: light chain region/domain

<400> SEQUENCE: 507
gaagcgacac tcacgcagtc tccatcctcc ctgtctgcat ctgtaggaga cagagtcacc    60
atcacttgcc gggcaagtca gagcattagc agctatttaa attggtatca gcagaaacca   120
gggagagccc ctaagctcct gatctatgct gcatccagtt tgcaaagtgg ggtcccatca   180
cggttcagtg gcagtggatc tgggacagat ttcactctca ccatcagcag tctgcaacct   240
gaagattttg caacttacta ctgtcaacag agttacagta ccccgtacac ttttggccag   300
gggacacgac tggagattaa acgt                                          324

<210> SEQ ID NO 508
<211> LENGTH: 351
<212> TYPE: DNA
<213> ORGANISM: Artificial
<220> FEATURE:
<223> OTHER INFORMATION: heavy chain region/domain

<400> SEQUENCE: 508
gaggtccagc tggtacagtc tgggggggc ttggtacagc ctggggggtc cctgagactc     60
tcctgtgcag cctctggatt cactttagc aactatgcca tgacctgggt ccgccaggct    120
ccggggaagg ggctagagtg ggtctcaact attgctggta gtggtgacaa cacatactac   180
gcagactccg tgaagggccg attcaccatc tccagagaca atgacaagaa cacactgtat   240
ctgcaaatga acagtctgag agccgacgac acggctgttt attactgtgc aagagaccgg   300
tactacacta tggacgtctg gggccaaggc accctggtca ccgtctcctc a            351

<210> SEQ ID NO 509
<211> LENGTH: 45
<212> TYPE: DNA
<213> ORGANISM: Artificial
<220> FEATURE:
<223> OTHER INFORMATION: linker sequence

<400> SEQUENCE: 509
ggaggtggcg ggtctggtgg tagcggaagc agtggtggcg gatcc            45

<210> SEQ ID NO 510
<211> LENGTH: 336
<212> TYPE: DNA
<213> ORGANISM: Artificial
<220> FEATURE:
<223> OTHER INFORMATION: light chain region/domain

<400> SEQUENCE: 510
cagtctgtcg tgacgcagcc gccctccgcg tccgggtctc ctggacagtc agtcaccatc    60
```

```
tcctgcactg gaaccagcag tgacgttggt ggttataacc atgtctcctg gtaccaacag    120
cacccaggca aggcccccaa actcttgatt tatgaggtca gtgagcggcc ctcagggggtc   180 cctgatcgct tctctggctc caagtctgac aacaaggcct ccctgaccat cattgggctc    240
cagactgaag atgaggctga ttattattgc cagtcctatg acagcagcct gagtggttcc    300
ctcttcggaa ccgggaccaa gctgaccgtc ctacgt                              336
```

<210> SEQ ID NO 511
<211> LENGTH: 355
<212> TYPE: DNA
<213> ORGANISM: Artificial
<220> FEATURE:
<223> OTHER INFORMATION: VH Domain

<400> SEQUENCE: 511

```
aaggtgcagc tacagcagtg gggcgcagga ctgttgaagc cttcggagac cctgtccctc    60
acctgcgctg tctatggtgg gtccttcagt ggttactact ggagctggat ccgccagccc    120
ccagggaagg ggctggagtg gattgggaa atcaatcata gtggaagcac caactacaac    180
ccgtccctca agagtcgagt caccatatca gtagacacgt ccaagaacca gttctccctg    240
aagctgagct ctgtgaccgc cgcggacacg gccgtgtatt actgtgttag actccccatg    300
attaagaagt catttgatat ttggggccca ggcaccctgg tcaccgtctc ctcag         355
```

<210> SEQ ID NO 512
<211> LENGTH: 358
<212> TYPE: DNA
<213> ORGANISM: Artificial
<220> FEATURE:
<223> OTHER INFORMATION: VH Domain

<400> SEQUENCE: 512

```
gaggtgcagc tggtggagtc cgggggaggc gtggtccagc ctgggaggtc cctgagactc    60
tcctgtgcag cctctggatt caccttcagt agctatgcta tgcactgggt ccgccaggct    120
ccagggaagg gtctagagtg gattggaaat atctatcatg atgggagcac cttctacaac    180
ccgtccctca agagtctagt caccatctcc agagacgatt ccacgaacac gctgtatctg    240
caaatgaaca gcctgagagc cgaggacaca gccatatatt actgtgccag agtttggctt    300
tatggttcag gctacatgga cgtctggggc aaaggcaccc tggtcaccgt ctcctcag     358
```

<210> SEQ ID NO 513
<211> LENGTH: 348
<212> TYPE: DNA
<213> ORGANISM: Artificial
<220> FEATURE:
<223> OTHER INFORMATION: VH Domain

<400> SEQUENCE: 513

```
gaggtgcagc tggtggagtc tggggggaggc ttggtacagc ctggagggtc cctgagactc    60
tcctgtgcag cctctgcttt cgatttctat gattatgaaa tgagctgggt ccgccaggct   120
ccagggaagg ccctggagtg gattgggaa atccatcata gtgggagcac ctactacaac    180
ccgtccctca agggccgatt caccatctcc agagacaatt ccaagaacac gctgtatctg   240
caaatgaaca gcctgagagc cgaggacacg gccgtgtatt actgtgccaa ggacgtcagc   300
tatcacgcgg acgtctgggg ccaagggacc acggtcaccg tctcctca               348
```

<210> SEQ ID NO 514
<211> LENGTH: 372

```
<212> TYPE: DNA
<213> ORGANISM: Artificial
<220> FEATURE:
<223> OTHER INFORMATION: VH Domain

<400> SEQUENCE: 514
gaggtgcagc tggtggagtc tgggggaggc ttggtacagc ctggagggtc cctgagactc      60
tcctgtgcag cctctggatt cacctttgat gattatgcca tgagctgggt ccgccaggct    120
ccagggaagg gcctagagtg gattgggcgt atgtataaca atgggaggac cagctacaac    180
ccctccctca agagtctagt caccatctcc agagacaatt ccaagaacac gctgtatctg    240
caaatgaaca gcctgagagc cgaggacaca gccacatatt actgtgcgag agacaatctg    300
ggctatagac cttcagaaaa cctctatggt atggacgtct ggggccaagg gaccacggtc    360
accgtctcct ca                                                        372

<210> SEQ ID NO 515
<211> LENGTH: 357
<212> TYPE: DNA
<213> ORGANISM: Artificial
<220> FEATURE:
<223> OTHER INFORMATION: VH Domain

<400> SEQUENCE: 515
gaggtgcagc tggtggagtc tgggggaggc ttggtacagc ctggagggtc cctgagactc      60
tcctgtaagg gttctggatt caccttaagt gactactaca tcggctgggt ccgccaggct    120
ccagggaagg gtctagagtg gattgggagt atgtatcata gtgggcgcac ctacatcaac    180
ccgtccctca agagtcgagt caccatctcc agagacaatt ccaagaacac gctgtatctg    240
caaatgaaca gcctgagagc cgaggacaca gccgtgtatt actgtgcgag aggcggtata    300
actggaacga cgcctattga ctactggggc cagggaaccc tggtcaccgt ctcctca       357

<210> SEQ ID NO 516
<211> LENGTH: 15
<212> TYPE: PRT
<213> ORGANISM: Artificial
<220> FEATURE:
<223> OTHER INFORMATION: linker sequence

<400> SEQUENCE: 516

Gly Gly Gly Gly Ser Gly Gly Ser Gly Ser Gly Gly Gly Gly Ser
1               5                   10                  15

<210> SEQ ID NO 517
<211> LENGTH: 15
<212> TYPE: PRT
<213> ORGANISM: Artificial
<220> FEATURE:
<223> OTHER INFORMATION: linker sequence

<400> SEQUENCE: 517

Gly Gly Gly Gly Ser Gly Gly Ser Gly Ser Ser Gly Gly Gly Ser
1               5                   10                  15

<210> SEQ ID NO 518
<211> LENGTH: 15
<212> TYPE: PRT
<213> ORGANISM: Artificial
<220> FEATURE:
<223> OTHER INFORMATION: linker sequence

<400> SEQUENCE: 518
```

```
Gly Gly Gly Gly Ser Gly Gly Gly Ser Gly Gly Gly Ser
1               5                   10                  15
```

<210> SEQ ID NO 519
<211> LENGTH: 15
<212> TYPE: PRT
<213> ORGANISM: Artificial
<220> FEATURE:
<223> OTHER INFORMATION: linker sequence

<400> SEQUENCE: 519

```
Gly Gly Gly Gly Ser Gly Ser Gly Ala Ser Gly Gly Gly Ser
1               5                   10                  15
```

<210> SEQ ID NO 520
<211> LENGTH: 15
<212> TYPE: PRT
<213> ORGANISM: Artificial
<220> FEATURE:
<223> OTHER INFORMATION: linker sequence

<400> SEQUENCE: 520

```
Gly Gly Gly Gly Ser Gly Ser Gly Ala Ser Gly Gly Gly Ser
1               5                   10                  15
```

<210> SEQ ID NO 521
<211> LENGTH: 15
<212> TYPE: PRT
<213> ORGANISM: Artificial
<220> FEATURE:
<223> OTHER INFORMATION: linker sequence

<400> SEQUENCE: 521

```
Ser Gly Gly Gly Ser Gly Gly Gly Gly Ser Gly Gly Gly Gly Ser
1               5                   10                  15
```

<210> SEQ ID NO 522
<211> LENGTH: 18
<212> TYPE: PRT
<213> ORGANISM: Artificial
<220> FEATURE:
<223> OTHER INFORMATION: linker sequence

<400> SEQUENCE: 522

```
Gly Ser Thr Ser Gly Ser Gly Lys Pro Gly Ser Gly Glu Gly Ser Thr
1               5                   10                  15

Lys Gly
```

<210> SEQ ID NO 523
<211> LENGTH: 19
<212> TYPE: PRT
<213> ORGANISM: Artificial
<220> FEATURE:
<223> OTHER INFORMATION: linker sequence

<400> SEQUENCE: 523

```
Pro Asn Gly Ala Ser Gln Ser Ser Ala Ser His Thr Gly Ser Ala
1               5                   10                  15

Pro Gly Ser
```

<210> SEQ ID NO 524
<211> LENGTH: 19
<212> TYPE: PRT
<213> ORGANISM: Artificial
<220> FEATURE:
<223> OTHER INFORMATION: linker sequence

```
<400> SEQUENCE: 524

Pro Asn Gly Ala Ser Asn Ser Gly Ser Ala Pro Asp Thr Ser Ser Ala
1               5                   10                  15

Pro Gly Ser

<210> SEQ ID NO 525
<211> LENGTH: 19
<212> TYPE: PRT
<213> ORGANISM: Artificial
<220> FEATURE:
<223> OTHER INFORMATION: linker sequence

<400> SEQUENCE: 525

Pro Asn Gly Ala Ser His Ser Gly Ser Ala Pro Asn Thr Ser Ser Ala
1               5                   10                  15

Pro Gly Ser

<210> SEQ ID NO 526
<211> LENGTH: 19
<212> TYPE: PRT
<213> ORGANISM: Artificial
<220> FEATURE:
<223> OTHER INFORMATION: linker sequence

<400> SEQUENCE: 526

Pro Asn Gly Ala Ser Glu Ser Gly Ser Ala Ser Lys Thr Ser Ser Ala
1               5                   10                  15

Ser Gly Ser

<210> SEQ ID NO 527
<211> LENGTH: 19
<212> TYPE: PRT
<213> ORGANISM: Artificial
<220> FEATURE:
<223> OTHER INFORMATION: linker sequence

<400> SEQUENCE: 527

Pro Asn Gly Ala Ser Asn Ser Gly Ser Ala Pro Lys Thr Gly Ser Ala
1               5                   10                  15

Ser Gly Ser

<210> SEQ ID NO 528
<211> LENGTH: 19
<212> TYPE: PRT
<213> ORGANISM: Artificial
<220> FEATURE:
<223> OTHER INFORMATION: linker sequence

<400> SEQUENCE: 528

Pro Asn Gly Ala Ser Lys Ser Gly Ser Ala Ser Gln Thr Ser Ser Ala
1               5                   10                  15

Pro Gly Ser

<210> SEQ ID NO 529
<211> LENGTH: 19
<212> TYPE: PRT
<213> ORGANISM: Artificial
<220> FEATURE:
<223> OTHER INFORMATION: linker sequence

<400> SEQUENCE: 529

Pro Asn Gly Ala Ser His Ser Ser Ser Ala Ser Gln Thr Gly Ser Ala
```

```
1               5                   10                  15
Pro Gly Ser

<210> SEQ ID NO 530
<211> LENGTH: 12
<212> TYPE: PRT
<213> ORGANISM: Artificial
<220> FEATURE:
<223> OTHER INFORMATION: linker sequence

<400> SEQUENCE: 530

Pro Asn Gly Ala Ser Lys Arg Ser Ala Pro Gly Ser
1               5                   10

<210> SEQ ID NO 531
<211> LENGTH: 19
<212> TYPE: PRT
<213> ORGANISM: Artificial
<220> FEATURE:
<223> OTHER INFORMATION: linker sequence

<400> SEQUENCE: 531

Pro Asn Gly Ala Ser His Ser Gly Ser Ala Pro His Thr Ser Ser Ala
1               5                   10                  15

Ser Gly Ser

<210> SEQ ID NO 532
<211> LENGTH: 15
<212> TYPE: PRT
<213> ORGANISM: Artificial
<220> FEATURE:
<223> OTHER INFORMATION: linker sequence

<400> SEQUENCE: 532

Arg Gly Arg Gly Arg Gly Arg Gly Arg Ser Arg Gly Gly Gly Ser
1               5                   10                  15

<210> SEQ ID NO 533
<211> LENGTH: 15
<212> TYPE: PRT
<213> ORGANISM: Artificial
<220> FEATURE:
<223> OTHER INFORMATION: linker sequence

<400> SEQUENCE: 533

Ser His Gly Gly Ser His Gly Gly Ser Gly Gly Gly Ser
1               5                   10                  15
```

MOLECULES THAT BIND TO SARS-COV-2

CROSS-REFERENCE TO RELATED APPLICATIONS

This application claims the benefit of U.S. Provisional Application Ser. No. 62/988,856, filed Mar. 12, 2020. The disclosure of the prior application is considered part of (and is incorporated by reference in) the disclosure of this application.

BACKGROUND

1. Technical Field

This document relates to methods and materials involved in binding a molecule (e.g., an antibody, a fragment of an antibody, or an antibody domain) to a severe acute respiratory distress coronavirus 2 (SARS-CoV-2) antigen. For example, this document provides binders (e.g., antibodies, antigen binding fragments, or antibody domains) that bind to a SARS-CoV-2 polypeptide and methods and materials for using such binders to treat acute respiratory distress syndrome (COVID-19).

2. Background Information

SARS-CoV-2 is a newly identified emerging coronavirus causing an acute respiratory distress syndrome known as COVID-19 that is similar to severe acute respiratory distress syndrome (SARS) caused by the closely related SARS-CoV. More than 110,000 thousand humans were infected with SARS-CoV-2 and more than 4,000 COVID-19 deaths have been reported to date. SARS-CoV and SARS-CoV-2 have similar structural proteins including the spike (S), envelope (E), membrane (M), and nucleocapsid (N) proteins. In SARS-CoV, the S protein is the most immunogenic and contains a receptor binding domain (RBD) that is a target for neutralizing antibodies (Buchholz et al., *Proc. Natl. Acad. Sci.*, 101:9804-9809 (2004); and Prabakaran et al., *J. Biol. Chem.*, 281:15829-15836 (2006)). The RBD binds to the angiotensin-converting enzyme 2 (ACE2), which serves as a functional receptor to mediate cell entry of the virus (Li et al., *Nature*, 426:450-454 (2003)). The RBD-ACE2 interaction is of high affinity and is highly specific. The SARS-CoV-2 and SARS-CoV proteins share a high degree of homology, except for the receptor binding domain which has a relatively low degree of homology. Thus, many neutralizing antibodies developed against SARS-CoV that target the RBD cannot neutralize SARS-CoV-2.

SUMMARY

This document provides methods and materials involved in binding a molecule (e.g., an antibody, an antigen binding fragment, or an antibody domain) to a SARS-CoV-2 antigen. For example, this document provides binders (e.g., antibodies, antigen binding fragments, and antibody domains) that bind to a SARS-CoV-2 polypeptide and methods and materials for using one or more such binders to treat a mammal (e.g., a human) having COVID-19 (or a viral infection caused by SARS-CoV-2). This document also provides methods and materials for using one or more binders (e.g., one or more antibodies, one or more antigen binding fragments, and one or more antibody domains) described herein prophylactically to reduce a mammal's susceptibility to COVID-19 (or a viral infection caused by SARS-CoV-2) and/or prophylactically to reduce the severity of COVID-19 (or a viral infection caused by SARS-CoV-2) in a mammal (e.g., a human) should that mammal become infected with SARS-CoV-2.

As described herein, binders (e.g., one or more antibodies, one or more antigen binding fragments, and/or one or more antibody domains) can be designed to have the ability to bind to a SARS-CoV-2 polypeptide (e.g., the S protein of SARS-CoV-2 or the RBD of the S protein of SARS-CoV-2). For example, a binder (e.g., an antibody, an antigen binding fragment, or antibody domain) provided herein can have the ability to bind to the RBD of the S protein of SARS-CoV-2. In some cases, a binder (e.g., an antibody, an antigen binding fragment, or antibody domain) provided herein having the ability to bind to a SARS-CoV-2 polypeptide (e.g., the S protein of SARS-CoV-2 or the RBD of the S protein of SARS-CoV-2) also can have the ability to neutralize SARS-CoV-2 (e.g., reduce or prevent the ability of SARS-CoV-2 to enter cells, such as human cells, in vitro or in vivo).

As also described herein, the binders (e.g., one or more antibodies, one or more antigen binding fragments, and/or one or more antibody domains) provided herein can be used to treat a mammal (e.g., a human) having COVID-19 (or a viral infection caused by SARS-CoV-2). For example, a mammal (e.g., a human) having COVID-19 (or a viral infection caused by SARS-CoV-2) can be administered a composition comprising one or more binders (e.g., one or more antibodies, one or more antigen binding fragments, and/or one or more antibody domains) described herein to reduce the severity of COVID-19 (or the viral infection caused by SARS-CoV-2) and/or to reduce the duration of COVID-19 (or the viral infection caused by SARS-CoV-2).

In addition, as described herein, the binders (e.g., one or more antibodies, one or more antigen binding fragments, and/or one or more antibody domains) provided herein can be used prophylactically to reduce or eliminate a mammal's susceptibility to COVID-19 (or a viral infection caused by SARS-CoV-2) and/or used prophylactically to reduce the severity of COVID-19 (or a viral infection caused by SARS-CoV-2) in a mammal (e.g., a human) should that mammal become infected with SARS-CoV-2. For example, a mammal lacking COVID-19 and lacking SARS-CoV-2 (e.g., a healthy human) can be administered a composition comprising one or more binders (e.g., one or more antibodies, one or more antigen binding fragments, and/or one or more antibody domains) described herein (a) to reduce the mammal's susceptibility to COVID-19 (or a viral infection caused by SARS-CoV-2) and/or (b) to reduce the severity of COVID-19 (or the viral infection caused by SARS-CoV-2) and/or duration of COVID-19 (or the viral infection caused by SARS-CoV-2) should that mammal later become infected with SARS-CoV-2.

In some cases, a binder (e.g., an antibody, antigen binding fragment, and/or antibody domain) provided herein can be used to detect the presence or absence of SARS-CoV-2. For example, a binder (e.g., an antibody, antigen binding fragment, and/or antibody domain) provided herein can be used to determine whether or not a sample (e.g., a biological sample such as a nasal sample, a saliva sample, a sputum sample, or a blood sample) obtained from a mammal (e.g., a human) contains SARS-CoV-2. Having the ability to detect the presence or absence of SARS-CoV-2 in a sample obtained from a mammal (e.g., a human) can allow clinicians, health professionals, and patients to make better decisions about possible quarantine and/or treatment options.

In general, one aspect of this document features an antibody (or molecule) having the ability to bind to SEQ ID NO:495 or SEQ ID NO:496. The antibody can be a monoclonal antibody. The antibody can be an scFv antibody. The antibody can comprise, consist essentially of, or consist of (i) a heavy chain variable domain or region comprising the amino acid sequences set forth in SEQ ID NO:1, SEQ ID NO:2, and SEQ ID NO:3, and a light chain variable domain or region comprising the amino acid sequences set forth in SEQ ID NO:9, SEQ ID NO:10, and SEQ ID NO:11; (ii) a heavy chain variable domain or region comprising the amino acid sequences set forth in SEQ ID NO:17, SEQ ID NO:18, and SEQ ID NO:19, and a light chain variable domain or region comprising the amino acid sequences set forth in SEQ ID NO:25, SEQ ID NO:26, and SEQ ID NO:27; (iii) a heavy chain variable domain or region comprising the amino acid sequences set forth in SEQ ID NO:33, SEQ ID NO:34, and SEQ ID NO:35, and a light chain variable domain or region comprising the amino acid sequences set forth in SEQ ID NO:41, SEQ ID NO:42, and SEQ ID NO:43; (iv) a heavy chain variable domain or region comprising the amino acid sequences set forth in SEQ ID NO:49, SEQ ID NO:50, and SEQ ID NO:51, and a light chain variable domain or region comprising the amino acid sequences set forth in SEQ ID NO:57, SEQ ID NO:58, and SEQ ID NO:59; (v) a heavy chain variable domain or region comprising the amino acid sequences set forth in SEQ ID NO:65, SEQ ID NO:66, and SEQ ID NO:67; (vi) a heavy chain variable domain or region comprising the amino acid sequences set forth in SEQ ID NO:73, SEQ ID NO:74, and SEQ ID NO:75; (vii) a heavy chain variable domain or region comprising the amino acid sequences set forth in SEQ ID NO:81, SEQ ID NO:82, and SEQ ID NO:83; (viii) a heavy chain variable domain or region comprising the amino acid sequences set forth in SEQ ID NO:89, SEQ ID NO:90, and SEQ ID NO:91; or (ix) a heavy chain variable domain or region comprising the amino acid sequences set forth in SEQ ID NO:97, SEQ ID NO:98, and SEQ ID NO:99. In one embodiment, the antibody can comprise, consist essentially of, or consist of the heavy chain variable domain or region of the (i). In some cases, this heavy chain variable domain or region can comprise, consist essentially of, or consist of an amino acid sequence having at least 90 percent identity to the amino acid sequence set forth in SEQ ID NO:8. The antibody can comprise, consist essentially of, or consist of the light chain variable domain or region of the (i). In some cases, this light chain variable domain or region can comprise, consist essentially of, or consist of an amino acid sequence having at least 90 percent identity to the amino acid sequence set forth in SEQ ID NO:16.

In another embodiment, the antibody can comprise, consist essentially of, or consist of the heavy chain variable domain or region of the (ii). In some cases, this heavy chain variable domain or region can comprise, consist essentially of, or consist of an amino acid sequence having at least 90 percent identity to the amino acid sequence set forth in SEQ ID NO:24. The antibody can comprise, consist essentially of, or consist of the light chain variable domain or region of the (ii). In some cases, this light chain variable domain or region can comprise, consist essentially of, or consist of an amino acid sequence having at least 90 percent identity to the amino acid sequence set forth in SEQ ID NO:32.

In another embodiment, the antibody can comprise, consist essentially of, or consist of the heavy chain variable domain or region of the (iii). In some cases, this heavy chain variable domain or region can comprise, consist essentially of, or consist of an amino acid sequence having at least 90 percent identity to the amino acid sequence set forth in SEQ ID NO:40. The antibody can comprise, consist essentially of, or consist of the light chain variable domain or region of the (iii). In some cases, this light chain variable domain or region can comprise, consist essentially of, or consist of an amino acid sequence having at least 90 percent identity to the amino acid sequence set forth in SEQ ID NO:48.

In another embodiment, the antibody can comprise, consist essentially of, or consist of the heavy chain variable domain or region of the (iv). In some cases, this heavy chain variable domain or region can comprise, consist essentially of, or consist of an amino acid sequence having at least 90 percent identity to the amino acid sequence set forth in SEQ ID NO:56. The antibody can comprise, consist essentially of, or consist of the light chain variable domain or region of the (iv). In some cases, this light chain variable domain or region can comprise, consist essentially of, or consist of an amino acid sequence having at least 90 percent identity to the amino acid sequence set forth in SEQ ID NO:64.

In another embodiment, the antibody can comprise, consist essentially of, or consist of the heavy chain variable domain or region of the (v). In some cases, this heavy chain variable domain or region can comprise, consist essentially of, or consist of an amino acid sequence having at least 90 percent identity to the amino acid sequence set forth in SEQ ID NO:72.

In another embodiment, the antibody can comprise, consist essentially of, or consist of the heavy chain variable domain or region of the (vi). In some cases, this heavy chain variable domain or region can comprise, consist essentially of, or consist of an amino acid sequence having at least 90 percent identity to the amino acid sequence set forth in SEQ ID NO:80.

In another embodiment, the antibody can comprise, consist essentially of, or consist of the heavy chain variable domain or region of the (vii). In some cases, this heavy chain variable domain or region can comprise, consist essentially of, or consist of an amino acid sequence having at least 90 percent identity to the amino acid sequence set forth in SEQ ID NO:88.

In another embodiment, the antibody can comprise, consist essentially of, or consist of the heavy chain variable domain or region of the (viii). In some cases, this heavy chain variable domain or region can comprise, consist essentially of, or consist of an amino acid sequence having at least 90 percent identity to the amino acid sequence set forth in SEQ ID NO:96.

In another embodiment, the antibody can comprise, consist essentially of, or consist of the heavy chain variable domain or region of the (ix). In some cases, this heavy chain variable domain or region can comprise, consist essentially of, or consist of an amino acid sequence having at least 90 percent identity to the amino acid sequence set forth in SEQ ID NO:104.

In another aspect, this document features an antigen binding fragment having the ability to bind to SEQ ID NO:495 or SEQ ID NO:496. The antigen binding fragment can be monoclonal. The antigen binding fragment can be an Fab. The antigen binding fragment can comprise, consist essentially of, or consist of (i) a heavy chain variable domain or region comprising the amino acid sequences set forth in SEQ ID NO:1, SEQ ID NO:2, and SEQ ID NO:3, and a light chain variable domain or region comprising the amino acid sequences set forth in SEQ ID NO:9, SEQ ID NO:10, and SEQ ID NO:11; (ii) a heavy chain variable domain or region comprising the amino acid sequences set forth in SEQ ID NO:17, SEQ ID NO:18, and SEQ ID NO:19, and a light chain variable domain or region comprising the amino acid sequences set forth in SEQ ID NO:25, SEQ ID NO:26, and SEQ ID NO:27; (iii) a heavy chain variable domain or region comprising the amino acid sequences set forth in SEQ ID NO:33, SEQ ID NO:34, and SEQ ID NO:35, and a light chain variable domain or region comprising the amino acid sequences set forth in SEQ ID NO:41, SEQ ID NO:42, and SEQ ID NO:43; (iv) a heavy chain variable domain or region comprising the amino acid sequences set forth in SEQ ID NO:49, SEQ ID NO:50, and SEQ ID NO:51, and a light chain variable domain or region comprising the amino acid sequences set forth in SEQ ID NO:57, SEQ ID NO:58, and SEQ ID NO:59; (v) a heavy chain variable domain or region comprising the amino acid sequences set forth in SEQ ID NO:65, SEQ ID NO:66, and SEQ ID NO:67; (vi) a heavy chain variable domain or region comprising the amino acid sequences set forth in SEQ ID NO:73, SEQ ID NO:74, and SEQ ID NO:75; (vii) a heavy chain variable domain or region comprising the amino acid sequences set forth in SEQ ID NO:81, SEQ ID NO:82, and SEQ ID NO:83; (viii) a heavy chain variable domain or region comprising the amino acid sequences set forth in SEQ ID NO:89, SEQ ID NO:90, and SEQ ID NO:91; or (ix) a heavy chain variable domain or region comprising the amino acid sequences set forth in SEQ ID NO:97, SEQ ID NO:98, and SEQ ID NO:99. In one embodiment, antigen binding fragment can comprise, consist essentially of, or consist of the heavy chain variable domain or region of the (i). In some cases, this heavy chain variable domain or region can comprise, consist essentially of, or consist of an amino acid sequence having at least 90 percent identity to the amino acid sequence set forth in SEQ ID NO:8. The antigen binding fragment can comprise, consist essentially of, or consist of the light chain variable domain or region of the (i). In some cases, this light chain variable domain or region can comprise, consist essentially of, or consist of an amino acid sequence having at least 90 percent identity to the amino acid sequence set forth in SEQ ID NO:16.

In another embodiment, the antigen binding fragment can comprise, consist essentially of, or consist of the heavy chain variable domain or region of the (ii). In some cases, this heavy chain variable domain or region can comprise, consist essentially of, or consist of an amino acid sequence having at least 90 percent identity to the amino acid sequence set forth in SEQ ID NO:24. The antigen binding fragment can comprise, consist essentially of, or consist of the light chain variable domain or region of the (ii). In some cases, this light chain variable domain or region can comprise, consist essentially of, or consist of an amino acid sequence having at least 90 percent identity to the amino acid sequence set forth in SEQ ID NO:32.

In another embodiment, the antigen binding fragment can comprise, consist essentially of, or consist of the heavy chain variable domain or region of the (iii). In some cases, this heavy chain variable domain or region can comprise, consist essentially of, or consist of an amino acid sequence having at least 90 percent identity to the amino acid sequence set forth in SEQ ID NO:40. The antigen binding fragment can comprise, consist essentially of, or consist of the light chain variable domain or region of the (iii). In some cases, this light chain variable domain or region can comprise, consist essentially of, or consist of an amino acid sequence having at least 90 percent identity to the amino acid sequence set forth in SEQ ID NO:48.

In another embodiment, the antigen binding fragment can comprise, consist essentially of, or consist of the heavy chain variable domain or region of the (iv). In some cases, this heavy chain variable domain or region can comprise, consist essentially of, or consist of an amino acid sequence having at least 90 percent identity to the amino acid sequence set forth in SEQ ID NO:56. The antigen binding fragment can comprise, consist essentially of, or consist of the light chain variable domain or region of the (iv). In some cases, this light chain variable domain or region can comprise, consist essentially of, or consist of an amino acid sequence having at least 90 percent identity to the amino acid sequence set forth in SEQ ID NO:64.

In another embodiment, the antigen binding fragment can comprise, consist essentially of, or consist of the heavy chain variable domain or region of the (v). In some cases, this heavy chain variable domain or region can comprise, consist essentially of, or consist of an amino acid sequence having at least 90 percent identity to the amino acid sequence set forth in SEQ ID NO:72.

In another embodiment, the antigen binding fragment can comprise, consist essentially of, or consist of the heavy chain variable domain or region of the (vi). In some cases, this heavy chain variable domain or region can comprise, consist essentially of, or consist of an amino acid sequence having at least 90 percent identity to the amino acid sequence set forth in SEQ ID NO:80.

In another embodiment, the antigen binding fragment can comprise, consist essentially of, or consist of the heavy chain variable domain or region of the (vii). In some cases, this heavy chain variable domain or region can comprise, consist essentially of, or consist of an amino acid sequence having at least 90 percent identity to the amino acid sequence set forth in SEQ ID NO:88.

In another embodiment, the antigen binding fragment can comprise, consist essentially of, or consist of the heavy chain variable domain or region of the (viii). In some cases, this heavy chain variable domain or region can comprise, consist essentially of, or consist of an amino acid sequence having at least 90 percent identity to the amino acid sequence set forth in SEQ ID NO:96.

In another embodiment, the antigen binding fragment can comprise, consist essentially of, or consist of the heavy chain variable domain or region of the (ix). In some cases, this heavy chain variable domain or region can comprise, consist essentially of, or consist of an amino acid sequence having at least 90 percent identity to the amino acid sequence set forth in SEQ ID NO:104.

In another aspect, this document features an antibody domain having the ability to bind to SEQ ID NO:495 or SEQ ID NO:496. The antibody domain can be monoclonal. The antibody domain can be a VH domain. The antibody domain can comprise, consist essentially of, or consist of (i) a heavy chain variable domain or region comprising the amino acid sequences set forth in SEQ ID NO:65, SEQ ID NO:66, and SEQ ID NO:67; (ii) a heavy chain variable domain or region comprising the amino acid sequences set forth in SEQ ID NO:73, SEQ ID NO:74, and SEQ ID NO:75; (iii) a heavy chain variable domain or region comprising the amino acid sequences set forth in SEQ ID NO:81, SEQ ID NO:82, and SEQ ID NO:83; (iv) a heavy chain variable domain or region comprising the amino acid sequences set forth in SEQ ID NO:89, SEQ ID NO:90, and SEQ ID NO:91; or (v) a heavy chain variable domain or region comprising the amino acid sequences set forth in SEQ ID NO:97, SEQ ID NO:98, and SEQ ID NO:99. In one embodiment, the antibody domain can comprise, consist essentially of, or consist of the heavy chain variable domain or region of the (i). In some cases, this heavy chain variable domain or region can comprise, consist essentially of, or consist of an amino acid sequence having at least 90 percent identity to the amino acid sequence set forth in SEQ ID NO:72.

In another embodiment, the antibody domain can comprise, consist essentially of, or consist of the heavy chain variable domain or region of the (ii). In some cases, this heavy chain variable domain or region can comprise, consist essentially of, or consist of an amino acid sequence having at least 90 percent identity to the amino acid sequence set forth in SEQ ID NO:80.

In another embodiment, the antibody domain can comprise, consist essentially of, or consist of the heavy chain variable domain or region of the (iii). In some cases, this heavy chain variable domain or region can comprise, consist essentially of, or consist of an amino acid sequence having at least 90 percent identity to the amino acid sequence set forth in SEQ ID NO:88.

In another embodiment, the antibody domain can comprise, consist essentially of, or consist of the heavy chain variable domain or region of the (iv). In some cases, this heavy chain variable domain or region can comprise, consist essentially of, or consist of an amino acid sequence having at least 90 percent identity to the amino acid sequence set forth in SEQ ID NO:96.

In another embodiment, the antibody domain can comprise, consist essentially of, or consist of the heavy chain variable domain or region of the (v). In some cases, this heavy chain variable domain or region can comprise, consist essentially of, or consist of an amino acid sequence having at least 90 percent identity to the amino acid sequence set forth in SEQ ID NO:104.

In another aspect, this document features a nucleic acid comprising, consisting essentially of, or consisting of a nucleic acid sequence encoding at least part of an antibody, an antigen-binding fragment, or an antibody domain of any of the preceding 23 paragraphs (referred to herein as "the preceding 23 paragraphs"). The nucleic acid sequence can encode (i) a heavy chain variable domain or region comprising, consisting essentially of, or consisting of the amino acid sequences set forth in SEQ ID NO:1, SEQ ID NO:2, and SEQ ID NO:3; (ii) a heavy chain variable domain or region comprising, consisting essentially of, or consisting of the amino acid sequences set forth in SEQ ID NO:17, SEQ ID NO:18, and SEQ ID NO:19; (iii) a heavy chain variable domain or region comprising, consisting essentially of, or consisting of the amino acid sequences set forth in SEQ ID NO:33, SEQ ID NO:34, and SEQ ID NO:35; (iv) a heavy chain variable domain or region comprising, consisting essentially of, or consisting of the amino acid sequences set forth in SEQ ID NO:49, SEQ ID NO:50, and SEQ ID NO:51; (v) a heavy chain variable domain or region comprising, consisting essentially of, or consisting of the amino acid sequences set forth in SEQ ID NO:65, SEQ ID NO:66, and SEQ ID NO:67; (vi) a heavy chain variable domain or region comprising, consisting essentially of, or consisting of the amino acid sequences set forth in SEQ ID NO:73, SEQ ID NO:74, and SEQ ID NO:75; (vii) a heavy chain variable domain or region comprising, consisting essentially of, or consisting of the amino acid sequences set forth in SEQ ID NO:81, SEQ ID NO:82, and SEQ ID NO:83; (viii) a heavy chain variable domain or region comprising, consisting essentially of, or consisting of the amino acid sequences set forth in SEQ ID NO:89, SEQ ID NO:90, and SEQ ID NO:91; or (ix) a heavy chain variable domain or region comprising, consisting essentially of, or consisting of the amino acid sequences set forth in SEQ ID NO:97, SEQ ID NO:98, and SEQ ID NO:99. The nucleic acid sequence can encode (i) a light chain variable domain or region comprising, consisting essentially of, or consisting of the amino acid sequences set forth in SEQ ID NO:9, SEQ ID NO:10, and SEQ ID NO:11; (ii) a light chain variable domain or region comprising, consisting essentially of, or consisting of the amino acid sequences set forth in SEQ ID NO:25, SEQ ID NO:26, and SEQ ID NO:27; (iii) a light chain variable domain or region comprising, consisting essentially of, or consisting of the amino acid sequences set forth in SEQ ID NO:41, SEQ ID NO:42, and SEQ ID NO:43; or (iv) a light chain variable domain or region comprising, consisting essentially of, or consisting of the amino acid sequences set forth in SEQ ID NO:57, SEQ ID NO:58, and SEQ ID NO:59. The nucleic acid can be a viral vector. The nucleic acid can be a phagemid.

In another aspect, this document features a host cell comprising, consisting essentially of, or consisting of any nucleic acid of the preceding paragraph.

In another aspect, this document features a composition comprising, consisting essentially of, or consisting of an antibody, an antigen binding fragment, or an antibody of any of "the preceding 23 paragraphs." The composition can comprise, consist essentially of, or consist of the antibody. The composition can comprise, consist essentially of, or consist of the antigen binding fragment. The composition can comprise, consist essentially of, or consist of the antibody domain. The composition can comprise, consist essentially of, or consist of an antiviral agent. The antiviral agent can be Remdesivir, Galidesivir, or Favipiravir.

In another aspect, this document features a method of treating a mammal having COVID-19 or a viral infection caused by SARS-CoV-2. The method comprises, consists essentially of, or consists of administering, to the mammal, a composition comprising, consisting essentially of, or consisting of an antibody, an antigen binding fragment, or an antibody of any of "the preceding 23 paragraphs." The composition can comprise, consist essentially of, or consist of the antibody. The composition can comprise, consist essentially of, or consist of the antigen binding fragment. The composition can comprise, consist essentially of, or consist of the antibody domain. The composition can comprise, consist essentially of, or consist of an antiviral agent. The antiviral agent can be Remdesivir, Galidesivir, or Favipiravir. The mammal can be a human.

In another aspect, this document features a method of reducing a mammal's susceptibility to COVID-19 or a viral infection caused by SARS-CoV-2. The method comprises, consists essentially of, or consists of administering, to the mammal, a composition comprising, consisting essentially of, or consisting of an antibody, an antigen binding fragment, or an antibody of any of "the preceding 23 paragraphs." The composition can comprise, consist essentially of, or consist of the antibody. The composition can comprise, consist essentially of, or consist of the antigen binding fragment. The composition can comprise, consist essentially of, or consist of the antibody domain. The composition can comprise, consist essentially of, or consist of an antiviral agent. The antiviral agent can be Remdesivir, Galidesivir, or Favipiravir. The mammal can be a human.

In another aspect, this document features a method for binding a binding molecule to a SARS-CoV-2 virus. The method comprises, consists essentially of, or consists of contacting the virus with an antibody, an antigen binding fragment, or an antibody of any of "the preceding 23 paragraphs." The contacting can be performed in vitro. The contacting can be performed in vivo. The contacting can be performed within a mammal by administering the antibody, the antigen binding fragment, or the antibody domain to the mammal. The mammal can be a human.

Unless otherwise defined, all technical and scientific terms used herein have the same meaning as commonly understood by one of ordinary skill in the art to which this disclosure pertains. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 depicts the amino acid sequence of the S protein of SARS-CoV-2 (SEQ ID NO:495). The RBD of the S protein of SARS-CoV-2 is underlined (SEQ ID NO:496).

FIGS. 2A and 2B depict the amino acid sequences of the heavy chain variable domain (FIG. 2A) and the light chain variable domain (FIG. 2B) of an Fab designated Clone #1 (ab1). The complementarity determining regions (CDRs) and framework sequences of each also are delineated.

FIGS. 3A and 3B depict the amino acid sequences of the heavy chain variable domain (FIG. 3A) and the light chain variable domain (FIG. 3B) of an Fab designated Clone #2 (ab2). The CDRs and framework sequences of each also are delineated.

FIGS. 4A and 4B depict the amino acid sequences of the heavy chain variable domain (FIG. 4A) and the light chain variable domain (FIG. 4B) of an scFv designated Clone #3 (ab3). The CDRs and framework sequences of each also are delineated. FIG. 4C depicts exemplary linker amino acid sequences that can be used to link a heavy chain variable domain and a light chain variable domain together to form an scFv.

FIGS. 5A and 5B depict the amino acid sequences of the heavy chain variable domain (FIG. 5A) and the light chain variable domain (FIG. 5B) of an scFv designated Clone #4 (ab4). The CDRs and framework sequences of each also are delineated.

FIG. 6 depicts the amino acid sequence of a VH domain designated Clone #5 (ab5). The CDRs and framework sequences also are delineated.

FIG. 7 depicts the amino acid sequence of a VH domain designated Clone #6 (ab6). The CDRs and framework sequences also are delineated.

FIG. 8 depicts the amino acid sequence of a VH domain designated Clone #7. The CDRs and framework sequences also are delineated (ab7).

FIG. 9 depicts the amino acid sequence of a VH domain designated Clone #8. The CDRs and framework sequences also are delineated (ab8).

FIG. 10 depicts the amino acid sequence of a VH domain designated Clone #9 (ab9). The CDRs and framework sequences also are delineated.

FIG. 11 depicts the nucleic acid sequences encoding the indicated chains/domains of Clones #1-#9.

DETAILED DESCRIPTION

This document provides binders (e.g., antibodies, antigen binding fragments, and antibody domains) that bind (e.g., specifically bind) to a SARS-CoV-2 antigen such as the S protein of SARS-CoV-2 or the RBD of the S protein of SARS-CoV-2. The amino acid sequence of the S protein of SARS-CoV-2 is set forth in FIG. 1. In some cases, a binder (e.g., an antibody, antigen binding fragment, or antibody domain) provided herein can have the ability to bind to a SARS-CoV-2 antigen and can lack the ability to bind to a corresponding SARS-CoV antigen. For example, a binder (e.g., an antibody, antigen binding fragment, or antibody domain) provided herein can have the ability to bind to the RBD of the S protein of SARS-CoV-2 and can lack the ability to bind to the RBD of the S protein of SARS-CoV.

The term "antibody" as used herein includes polyclonal antibodies, monoclonal antibodies, recombinant antibodies, humanized antibodies, human antibodies, chimeric antibodies, multi-specific antibodies (e.g., bispecific antibodies) formed from at least two antibodies, diabodies, single-chain variable fragment antibodies (e.g., scFv antibodies), and tandem single-chain variable fragments antibody (e.g., taFv). A diabody can include two chains, each having a heavy chain variable domain and a light chain variable domain, either from the same or from different antibodies (see, e.g., Hornig and Farber-Schwarz, *Methods Mol. Biol.*, 907:713-27 (2012); and Brinkmann and Kontermann, *MAbs.*, 9(2):182-212 (2017)). The two variable regions can be connected by a polypeptide linker (e.g., a polypeptide linker having five to ten residues in length or a polypeptide linker as set forth in FIG. 4C). In some cases, an interdomain disulfide bond can be present in one or both of the heavy chain variable domain and light chain variable domain pairs of the diabody. A scFv is a single-chain polypeptide antibody in which the heavy chain variable domain and the light chain variable domain are directly connected or connected via a polypeptide linker (e.g., a polypeptide linker having eight to 18 residues in length or a polypeptide linker as set forth in FIG. 4C). See, also, Chen et al., *Adv. Drug Deliv. Rev.*, 65(10):1357-1369 (2013). An antibody provided herein can include the CDRs as described herein (e.g., as described in Table 40) and can be configured to be a human antibody, a humanized antibody, or a chimeric antibody. In some cases, an antibody provided herein can include the CDRs as described herein (e.g., as described in Table 40) and can be a monoclonal antibody. In some cases, an antibody provided herein can include the CDRs as described herein (e.g., as described in Table 40) and can be configured as a scFv antibody.

The term "antigen binding fragment" as used herein refers to a fragment of an antibody (e.g., a fragment of a humanized antibody, a fragment of a human antibody, or a fragment of a chimeric antibody) having the ability to bind to an antigen. Examples of antigen binding fragments include, without limitation, Fab, Fab', or F(ab')$_2$ antigen binding fragments. An antigen binding fragment provided herein can include the CDRs as described herein (e.g., as described in Table 40) and can be configured to be a human antigen binding fragment, a humanized antigen binding fragment, or a chimeric antigen binding fragment. In some cases, an antigen binding fragment provided herein can include the CDRs as described herein (e.g., as described in Table 40) and can be a monoclonal antigen binding fragment. In some cases, an antigen binding fragment provided herein can include the CDRs as described herein (e.g., as described in Table 40) and can be configured as an Fab antibody.

The term "antibody domain" as used herein refers to a domain of an antibody such as a heavy chain variable domain (VH domain) or a light chain variable domain (VL domain) in the absence of one or more other domains of an antibody. In some cases, an antibody domain can be a single antibody domain (e.g., a VH domain or a VL domain having the ability to bind to an antigen. An antibody domain provided herein can include the CDRs as described herein (e.g., as described in Table 40) and can be a human antibody domain (e.g., a human VH domain), a humanized antibody domain (e.g., a humanized VH domain), or a chimeric antibody domain (e.g., a chimeric VH domain). In some cases, an antibody domain provided herein can include the CDRs as described herein (e.g., as described in Table 40) and can be a monoclonal antibody domain. In some cases, an antibody domain provided herein can include the CDRs as described herein (e.g., as described in Table 40) and can be engineered as a single VH domain or a single VL domain.

An anti-SARS-CoV-2 antibody, anti-SARS-CoV-2 antigen binding fragment, or anti-SARS-CoV-2 antibody domain provided herein can be of the IgA-, IgD-, IgE-, IgG-, or IgM-type, including IgG- or IgM-types such as, without limitation, IgG1-, IgG2-, IgG3-, IgG4-, IgM1-, and IgM2-types. In some cases, an antibody provided herein (e.g., an anti-SARS-CoV-2 antibody) can be a scFv antibody. In some cases, an antigen binding fragment provided herein (e.g., an anti-SARS-CoV-2 antibody fragment) can be an Fab. In some cases, an antibody domain provided herein (e.g., an anti-SARS-CoV-2 antibody domain) can be a VH domain.

In one embodiment, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (i) a heavy chain variable domain having a CDR1 having the amino acid sequence set forth in SEQ ID NO:1 (or a variant of SEQ ID NO:1 with one or two amino acid modifications), a CDR2 having the amino acid sequence set forth in SEQ ID NO:2 (or a variant of SEQ ID NO:2 with one or two amino acid modifications), and a CDR3 having the amino acid sequence set forth in SEQ ID NO:3 (or a variant of SEQ ID NO:3 with one or two amino acid modifications); and/or (ii) a light chain variable domain having a CDR1 having the amino acid sequence set forth in SEQ ID NO:9 (or a variant of SEQ ID NO:9 with one or two amino acid modifications), a CDR2 having the amino acid sequence set forth in SEQ ID NO:10 (or a variant of SEQ ID NO:10 with one or two amino acid modifications), and a CDR3 having the amino acid sequence set forth SEQ ID NO:11 (or a variant of SEQ ID NO:11 with one or two amino acid modifications). An example of such an antigen binding fragment having these CDRs and the ability to bind to a SARS-CoV-2 antigen (e.g., the S protein of SARS-CoV-2 or the RBD of the S protein of SARS-CoV-2) includes, without limitation, the Fab set forth in FIGS. 2A and 2B.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) and (a) a heavy chain variable domain having a CDR1 having the amino acid sequence set forth in SEQ ID NO:1 (or a variant of SEQ ID NO:1 with one or two amino acid modifications), a CDR2 having the amino acid sequence set forth in SEQ ID NO:2 (or a variant of SEQ ID NO:2 with one or two amino acid modifications), and a CDR3 having the amino acid sequence set forth in SEQ ID NO:3 (or a variant of SEQ ID NO:3 with one or two amino acid modifications) and/or (b) a light chain variable domain having a CDR1 having the amino acid sequence set forth in SEQ ID NO:9 (or a variant of SEQ ID NO:9 with one or two amino acid modifications), a CDR2 having the amino acid sequence set forth in SEQ ID NO:10 (or a variant of SEQ ID NO:10 with one or two amino acid modifications), and a CDR3 having the amino acid sequence set forth SEQ ID NO:11 (or a variant of SEQ ID NO:11 with one or two amino acid modifications) can include any appropriate framework regions. For example, such a binder (e.g., an antibody, antigen binding fragment, and/or antibody domain) can include (a) a heavy chain variable domain that includes a framework region 1 having the amino acid sequence set forth in SEQ ID NO:4 (or a variant of SEQ ID NO:4 with one, two, three, four, five, six, seven, eight, nine, ten, or more amino acid modifications), a framework region 2 having the amino acid sequence set forth in SEQ ID NO:5 (or a variant of SEQ ID NO:5 with one, two, three, four, five, six, seven, eight, nine, ten, or more amino acid modifications), a framework region 3 having the amino acid sequence set forth in SEQ ID NO:6 (or a variant of SEQ ID NO:6 with one, two, three, four, five, six, seven, eight, nine, ten, or more amino acid modifications), and a framework region 4 having the amino acid sequence set forth in SEQ ID NO:7 (or a variant of SEQ ID NO:7 with one, two, three, four, five, six, seven, eight, nine, ten, or more amino acid modifications) and/or (b) a light chain variable domain that includes a framework region 1 having the amino acid sequence set forth in SEQ ID NO:12 (or a variant of SEQ ID NO:12 with one, two, three, four, five, six, seven, eight, nine, ten, or more amino acid modifications), a framework region 2 having the amino acid sequence set forth in SEQ ID NO:13 (or a variant of SEQ ID NO:13 with one, two, three, four, five, six, seven, eight, nine, ten, or more amino acid modifications), a framework region 3 having the amino acid sequence set forth in SEQ ID NO:14 (or a variant of SEQ ID NO:14 with one, two, three, four, five, six, seven, eight, nine, ten, or more amino acid modifications), and a framework region 4 having the amino acid sequence set forth in SEQ ID NO:15 (or a variant of SEQ ID NO:15 with one, two, three, four, five, six, seven, eight, nine, ten, or more amino acid modifications).

In some cases, a binder (e.g., an antibody, antigen binding fragment, and/or antibody domain) having any of the CDRs set forth in FIG. 2A or 2B can be designed to include framework regions as set forth in FIGS. 2A and 2B or can be designed to include one or more framework regions from another antibody, antibody fragment, or antibody domain. For example, an Fab can be designed to include the six CDRs set forth in FIGS. 2A and 2B and the framework regions set forth in FIGS. 2A and 2B except that framework region 1 having the amino acid set forth in SEQ ID NO:4 is replaced with a framework region 1 having the amino acid set forth in SEQ ID NO:20, a framework region 1 having the amino acid set forth in SEQ ID NO:36, or a framework region 1 having the amino acid set forth in SEQ ID NO:52. In another example, an Fab can be designed to include the six CDRs set forth in FIGS. 2A and 2B and the framework regions set forth in FIGS. 2A and 2B except that framework region 1 having the amino acid set forth in SEQ ID NO:12 is replaced with a framework region 1 having the amino acid set forth in SEQ ID NO:28, a framework region 1 having the amino acid set forth in SEQ ID NO:44, or a framework region 1 having the amino acid set forth in SEQ ID NO:60. In another example, a scFv can be designed to include the six CDRs set forth in FIGS. 2A and 2B and the framework regions set forth in FIGS. 4A and 4B or the framework regions set forth in FIGS. 5A and 5B.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain that includes an amino acid sequence having at least 90 percent identity to the amino acid sequence set forth in SEQ ID NO:8 and/or (b) a light chain variable domain that includes an amino acid sequence having at least 90 percent identity to the amino acid sequence set forth in SEQ ID NO:16. For example, a binder (e.g., an antibody, antigen binding fragment, and/or antibody domain) provided herein can include (a) a heavy chain variable domain that includes an amino acid sequence having at least 90, 91, 92, 93, 94, 95, 96, 97, 98, or 99 percent identity to the amino acid sequence set forth in SEQ ID NO:8 and/or (b) a light chain variable domain that includes an amino acid sequence having at least 90, 91, 92, 93, 94, 95, 96, 97, 98, or 99 percent identity to the amino acid sequence set forth in SEQ ID NO:16. In some cases, a binder (e.g., an antibody, antigen binding fragment, and/or antibody domain) provided herein can include (a) a heavy chain variable domain that includes an amino acid sequence having 100 percent identity to the amino acid sequence set forth in SEQ ID NO:8 and/or (b) a light chain variable domain that includes an amino acid sequence having 100 percent identity to the amino acid sequence set forth in SEQ ID NO:16.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain that includes an amino acid sequence having at least 90 percent identity to the amino acid sequence set forth in SEQ ID NO:8, provided that the heavy chain variable domain includes the amino acid sequences set forth in SEQ ID NOs:1, 2, and 3, and/or (b) a light chain variable domain that includes an amino acid sequence having at least 90 percent identity to the amino acid sequence set forth in SEQ ID NO:16, provided that the light chain variable domain includes the amino acid sequences set forth in SEQ ID NOs:9, 10, and 11. For example, a binder (e.g., an antibody, antigen binding fragment, and/or antibody domain) provided herein can include (a) a heavy chain variable domain that includes an amino acid sequence having at least 90, 91, 92, 93, 94, 95, 96, 97, 98, or 99 percent identity to the amino acid sequence set forth in SEQ ID NO:8, provided that the heavy chain variable domain includes the amino acid sequences set forth in SEQ ID NOs:1, 2, and 3, and/or (b) a light chain variable domain that includes an amino acid sequence having at least 90, 91, 92, 93, 94, 95, 96, 97, 98, or 99 percent identity to the amino acid sequence set forth in SEQ ID NO:16, provided that the light chain variable domain includes the amino acid sequences set forth in SEQ ID NOs:9, 10, and 11.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain having the amino acid sequence set forth in SEQ ID NO:8 or the amino acid set forth in SEQ ID NO:8 with one, two, three, four, five, six, seven, eight, nine, or 10 amino acid modifications (e.g., amino acid substitutions, amino acid deletions, and/or amino acid additions) and/or (b) a light chain variable domain that includes the amino acid sequence set forth in SEQ ID NO:16 or the amino acid set forth in SEQ ID NO:16 with one, two, three, four, five, six, seven, eight, nine, or 10 amino acid modifications (e.g., amino acid substitutions, amino acid deletions, and/or amino acid additions). For example, an antibody or antigen binding fragment provided herein can have the ability to bind to the RBD of the S protein of SARS-CoV-2, can include a heavy chain variable domain having the amino acid sequence set forth in SEQ ID NO:8 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:1, 2, and 3, and can include a light chain variable domain having the amino acid sequence set forth in SEQ ID NO:16 with one, two, three, four, five, six, seven, eight, nine, or 10 amino acid modifications (e.g., amino acid substitutions, amino acid deletions, and/or amino acid additions), provided that the light chain variable domain includes the amino acid sequences set forth in SEQ ID NOs:9, 10, and 11.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain comprising (i) a CDR1 that comprises, consists essentially of, or consists of the amino acid sequence set forth in SEQ ID NO:1, (ii) a CDR2 that comprises, consists essentially of, or consists of the amino acid sequence set forth in SEQ ID NO:2, and (iii) a CDR3 that comprises, consists essentially of, or consists of the amino acid sequence set forth in SEQ ID NO:3, and/or (b) a light chain variable domain comprising (i) a CDR1 that comprises, consists essentially of, or consists of the amino acid sequence set forth in SEQ ID NO:9, (ii) a CDR2 that comprises, consists essentially of, or consists of the amino acid sequence set forth in SEQ ID NO:10, and (iii) a CDR3 that comprises, consists essentially of, or consists of the amino acid sequence set forth in SEQ ID NO:11. As used herein, a "CDR1 that consists essentially of the amino acid sequence set forth in SEQ ID NO:1" is a CDR1 that has zero, one, or two amino acid substitutions within SEQ ID NO:1, that has zero, one, two, three, four, or five amino acid residues directly preceding SEQ ID NO:1, and/or that has zero, one, two, three, four, or five amino acid residues directly following SEQ ID NO:1, provided that the binder (e.g., antibody, antigen binding fragment, or antibody domain) maintains its basic ability to bind to a SARS-CoV-2 antigen (e.g., the S protein of SARS-CoV-2 or the RBD of the S protein of SARS-CoV-2). Examples of a CDR1 that consists essentially of the amino acid sequence set forth in SEQ ID NO:1 include, without limitation, those set forth in Table 1.

TABLE 1

Exemplary CDR1s that consist essentially of the amino acid sequence set forth in SEQ ID NO:1.

| Sequence | SEQ ID NO: |
| --- | --- |
| SSNYMS | 105 |
| VSSNYMS | 106 |
| TVSSNYMS | 107 |
| FTVSSNYMS | 108 |
| GFTVSSNYMS | 109 |
| GFTVSSNYMEI | 110 |
| GFTFSSNYMS | 111 |
| GLTVSSNYMS | 112 |
| SSNYMG | 113 |
| VSSNYMG | 114 |

As used herein, a "CDR2 that consists essentially of the amino acid sequence set forth in SEQ ID NO:2" is a CDR2 that has zero, one, or two amino acid substitutions within SEQ ID NO:2, that has zero, one, two, three, four, or five amino acid residues directly preceding SEQ ID NO:2, and/or that has zero, one, two, three, four, or five amino acid residues directly following SEQ ID NO:2, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR2 that consists essentially of the amino acid sequence set forth in SEQ ID NO:2 include, without limitation, those set forth in Table 2.

TABLE 2

Exemplary CDR2s that consist essentially of the amino acid sequence set forth in SEQ ID NO:2.

| Sequence | SEQ ID NO: |
|---|---|
| VIYSGGSTYYADSVKSD | 115 |
| VIYSGGSTYYADSVKD | 116 |
| VIYSGGSTYYADSVQG | 117 |
| VIYSGGSTYYADSVQD | 118 |
| VIYSGGSTYYNDSVQD | 119 |
| VIYSGGSTYYNDKVQD | 120 |
| VIYSGGSTYYADSFKS | 121 |
| VIYSGGSTYYADKFKS | 122 |
| VIYSGGSTYYAEKFKS | 123 |
| VIYSGGSTYYAEKVQD | 124 |

As used herein, a "CDR3 that consists essentially of the amino acid sequence set forth in SEQ ID NO:3" is a CDR3 that has zero, one, or two amino acid substitutions within SEQ ID NO:3, that has zero, one, two, three, four, or five amino acid residues directly preceding SEQ ID NO:3, and/or that has zero, one, two, three, four, or five amino acid residues directly following SEQ ID NO:3, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR3 that consists essentially of the amino acid sequence set forth in SEQ ID NO:3 include, without limitation, those set forth in Table 3.

TABLE 3

Exemplary CDR3s that consist essentially of the amino acid sequence set forth in SEQ ID NO:3.

| Sequence | SEQ ID NO: |
|---|---|
| AGYGDYYFDY | 125 |
| RGYGDYYFDY | 126 |
| ARGYGDYYFDY | 127 |
| AKGYGDYYFDY | 128 |
| GRGYGDYYFDY | 129 |
| TRGYGDYYFDY | 130 |
| SRGYGDYYFDY | 131 |
| ERGYGDYYFDY | 132 |
| ASGYGDYYFDY | 133 |
| ATGYGDYYFDY | 134 |

As used herein, a "CDR1 that consists essentially of the amino acid sequence set forth in SEQ ID NO:9" is a CDR1 that has zero, one, or two amino acid substitutions within SEQ ID NO:9, that has zero, one, two, three, four, or five amino acid residues directly preceding SEQ ID NO:9, and/or that has zero, one, two, three, four, or five amino acid residues directly following SEQ ID NO:9, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR1 that consists essentially of the amino acid sequence set forth in SEQ ID NO:9 include, without limitation, those set forth in Table 4.

TABLE 4

Exemplary CDR1s that consist essentially of the amino acid sequence set forth in SEQ ID NO:9.

| Sequence | SEQ ID NO: |
|---|---|
| RVSQSVSSYLA | 135 |
| RMSQSVSSYLA | 136 |
| RSSQSVSSYLA | 137 |
| KSSQSVSSYLA | 138 |
| RARQSVSSYLA | 139 |
| RASQSVSSYLH | 140 |
| RASQSVSSYLS | 141 |
| RASQSVSSYLD | 142 |
| RASQSVSSYLN | 143 |
| RASQSVSSYLT | 144 |

As used herein, a "CDR2 that consists essentially of the amino acid sequence set forth in SEQ ID NO:10" is a CDR2 that has zero, one, or two amino acid substitutions within SEQ ID NO:10, that has zero, one, two, three, four, or five amino acid residues directly preceding SEQ ID NO:10, and/or that has zero, one, two, three, four, or five amino acid residues directly following SEQ ID NO:10, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR2 that consists essentially of the amino acid sequence set forth in SEQ ID NO:10 include, without limitation, those set forth in Table 5.

TABLE 5

Exemplary CDR2s that consist essentially of the amino acid sequence set forth in SEQ ID NO:10.

| Sequence | SEQ ID NO: |
|---|---|
| YASTRES | 145 |
| WASTRAS | 146 |
| WASTRET | 147 |
| WASTRAT | 148 |
| DASTRAT | 149 |
| DASTRET | 150 |
| WASTRESG | 151 |
| WASTRESGV | 152 |
| GASTRAT | 153 |
| DASSRAT | 154 |

As used herein, a "CDR3 that consists essentially of the amino acid sequence set forth in SEQ ID NO:11" is a CDR3 that has zero, one, or two amino acid substitutions within SEQ ID NO:11, that has zero, one, two, three, four, or five amino acid residues directly preceding SEQ ID NO:11, and/or that has zero, one, two, three, four, or five amino acid residues directly following SEQ ID NO:11, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR3 that consists essentially of the amino acid sequence set forth in SEQ ID NO:11 include, without limitation, those set forth in Table 6.

TABLE 6

Exemplary CDR3s that consist essentially of the amino acid sequence set forth in SEQ ID NO:11.

| Sequence | SEQ ID NO: |
| --- | --- |
| KQYGSSPLT | 155 |
| LQYGSSPLT | 156 |
| EQYGSSPLT | 157 |
| MQYGSSPLT | 158 |
| TQYGSSPLT | 159 |
| HQYGSSPLT | 160 |
| QKYGSSPLT | 161 |
| QRYGSSPLT | 162 |
| EKYGSSPLT | 163 |
| NQYGSSPLT | 164 |

In another embodiment, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (i) a heavy chain variable domain having a CDR1 having the amino acid sequence set forth in SEQ ID NO:17 (or a variant of SEQ ID NO:17 with one or two amino acid modifications), a CDR2 having the amino acid sequence set forth in SEQ ID NO:18 (or a variant of SEQ ID NO:18 with one or two amino acid modifications), and a CDR3 having the amino acid sequence set forth in SEQ ID NO:19 (or a variant of SEQ ID NO:19 with one or two amino acid modifications); and/or (ii) a light chain variable domain having a CDR1 having the amino acid sequence set forth in SEQ ID NO:25 (or a variant of SEQ ID NO:25 with one or two amino acid modifications), a CDR2 having the amino acid sequence set forth in SEQ ID NO:26 (or a variant of SEQ ID NO:26 with one or two amino acid modifications), and a CDR3 having the amino acid sequence set forth SEQ ID NO:27 (or a variant of SEQ ID NO:27 with one or two amino acid modifications). An example of such an antigen binding fragment having these CDRs and the ability to bind to a SARS-CoV-2 antigen (e.g., the S protein of SARS-CoV-2 or the RBD of the S protein of SARS-CoV-2) includes, without limitation, the Fab set forth in FIGS. 3A and 3B.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) and having (a) a heavy chain variable domain having a CDR1 having the amino acid sequence set forth in SEQ ID NO:17 (or a variant of SEQ ID NO:17 with one or two amino acid modifications), a CDR2 having the amino acid sequence set forth in SEQ ID NO:18 (or a variant of SEQ ID NO:18 with one or two amino acid modifications), and a CDR3 having the amino acid sequence set forth in SEQ ID NO:19 (or a variant of SEQ ID NO:19 with one or two amino acid modifications) and/or (b) a light chain variable domain having a CDR1 having the amino acid sequence set forth in SEQ ID NO:25 (or a variant of SEQ ID NO:25 with one or two amino acid modifications), a CDR2 having the amino acid sequence set forth in SEQ ID NO:26 (or a variant of SEQ ID NO:26 with one or two amino acid modifications), and a CDR3 having the amino acid sequence set forth SEQ ID NO:27 (or a variant of SEQ ID NO:27 with one or two amino acid modifications) can include any appropriate framework regions. For example, such a binder (e.g., an antibody, antigen binding fragment, and/or antibody domain) can include (a) a heavy chain variable domain that includes a framework region 1 having the amino acid sequence set forth in SEQ ID NO:20 (or a variant of SEQ ID NO:20 with one, two, three, four, five, six, seven, eight, nine, ten, or more amino acid modifications), a framework region 2 having the amino acid sequence set forth in SEQ ID NO:21 (or a variant of SEQ ID NO:21 with one, two, three, four, five, six, seven, eight, nine, ten, or more amino acid modifications), a framework region 3 having the amino acid sequence set forth in SEQ ID NO:22 (or a variant of SEQ ID NO:22 with one, two, three, four, five, six, seven, eight, nine, ten, or more amino acid modifications), and a framework region 4 having the amino acid sequence set forth in SEQ ID NO:23 (or a variant of SEQ ID NO:23 with one, two, three, four, five, six, seven, eight, nine, ten, or more amino acid modifications) and/or (b) a light chain variable domain that includes a framework region 1 having the amino acid sequence set forth in SEQ ID NO:28 (or a variant of SEQ ID NO:28 with one, two, three, four, five, six, seven, eight, nine, ten, or more amino acid modifications), a framework region 2 having the amino acid sequence set forth in SEQ ID NO:29 (or a variant of SEQ ID NO:29 with one, two, three, four, five, six, seven, eight, nine, ten, or more amino acid modifications), a framework region 3 having the amino acid sequence set forth in SEQ ID NO:30 (or a variant of SEQ ID NO:30 with one, two, three, four, five, six, seven, eight, nine, ten, or more amino acid modifications), and a framework region 4 having the amino acid sequence set forth in SEQ ID NO:31 (or a variant of SEQ ID NO:31 with one, two, three, four, five, six, seven, eight, nine, ten, or more amino acid modifications).

In some cases, a binder (e.g., an antibody, antigen binding fragment, and/or antibody domain) having any of the CDRs set forth in FIG. 3A or 3B can be designed to include framework regions as set forth in FIGS. 3A and 3B or can be designed to include one or more framework regions from another antibody or antibody fragment. For example, an Fab can be designed to include the six CDRs set forth in FIGS. 3A and 3B and the framework regions set forth in FIGS. 3A and 3B except that framework region 1 having the amino acid set forth in SEQ ID NO:20 is replaced with a framework region 1 having the amino acid set forth in SEQ ID NO:4, a framework region 1 having the amino acid set forth in SEQ ID NO:36, or a framework region 1 having the amino acid set forth in SEQ ID NO:52. In another example, an Fab can be designed to include the six CDRs set forth in FIGS. 3A and 3B and the framework regions set forth in FIGS. 3A and 3B except that framework region 1 having the amino acid set forth in SEQ ID NO:28 is replaced with a framework region 1 having the amino acid set forth in SEQ ID NO:12, a framework region 1 having the amino acid set forth in SEQ ID NO:44, or a framework region 1 having the amino acid set forth in SEQ ID NO:60. In another example, a scFv can be designed to include the six CDRs set forth in FIGS. 3A and 3B and the framework regions set forth in FIGS. 4A and 4B or the framework regions set forth in FIGS. 5A and 5B.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain that includes an amino acid sequence having at least 90 percent identity to the amino acid sequence set forth in SEQ ID NO:24 and/or (b) a light chain variable domain that includes an amino acid sequence having at least 90 percent identity to the amino acid sequence set forth in SEQ ID NO:32. For example, a binder (e.g., an antibody, antigen binding fragment, and/or antibody domain) provided herein can include (a) a heavy chain variable domain that includes an amino acid sequence having at least 90, 91, 92, 93, 94, 95, 96, 97, 98, or 99 percent identity to the amino acid sequence set forth in SEQ ID NO:24 and/or (b) a light chain variable domain that includes an amino acid sequence having at least 90, 91, 92, 93, 94, 95, 96, 97, 98, or 99 percent identity to the amino acid sequence set forth in SEQ ID NO:32. In some cases, a binder (e.g., an antibody, antigen binding fragment, and/or antibody domain) provided herein can include (a) a heavy chain variable domain that includes an amino acid sequence having 100 percent identity to the amino acid sequence set forth in SEQ ID NO:24 and/or (b) a light chain variable domain that includes an amino acid sequence having 100 percent identity to the amino acid sequence set forth in SEQ ID NO:32.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain that includes an amino acid sequence having at least 90 percent identity to the amino acid sequence set forth in SEQ ID NO:24, provided that the heavy chain variable domain includes the amino acid sequences set forth in SEQ ID NOs:17, 18, and 19, and/or (b) a light chain variable domain that includes an amino acid sequence having at least 90 percent identity to the amino acid sequence set forth in SEQ ID NO:32, provided that the light chain variable domain includes the amino acid sequences set forth in SEQ ID NOs:25, 26, and 27. For example, a binder (e.g., an antibody, antigen binding fragment, and/or antibody domain) provided herein can include (a) a heavy chain variable domain that includes an amino acid sequence having at least 90, 91, 92, 93, 94, 95, 96, 97, 98, or 99 percent identity to the amino acid sequence set forth in SEQ ID NO:24, provided that the heavy chain variable domain includes the amino acid sequences set forth in SEQ ID NOs:17, 18, and 19, and/or (b) a light chain variable domain that includes an amino acid sequence having at least 90, 91, 92, 93, 94, 95, 96, 97, 98, or 99 percent identity to the amino acid sequence set forth in SEQ ID NO:32, provided that the light chain variable domain includes the amino acid sequences set forth in SEQ ID NOs:25, 26, and 27.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain having the amino acid sequence set forth in SEQ ID NO:24 or the amino acid set forth in SEQ ID NO:24 with one, two, three, four, five, six, seven, eight, nine, or 10 amino acid modifications (e.g., amino acid substitutions, amino acid deletions, and/or amino acid additions) and/or (b) a light chain variable domain that includes the amino acid sequence set forth in SEQ ID NO:32 or the amino acid set forth in SEQ ID NO:32 with one, two, three, four, five, six, seven, eight, nine, or 10 amino acid modifications (e.g., amino acid substitutions, amino acid deletions, and/or amino acid additions). For example, an antibody or antigen binding fragment provided herein can have the ability to bind to the RBD of the S protein of SARS-CoV-2, can include a heavy chain variable domain having the amino acid sequence set forth in SEQ ID NO:24 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:17, 18, and 19, and can include a light chain variable domain having the amino acid sequence set forth in SEQ ID NO:32 with one, two, three, four, five, six, seven, eight, nine, or 10 amino acid modifications (e.g., amino acid substitutions, amino acid deletions, and/or amino acid additions), provided that the light chain variable domain includes the amino acid sequences set forth in SEQ ID NOs:25, 26, and 27.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain comprising (i) a CDR1 that comprises, consists essentially of, or consists of the amino acid sequence set forth in SEQ ID NO:17, (ii) a CDR2 that comprises, consists essentially of, or consists of the amino acid sequence set forth in SEQ ID NO:18, and (iii) a CDR3 that comprises, consists essentially of, or consists of the amino acid sequence set forth in SEQ ID NO:19, and/or (b) a light chain variable domain comprising (i) a CDR1 that comprises, consists essentially of, or consists of the amino acid sequence set forth in SEQ ID NO:25, (ii) a CDR2 that comprises, consists essentially of, or consists of the amino acid sequence set forth in SEQ ID NO:26, and (iii) a CDR3 that comprises, consists essentially of, or consists of the amino acid sequence set forth in SEQ ID NO:27. As used herein, a "CDR1 that consists essentially of the amino acid sequence set forth in SEQ ID NO:17" is a CDR1 that has zero, one, or two amino acid substitutions within SEQ ID NO:17, that has zero, one, two, three, four, or five amino acid residues directly preceding SEQ ID NO:17, and/or that has zero, one, two, three, four, or five amino acid residues directly following SEQ ID NO:17, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR1 that consists essentially of the amino acid sequence set forth in SEQ ID NO:17 include, without limitation, those set forth in Table 7.

TABLE 7

Exemplary CDR1s that consist essentially of the amino acid sequence set forth in SEQ ID NO:17.

| Sequence | SEQ ID NO: |
| --- | --- |
| GDSVSSNSAAWN | 165 |
| DSVSSNSAAWN | 166 |
| SVSSNSAAWN | 167 |
| VSSNSAAWN | 168 |
| SSNSAAWN | 169 |
| GGSVSSNSAAWN | 170 |
| GDSVSSISAAWN | 171 |
| SISAAWN | 172 |
| GGSVSSISAAWN | 173 |
| GYSVSSISAAWN | 174 |

As used herein, a "CDR2 that consists essentially of the amino acid sequence set forth in SEQ ID NO:18" is a CDR2 that has zero, one, or two amino acid substitutions within SEQ ID NO:18, that has zero, one, two, three, four, or five amino acid residues directly preceding SEQ ID NO:18, and/or that has zero, one, two, three, four, or five amino acid residues directly following SEQ ID NO:18, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR2 that consists essentially of the amino acid sequence set forth in SEQ ID NO:18 include, without limitation, those set forth in Table 8.

TABLE 8

Exemplary CDR2s that consist essentially of the amino acid sequence set forth in SEQ ID NO:18.

| Sequence | SEQ ID NO: |
| --- | --- |
| ITYYRSKWYNDYAVSVKS | 175 |
| STYYRSKWYNDYAVSVKS | 176 |
| RTYYRSKWYNDYAVSLKS | 177 |
| RTYYRSKWYNDYAVSVKG | 178 |
| RTYYRSKWYNYYAVSVKS | 179 |
| RTYYRSKWYNDYADSVKS | 180 |
| RTYYRSKWYNYYADSVKS | 181 |
| YTYYRSKWYNDYAVSVKS | 182 |
| ETYYRSKWYNDYAVSVKS | 183 |
| DTYYRSKWYNDYAVSVKS | 184 |

As used herein, a "CDR3 that consists essentially of the amino acid sequence set forth in SEQ ID NO:19" is a CDR3 that has zero, one, or two amino acid substitutions within SEQ ID NO:19, that has zero, one, two, three, four, or five amino acid residues directly preceding SEQ ID NO:19, and/or that has zero, one, two, three, four, or five amino acid residues directly following SEQ ID NO:19, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR3 that consists essentially of the amino acid sequence set forth in SEQ ID NO:19 include, without limitation, those set forth in Table 9.

TABLE 9

Exemplary CDR3s that consist essentially of the amino acid sequence set forthin SEQ ID NO:19.

| Sequence | SEQ ID NO: |
| --- | --- |
| REQQQLVPHYYYYGMDV | 185 |
| AREQQQLVPHYYYYGMDV | 186 |
| ATEQQQLVPHYYYYGMDV | 187 |
| AAEQQQLVPHYYYYGMDV | 188 |
| AGEQQQLVPHYYYYGMDV | 189 |
| TREQQQLVPHYYYYGMDV | 190 |
| AREQQQLVPHYYYYGMDV | 191 |
| VREQQQLVPHYYYYGMDV | 192 |
| TREQQQLVPHYYYYGMDV | 193 |
| MREQQQLVPHYYYYGMDV | 194 |

As used herein, a "CDR1 that consists essentially of the amino acid sequence set forth in SEQ ID NO:25" is a CDR1 that has zero, one, or two amino acid substitutions within SEQ ID NO:25, that has zero, one, two, three, four, or five amino acid residues directly preceding SEQ ID NO:25, and/or that has zero, one, two, three, four, or five amino acid residues directly following SEQ ID NO:25, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR1 that consists essentially of the amino acid sequence set forth in SEQ ID NO:25 include, without limitation, those set forth in Table 10.

TABLE 10

Exemplary CDR1s that consist essentially of the amino acid sequence set forth in SEQ ID NO:25.

| Sequence | SEQ ID NO: |
| --- | --- |
| TGTSSDVGGYDNYVS | 195 |
| SGTTSDVGGYNYVS | 196 |
| TGSTSDVGGYNYVS | 197 |
| SGSTSDVGGYNYVS | 198 |
| TGTSSDVGGYNYVS | 199 |
| TGTSSNVGGYNYVS | 200 |
| TGTTSDIGGYNYVS | 201 |
| TGTTSDVGSYNYVS | 202 |
| TGTTSDVGGYDYVS | 203 |
| TGSTSDVGGYDYVS | 204 |

As used herein, a "CDR2 that consists essentially of the amino acid sequence set forth in SEQ ID NO:26" is a CDR2 that has zero, one, or two amino acid substitutions within SEQ ID NO:26, that has zero, one, two, three, four, or five amino acid residues directly preceding SEQ ID NO:26, and/or that has zero, one, two, three, four, or five amino acid residues directly following SEQ ID NO:26, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR2 that consists essentially of the amino acid sequence set forth in SEQ ID NO:26 include, without limitation, those set forth in Table 11.

TABLE 11

Exemplary CDR2s that consist essentially of the amino acid sequence set forth in SEQ ID NO:26.

| Sequence | SEQ ID NO: |
| --- | --- |
| DVSKRPS | 205 |
| EVNKRPS | 206 |
| EVSNRPS | 207 |
| DVSNRPS | 208 |
| EGSKRPS | 209 |
| DNNKRPS | 210 |
| ENNKRPS | 211 |
| QDSKRPS | 212 |
| NVNKRPS | 213 |
| EDSKRPS | 214 |

As used herein, a "CDR3 that consists essentially of the amino acid sequence set forth in SEQ ID NO:27" is a CDR3 that has zero, one, or two amino acid substitutions within SEQ ID NO:27, that has zero, one, two, three, four, or five amino acid residues directly preceding SEQ ID NO:27, and/or that has zero, one, two, three, four, or five amino acid residues directly following SEQ ID NO:27, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR3 that consists essentially of the amino acid sequence set forth in SEQ ID NO:27 include, without limitation, those set forth in Table 12.

TABLE 12

Exemplary CDR3s that consist essentially of the amino acid sequence set forth in SEQ ID NO:27.

| Sequence | SEQ ID NO: |
|---|---|
| SLYTSSSTL | 215 |
| SSYASSSTL | 216 |
| SSYSSSSTL | 217 |
| SSYTSSSTF | 218 |
| SSYTGSSTL | 219 |
| SSYTGSSTF | 220 |
| SLYTSSSTF | 221 |
| SLYASSSTL | 222 |
| SLYASSSTF | 223 |
| SSYAGSSTF | 224 |

In another embodiment, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (i) a heavy chain variable domain having a CDR1 having the amino acid sequence set forth in SEQ ID NO:33 (or a variant of SEQ ID NO:33 with one or two amino acid modifications), a CDR2 having the amino acid sequence set forth in SEQ ID NO:34 (or a variant of SEQ ID NO:34 with one or two amino acid modifications), and a CDR3 having the amino acid sequence set forth in SEQ ID NO:35 (or a variant of SEQ ID NO:35 with one or two amino acid modifications); and/or (ii) a light chain variable domain having a CDR1 having the amino acid sequence set forth in SEQ ID NO:41 (or a variant of SEQ ID NO:41 with one or two amino acid modifications), a CDR2 having the amino acid sequence set forth in SEQ ID NO:41 (or a variant of SEQ ID NO:41 with one or two amino acid modifications), and a CDR3 having the amino acid sequence set forth SEQ ID NO:42 (or a variant of SEQ ID NO:42 with one or two amino acid modifications). An example of such an antibody having these CDRs and the ability to bind to a SARS-CoV-2 antigen (e.g., the S protein of SARS-CoV-2 or the RBD of the S protein of SARS-CoV-2) includes, without limitation, the scFv set forth in FIGS. 4A and 4B.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) and having (a) a heavy chain variable domain having a CDR1 having the amino acid sequence set forth in SEQ ID NO:33 (or a variant of SEQ ID NO:33 with one or two amino acid modifications), a CDR2 having the amino acid sequence set forth in SEQ ID NO:34 (or a variant of SEQ ID NO:34 with one or two amino acid modifications), and a CDR3 having the amino acid sequence set forth in SEQ ID NO:35 (or a variant of SEQ ID NO:35 with one or two amino acid modifications) and/or (b) a light chain variable domain having a CDR1 having the amino acid sequence set forth in SEQ ID NO:41 (or a variant of SEQ ID NO:41 with one or two amino acid modifications), a CDR2 having the amino acid sequence set forth in SEQ ID NO:42 (or a variant of SEQ ID NO:42 with one or two amino acid modifications), and a CDR3 having the amino acid sequence set forth SEQ ID NO:43 (or a variant of SEQ ID NO:43 with one or two amino acid modifications) can include any appropriate framework regions. For example, such a binder (e.g., an antibody, antigen binding fragment, and/or antibody domain) can include (a) a heavy chain variable domain that includes a framework region 1 having the amino acid sequence set forth in SEQ ID NO:36 (or a variant of SEQ ID NO:36 with one, two, three, four, five, six, seven, eight, nine, ten, or more amino acid modifications), a framework region 2 having the amino acid sequence set forth in SEQ ID NO:37 (or a variant of SEQ ID NO:37 with one, two, three, four, five, six, seven, eight, nine, ten, or more amino acid modifications), a framework region 3 having the amino acid sequence set forth in SEQ ID NO:38 (or a variant of SEQ ID NO:38 with one, two, three, four, five, six, seven, eight, nine, ten, or more amino acid modifications), and a framework region 4 having the amino acid sequence set forth in SEQ ID NO:39 (or a variant of SEQ ID NO:39 with one, two, three, four, five, six, seven, eight, nine, ten, or more amino acid modifications) and/or (b) a light chain variable domain that includes a framework region 1 having the amino acid sequence set forth in SEQ ID NO:44 (or a variant of SEQ ID NO:44 with one, two, three, four, five, six, seven, eight, nine, ten, or more amino acid modifications), a framework region 2 having the amino acid sequence set forth in SEQ ID NO:45 (or a variant of SEQ ID NO:45 with one, two, three, four, five, six, seven, eight, nine, ten, or more amino acid modifications), a framework region 3 having the amino acid sequence set forth in SEQ ID NO:46 (or a variant of SEQ ID NO:46 with one, two, three, four, five, six, seven, eight, nine, ten, or more amino acid modifications), and a framework region 4 having the amino acid sequence set forth in SEQ ID NO:47 (or a variant of SEQ ID NO:47 with one, two, three, four, five, six, seven, eight, nine, ten, or more amino acid modifications).

In some cases, a binder (e.g., an antibody, antigen binding fragment, and/or antibody domain) having any of the CDRs set forth in FIG. 4A or 4B can be designed to include framework regions as set forth in FIGS. 4A and 4B or can be designed to include one or more framework regions from another antibody or antibody fragment. For example, a scFv can be designed to include the six CDRs set forth in FIGS. 4A and 4B and the framework regions set forth in FIGS. 4A and 4B except that framework region 1 having the amino acid set forth in SEQ ID NO:36 is replaced with a framework region 1 having the amino acid set forth in SEQ ID NO:4, a framework region 1 having the amino acid set forth in SEQ ID NO:20, or a framework region 1 having the amino acid set forth in SEQ ID NO:52. In another example, a scFv can be designed to include the six CDRs set forth in FIGS. 4A and 4B and the framework regions set forth in FIGS. 4A and 4B except that framework region 1 having the amino acid set forth in SEQ ID NO:44 is replaced with a framework region 1 having the amino acid set forth in SEQ ID NO:12, a framework region 1 having the amino acid set forth in SEQ ID NO:28, or a framework region 1 having the amino acid set forth in SEQ ID NO:60. In another example, an Fab can be designed to include the six CDRs set forth in FIGS. 4A and 4B and the framework regions set forth in FIGS. 2A and 2B or the framework regions set forth in FIGS. 3A and 3B.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain that includes an amino acid sequence having at least 90 percent identity to the amino acid sequence set forth in SEQ ID NO:40 and/or (b) a light chain variable domain that includes an amino acid sequence having at least 90 percent identity to the amino acid sequence set forth in SEQ ID NO:48. For example, a binder (e.g., an antibody, antigen binding fragment, and/or antibody domain) provided herein can include (a) a heavy chain variable domain that includes an amino acid sequence having at least 90, 91, 92, 93, 94, 95, 96, 97, 98, or 99 percent identity to the amino acid sequence set forth in SEQ ID NO:40 and/or (b) a light chain variable domain that includes an amino acid sequence having at least 90, 91, 92, 93, 94, 95, 96, 97, 98, or 99 percent identity to the amino acid sequence set forth in SEQ ID NO:48. In some cases, a binder (e.g., an antibody, antigen binding fragment, and/or antibody domain) provided herein can include (a) a heavy chain variable domain that includes an amino acid sequence having 100 percent identity to the amino acid sequence set forth in SEQ ID NO:40 and/or (b) a light chain variable domain that includes an amino acid sequence having 100 percent identity to the amino acid sequence set forth in SEQ ID NO:48.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain that includes an amino acid sequence having at least 90 percent identity to the amino acid sequence set forth in SEQ ID NO:40, provided that the heavy chain variable domain includes the amino acid sequences set forth in SEQ ID NOs:33, 34, and 35, and/or (b) a light chain variable domain that includes an amino acid sequence having at least 90 percent identity to the amino acid sequence set forth in SEQ ID NO:48, provided that the light chain variable domain includes the amino acid sequences set forth in SEQ ID NOs:41, 42, and 43. For example, a binder (e.g., an antibody, antigen binding fragment, and/or antibody domain) provided herein can include (a) a heavy chain variable domain that includes an amino acid sequence having at least 90, 91, 92, 93, 94, 95, 96, 97, 98, or 99 percent identity to the amino acid sequence set forth in SEQ ID NO:40, provided that the heavy chain variable domain includes the amino acid sequences set forth in SEQ ID NOs:33, 34, and 35, and/or (b) a light chain variable domain that includes an amino acid sequence having at least 90, 91, 92, 93, 94, 95, 96, 97, 98, or 99 percent identity to the amino acid sequence set forth in SEQ ID NO:48, provided that the light chain variable domain includes the amino acid sequences set forth in SEQ ID NOs:41, 42, and 43.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain having the amino acid sequence set forth in SEQ ID NO:40 or the amino acid set forth in SEQ ID NO:40 with one, two, three, four, five, six, seven, eight, nine, or 10 amino acid modifications (e.g., amino acid substitutions, amino acid deletions, and/or amino acid additions) and/or (b) a light chain variable domain that includes the amino acid sequence set forth in SEQ ID NO:48 or the amino acid set forth in SEQ ID NO:48 with one, two, three, four, five, six, seven, eight, nine, or 10 amino acid modifications (e.g., amino acid substitutions, amino acid deletions, and/or amino acid additions). For example, an antibody or antigen binding fragment provided herein can have the ability to bind to the RBD of the S protein of SARS-CoV-2, can include a heavy chain variable domain having the amino acid sequence set forth in SEQ ID NO:40 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:33, 34, and 35, and can include a light chain variable domain having the amino acid sequence set forth in SEQ ID NO:48 with one, two, three, four, five, six, seven, eight, nine, or 10 amino acid modifications (e.g., amino acid substitutions, amino acid deletions, and/or amino acid additions), provided that the light chain variable domain includes the amino acid sequences set forth in SEQ ID NOs:41, 42, and 43.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain comprising (i) a CDR1 that comprises, consists essentially of, or consists of the amino acid sequence set forth in SEQ ID NO:33, (ii) a CDR2 that comprises, consists essentially of, or consists of the amino acid sequence set forth in SEQ ID NO:34, and (iii) a CDR3 that comprises, consists essentially of, or consists of the amino acid sequence set forth in SEQ ID NO:35 and/or (b) a light chain variable domain comprising (i) a CDR1 that comprises, consists essentially of, or consists of the amino acid sequence set forth in SEQ ID NO:41, (ii) a CDR2 that comprises, consists essentially of, or consists of the amino acid sequence set forth in SEQ ID NO:42, and (iii) a CDR3 that comprises, consists essentially of, or consists of the amino acid sequence set forth in SEQ ID NO:43. As used herein, a "CDR1 that consists essentially of the amino acid sequence set forth in SEQ ID NO:33" is a CDR1 that has zero, one, or two amino acid substitutions within SEQ ID NO:33, that has zero, one, two, three, four, or five amino acid residues directly preceding SEQ ID NO:33, and/or that has zero, one, two, three, four, or five amino acid residues directly following SEQ ID NO:33, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR1 that consists essentially of the amino acid sequence set forth in SEQ ID NO:33 include, without limitation, those set forth in Table 13.

TABLE 13

Exemplary CDR1s that consist essentially of the amino acid sequence set forth in SEQ ID NO:33.

| Sequence | SEQ ID NO: |
| --- | --- |
| GFTFSSYT | 225 |
| GFTFSSYW | 226 |
| GFTFSSYS | 227 |
| GFTFSSYG | 228 |
| GFTFSSSA | 229 |
| GFTFDDYT | 230 |
| GFTFDDYA | 231 |
| GFTFSSYD | 232 |
| GFTFDDYT | 233 |
| GFTFSSSW | 234 |

As used herein, a "CDR2 that consists essentially of the amino acid sequence set forth in SEQ ID NO:34" is a CDR2 that has zero, one, or two amino acid substitutions within SEQ ID NO:34, that has zero, one, two, three, four, or five amino acid residues directly preceding SEQ ID NO:34, and/or that has zero, one, two, three, four, or five amino acid residues directly following SEQ ID NO:34, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR2 that consists essentially of the amino acid sequence set forth in SEQ ID NO:34 include, without limitation, those set forth in Table 14.

TABLE 14

Exemplary CDR2s that consist essentially of the amino acid sequence set forth in SEQ ID NO:34.

| Sequence | SEQ ID NO: |
|---|---|
| ISTDGGSTI | 235 |
| ISSSGSTI | 236 |
| IGTAGDT | 237 |
| ISGSGGST | 238 |
| ISGSGGST | 239 |
| IGTGGDT | 240 |
| ISSNGGST | 241 |
| ISWDGGST | 242 |
| ISSSSSYI | 243 |
| ISGGST | 244 |

As used herein, a "CDR3 that consists essentially of the amino acid sequence set forth in SEQ ID NO:35" is a CDR3 that has zero, one, or two amino acid substitutions within SEQ ID NO:35, that has zero, one, two, three, four, or five amino acid residues directly preceding SEQ ID NO:35, and/or that has zero, one, two, three, four, or five amino acid residues directly following SEQ ID NO:35, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR3 that consists essentially of the amino acid sequence set forth in SEQ ID NO:35 include, without limitation, those set forth in Table 15.

TABLE 15

Exemplary CDR3s that consist essentially of the amino acid sequence set forth in SEQ ID NO:35.

| Sequence | SEQ ID NO: |
|---|---|
| AKRTYYDFWRTYYGMDV | 245 |
| ARTYYDFWRTYYGMDV | 246 |
| VKTYYDFWRTYYGMDV | 247 |
| KKTYYDFWRTYYGMDV | 248 |
| VRTYYDFWRTYYGMDV | 249 |
| TRTYYDFWRTYYGMDV | 250 |
| SRTYYDFWRTYYGMDV | 251 |
| ATTYYDFWRTYYGMDV | 252 |
| AATYYDFWRTYYGMDV | 253 |
| ARRTYYDFWRTYYGMDV | 254 |

As used herein, a "CDR1 that consists essentially of the amino acid sequence set forth in SEQ ID NO:41" is a CDR1 that has zero, one, or two amino acid substitutions within SEQ ID NO:41, that has zero, one, two, three, four, or five amino acid residues directly preceding SEQ ID NO:41, and/or that has zero, one, two, three, four, or five amino acid residues directly following SEQ ID NO:41, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR1 that consists essentially of the amino acid sequence set forth in SEQ ID NO:41 include, without limitation, those set forth in Table 16.

TABLE 16

Exemplary CDR1s that consist essentially of the amino acid sequence set forth in SEQ ID NO:41.

| Sequence | SEQ ID NO: |
|---|---|
| QDISSW | 255 |
| QGISSW | 256 |
| QGISSA | 257 |
| QDISNY | 258 |
| QGISSY | 259 |
| QSISSW | 260 |
| QGISNY | 261 |
| QGIRND | 262 |
| QSISSY | 263 |
| QGISNS | 264 |

As used herein, a "CDR2 that consists essentially of the amino acid sequence set forth in SEQ ID NO:42" is a CDR2 that has zero or one amino acid substitutions within SEQ ID NO:42, that has zero, one, two, three, four, or five amino acid residues directly preceding SEQ ID NO:42, and/or that has zero, one, two, three, four, or five amino acid residues directly following SEQ ID NO:42, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR2 that consists essentially of the amino acid sequence set forth in SEQ ID NO:42 include, without limitation, those set forth in Table 17.

TABLE 17

Exemplary CDR2s that consist essentially of the amino acid sequence set forth in SEQ ID NO:42.

| Sequence | SEQ ID NO: |
|---|---|
| DAS | 265 |
| SAS | 266 |
| DAK | 267 |
| YAS | 268 |
| YASS | 269 |
| YYASS | 270 |
| DAK | 271 |
| DASG | 272 |
| GDAS | 273 |
| SGDAS | 274 |

As used herein, a "CDR3 that consists essentially of the amino acid sequence set forth in SEQ ID NO:43" is a CDR3 that has zero, one, or two amino acid substitutions within SEQ ID NO:43, that has zero, one, two, three, four, or five amino acid residues directly preceding SEQ ID NO:43, and/or that has zero, one, two, three, four, or five amino acid residues directly following SEQ ID NO:43, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR3 that consists essentially of the amino acid sequence set forth in SEQ ID NO:43 include, without limitation, those set forth in Table 18.

TABLE 18

Exemplary CDR3s that consist essentially of the amino acid sequence set forth in SEQ ID NO:43.

| Sequence | SEQ ID NO: |
| --- | --- |
| QQYYSTPYT | 275 |
| QQYYSFPYT | 276 |
| QQYYSYPYT | 277 |
| QQYNSYPYT | 278 |
| QQYYSTPYTS | 279 |
| QQYYSTPYTG | 280 |
| SQQYYSTPYT | 281 |
| GQQYYSTPYT | 282 |
| TQQYYSTPYT | 283 |
| QQYYSTPYTP | 284 |

In another embodiment, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (i) a heavy chain variable domain having a CDR1 having the amino acid sequence set forth in SEQ ID NO:49 (or a variant of SEQ ID NO:49 with one or two amino acid modifications), a CDR2 having the amino acid sequence set forth in SEQ ID NO:50 (or a variant of SEQ ID NO:50 with one or two amino acid modifications), and a CDR3 having the amino acid sequence set forth in SEQ ID NO:51 (or a variant of SEQ ID NO:51 with one or two amino acid modifications) and/or (ii) a light chain variable domain having a CDR1 having the amino acid sequence set forth in SEQ ID NO:57 (or a variant of SEQ ID NO:57 with one or two amino acid modifications), a CDR2 having the amino acid sequence set forth in SEQ ID NO:58 (or a variant of SEQ ID NO:58 with one or two amino acid modifications), and a CDR3 having the amino acid sequence set forth SEQ ID NO:59 (or a variant of SEQ ID NO:59 with one or two amino acid modifications). An example of such an antibody having these CDRs and the ability to bind to a SARS-CoV-2 antigen (e.g., the S protein of SARS-CoV-2 or the RBD of the S protein of SARS-CoV-2) includes, without limitation, the scFv set forth in FIGS. 5A and 5B.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) and having (a) a heavy chain variable domain having a CDR1 having the amino acid sequence set forth in SEQ ID NO:49 (or a variant of SEQ ID NO:49 with one or two amino acid modifications), a CDR2 having the amino acid sequence set forth in SEQ ID NO:50 (or a variant of SEQ ID NO:50 with one or two amino acid modifications), and a CDR3 having the amino acid sequence set forth in SEQ ID NO:51 (or a variant of SEQ ID NO:51 with one or two amino acid modifications) and/or (b) a light chain variable domain having a CDR1 having the amino acid sequence set forth in SEQ ID NO:57 (or a variant of SEQ ID NO:57 with one or two amino acid modifications), a CDR2 having the amino acid sequence set forth in SEQ ID NO:58 (or a variant of SEQ ID NO:58 with one or two amino acid modifications), and a CDR3 having the amino acid sequence set forth SEQ ID NO:59 (or a variant of SEQ ID NO:59 with one or two amino acid modifications) can include any appropriate framework regions. For example, such a binder (e.g., an antibody, antigen binding fragment, and/or antibody domain) can include (a) a heavy chain variable domain that includes a framework region 1 having the amino acid sequence set forth in SEQ ID NO:52 (or a variant of SEQ ID NO:52 with one, two, three, four, five, six, seven, eight, nine, ten, or more amino acid modifications), a framework region 2 having the amino acid sequence set forth in SEQ ID NO:53 (or a variant of SEQ ID NO:53 with one, two, three, four, five, six, seven, eight, nine, ten, or more amino acid modifications), a framework region 3 having the amino acid sequence set forth in SEQ ID NO:54 (or a variant of SEQ ID NO:54 with one, two, three, four, five, six, seven, eight, nine, ten, or more amino acid modifications), and a framework region 4 having the amino acid sequence set forth in SEQ ID NO:55 (or a variant of SEQ ID NO:55 with one, two, three, four, five, six, seven, eight, nine, ten, or more amino acid modifications) and/or (b) a light chain variable domain that includes a framework region 1 having the amino acid sequence set forth in SEQ ID NO:60 (or a variant of SEQ ID NO:60 with one, two, three, four, five, six, seven, eight, nine, ten, or more amino acid modifications), a framework region 2 having the amino acid sequence set forth in SEQ ID NO:61 (or a variant of SEQ ID NO:61 with one, two, three, four, five, six, seven, eight, nine, ten, or more amino acid modifications), a framework region 3 having the amino acid sequence set forth in SEQ ID NO:62 (or a variant of SEQ ID NO:62 with one, two, three, four, five, six, seven, eight, nine, ten, or more amino acid modifications), and a framework region 4 having the amino acid sequence set forth in SEQ ID NO:63 (or a variant of SEQ ID NO:63 with one, two, three, four, five, six, seven, eight, nine, ten, or more amino acid modifications).

In some cases, a binder (e.g., an antibody, antigen binding fragment, and/or antibody domain) having any of the CDRs set forth in FIG. 5A or 5B can be designed to include framework regions as set forth in FIGS. 5A and 5B or can be designed to include one or more framework regions from another antibody or antibody fragment. For example, a scFv can be designed to include the six CDRs set forth in FIGS. 5A and 5B and the framework regions set forth in FIGS. 5A and 5B except that framework region 1 having the amino acid set forth in SEQ ID NO:52 is replaced with a framework region 1 having the amino acid set forth in SEQ ID NO:4, a framework region 1 having the amino acid set forth in SEQ ID NO:20, or a framework region 1 having the amino acid set forth in SEQ ID NO:36. In another example, a scFv can be designed to include the six CDRs set forth in FIGS. 5A and 5B and the framework regions set forth in FIGS. 5A and 5B except that framework region 1 having the amino acid set forth in SEQ ID NO:60 is replaced with a framework region 1 having the amino acid set forth in SEQ ID NO:12, a framework region 1 having the amino acid set forth in SEQ ID NO:28, or a framework region 1 having the amino acid set forth in SEQ ID NO:44. In another example, an Fab can be designed to include the six CDRs set forth in FIGS. 5A and 5B and the framework regions set forth in FIGS. 2A and 2B or the framework regions set forth in FIGS. 3A and 3B.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain that includes an amino acid sequence having at least 90 percent identity to the amino acid sequence set forth in SEQ ID NO:56 and/or (b) a light chain variable domain that includes an amino acid sequence having at least 90 percent identity to the amino acid sequence set forth in SEQ ID NO:64. For example, a binder (e.g., an antibody, antigen binding fragment, and/or antibody domain) provided herein can include (a) a heavy chain variable domain that includes an amino acid sequence having at least 90, 91, 92, 93, 94, 95, 96, 97, 98, or 99 percent identity to the amino acid sequence set forth in SEQ ID NO:56 and/or (b) a light chain variable domain that includes an amino acid sequence having at least 90, 91, 92, 93, 94, 95, 96, 97, 98, or 99 percent identity to the amino acid sequence set forth in SEQ ID NO:64. In some cases, a binder (e.g., an antibody, antigen binding fragment, and/or antibody domain) provided herein can include (a) a heavy chain variable domain that includes an amino acid sequence having 100 percent identity to the amino acid sequence set forth in SEQ ID NO:56 and/or (b) a light chain variable domain that includes an amino acid sequence having 100 percent identity to the amino acid sequence set forth in SEQ ID NO:64.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain that includes an amino acid sequence having at least 90 percent identity to the amino acid sequence set forth in SEQ ID NO:56, provided that the heavy chain variable domain includes the amino acid sequences set forth in SEQ ID NOs:49, 50, and 51, and/or (b) a light chain variable domain that includes an amino acid sequence having at least 90 percent identity to the amino acid sequence set forth in SEQ ID NO:64, provided that the light chain variable domain includes the amino acid sequences set forth in SEQ ID NOs:57, 58, and 59. For example, a binder (e.g., an antibody, antigen binding fragment, and/or antibody domain) provided herein can include (a) a heavy chain variable domain that includes an amino acid sequence having at least 90, 91, 92, 93, 94, 95, 96, 97, 98, or 99 percent identity to the amino acid sequence set forth in SEQ ID NO:56, provided that the heavy chain variable domain includes the amino acid sequences set forth in SEQ ID NOs:49, 50, and 51, and/or (b) a light chain variable domain that includes an amino acid sequence having at least 90, 91, 92, 93, 94, 95, 96, 97, 98, or 99 percent identity to the amino acid sequence set forth in SEQ ID NO:64, provided that the light chain variable domain includes the amino acid sequences set forth in SEQ ID NOs:57, 58, and 59.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain having the amino acid sequence set forth in SEQ ID NO:56 or the amino acid set forth in SEQ ID NO:56 with one, two, three, four, five, six, seven, eight, nine, or 10 amino acid modifications (e.g., amino acid substitutions, amino acid deletions, and/or amino acid additions) and/or (b) a light chain variable domain that includes the amino acid sequence set forth in SEQ ID NO:64 or the amino acid set forth in SEQ ID NO:64 with one, two, three, four, five, six, seven, eight, nine, or 10 amino acid modifications (e.g., amino acid substitutions, amino acid deletions, and/or amino acid additions). For example, an antibody or an antigen binding fragment provided herein can have the ability to bind to the RBD of the S protein of SARS-CoV-2, can include a heavy chain variable domain having the amino acid sequence set forth in SEQ ID NO:56 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:49, 50, and 51, and can include a light chain variable domain having the amino acid sequence set forth in SEQ ID NO:64 with one, two, three, four, five, six, seven, eight, nine, or 10 amino acid modifications (e.g., amino acid substitutions, amino acid deletions, and/or amino acid additions), provided that the light chain variable domain includes the amino acid sequences set forth in SEQ ID NOs:57, 58, and 59.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include (a) a heavy chain variable domain comprising (i) a CDR1 that comprises, consists essentially of, or consists of the amino acid sequence set forth in SEQ ID NO:49, (ii) a CDR2 that comprises, consists essentially of, or consists of the amino acid sequence set forth in SEQ ID NO:50, and (iii) a CDR3 that comprises, consists essentially of, or consists of the amino acid sequence set forth in SEQ ID NO:51 and/or (b) a light chain variable domain comprising (i) a CDR1 that comprises, consists essentially of, or consists of the amino acid sequence set forth in SEQ ID NO:57, (ii) a CDR2 that comprises, consists essentially of, or consists of the amino acid sequence set forth in SEQ ID NO:58, and (iii) a CDR3 that comprises, consists essentially of, or consists of the amino acid sequence set forth in SEQ ID NO:59. As used herein, a "CDR1 that consists essentially of the amino acid sequence set forth in SEQ ID NO:49" is a CDR1 that has zero, one, or two amino acid substitutions within SEQ ID NO:49, that has zero, one, two, three, four, or five amino acid residues directly preceding SEQ ID NO:49, and/or that has zero, one, two, three, four, or five amino acid residues directly following SEQ ID NO:49, provided that the binder (e.g., the antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR1 that consists essentially of the amino acid sequence set forth in SEQ ID NO:49 include, without limitation, those set forth in Table 19.

TABLE 19

Exemplary CDR1s that consist essentially of the amino acid sequence set forth in SEQ ID NO:49.

| Sequence | SEQ ID NO: |
|---|---|
| GFSFSNYY | 285 |
| GFTFSDYY | 286 |
| GFTFSNAW | 287 |
| GFTFDDYG | 288 |
| GFTFSSYA | 289 |
| GFTVSSNE | 290 |
| GFTVSSNY | 291 |
| GFTFSSYS | 292 |
| GFTFSSYG | 293 |
| GFTFSYYY | 294 |

As used herein, a "CDR2 that consists essentially of the amino acid sequence set forth in SEQ ID NO:50" is a CDR2 that has zero, one, or two amino acid substitutions within SEQ ID NO:50, that has zero, one, two, three, four, or five amino acid residues directly preceding SEQ ID NO:50, and/or that has zero, one, two, three, four, or five amino acid residues directly following SEQ ID NO:50, provided that the binder (e.g., the antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR2 that consists essentially of the amino acid sequence set forth in SEQ ID NO:50 include, without limitation, those set forth in Table 20.

TABLE 20

Exemplary CDR2s that consist essentially of the amino acid sequence set forth in SEQ ID NO:50.

| Sequence | SEQ ID NO: |
| --- | --- |
| IAGSGDYT | 295 |
| ISSSGSTI | 296 |
| VSWNGSRT | 297 |
| INWNGGST | 298 |
| ISSSSSYI | 299 |
| ISGSGGST | 300 |
| ISYDGSNK | 301 |
| IWYDGSNK | 302 |
| ISWDGGST | 303 |
| IGTGGDT | 304 |

As used herein, a "CDR3 that consists essentially of the amino acid sequence set forth in SEQ ID NO:51" is a CDR3 that has zero, one, or two amino acid substitutions within SEQ ID NO:51, that has zero, one, two, three, four, or five amino acid residues directly preceding SEQ ID NO:51, and/or that has zero, one, two, three, four, or five amino acid residues directly following SEQ ID NO:51, provided that the binder (e.g., the antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR3 that consists essentially of the amino acid sequence set forth in SEQ ID NO:51 include, without limitation, those set forth in Table 21.

TABLE 21

Exemplary CDR3s that consist essentially of the amino acid sequence set forth in SEQ ID NO:51.

| Sequence | SEQ ID NO: |
| --- | --- |
| TSRDRYYTMDV | 305 |
| TRDRYYTMDV | 306 |
| VRDRYYTMDV | 307 |
| AKDRYYTMDV | 308 |
| SRDRYYTMDV | 309 |
| TTDRYYTMDV | 310 |
| TGDRYYTMDV | 311 |
| ARYDRYYTMDV | 312 |
| KKDRYYTMDV | 313 |
| VKDRYYTMDV | 314 |

As used herein, a "CDR1 that consists essentially of the amino acid sequence set forth in SEQ ID NO:57" is a CDR1 that has zero, one, or two amino acid substitutions within SEQ ID NO:57, that has zero, one, two, three, four, or five amino acid residues directly preceding SEQ ID NO:57, and/or that has zero, one, two, three, four, or five amino acid residues directly following SEQ ID NO:57, provided that the binder (e.g., the antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR1 that consists essentially of the amino acid sequence set forth in SEQ ID NO:57 include, without limitation, those set forth in Table 22.

TABLE 22

Exemplary CDR1s that consist essentially of the amino acid sequence set forth in SEQ ID NO:57.

| Sequence | SEQ ID NO: |
| --- | --- |
| SSDVGSYDY | 315 |
| SSDVGGYNY | 316 |
| SSDVGSYNR | 317 |
| SSDVGSYNL | 318 |
| SSDVGDYDH | 319 |
| SSDIGGYDL | 320 |
| SSDVGSYDYG | 321 |
| GSSDVGSYDY | 322 |
| VSSDVGSYDY | 323 |
| SSDVGSYDYV | 324 |

As used herein, a "CDR2 that consists essentially of the amino acid sequence set forth in SEQ ID NO:58" is a CDR2 that has zero or one amino acid substitutions within SEQ ID NO:58, that has zero, one, two, three, four, or five amino acid residues directly preceding SEQ ID NO:58, and/or that has zero, one, two, three, four, or five amino acid residues directly following SEQ ID NO:58, provided that the binder (e.g., the antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR2 that consists essentially of the amino acid sequence set forth in SEQ ID NO:58 include, without limitation, those set forth in Table 23.

TABLE 23

Exemplary CDR2s that consist essentially of the amino acid sequence set forth in SEQ ID NO:58.

| Sequence | SEQ ID NO: |
| --- | --- |
| DVS | 325 |
| EGS | 326 |
| NVN | 327 |
| DVA | 328 |
| DVG | 329 |
| DVSQ | 330 |
| QDVS | 331 |
| GDVS | 332 |
| DVSD | 333 |
| DVSG | 334 |

As used herein, a "CDR3 that consists essentially of the amino acid sequence set forth in SEQ ID NO:59" is a CDR3 that has zero, one, or two amino acid substitutions within SEQ ID NO:59, that has zero, one, two, three, four, or five amino acid residues directly preceding SEQ ID NO:59, and/or that has zero, one, two, three, four, or five amino acid residues directly following SEQ ID NO:59, provided that the binder (e.g., the antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR3 that consists essentially of the amino acid sequence set forth in SEQ ID NO:59 include, without limitation, those set forth in Table 24.

TABLE 24

Exemplary CDR3s that consist essentially of the amino acid sequence set forth in SEQ ID NO:59.

| Sequence | SEQ ID NO: |
| --- | --- |
| CSYDSSLSGSL | 335 |
| SSYDSSLSGSL | 336 |
| SSYDSSLSGSL | 337 |
| SLYDSSLSGSL | 338 |
| CQSYDSSLSGSL | 339 |
| SQSYDSSLSGSL | 340 |
| QSYDSSNSGSL | 341 |
| CSYDSSLSGSLG | 342 |
| CSYDSSLSGSLQ | 343 |
| GCSYDSSLSGSL | 344 |

When designing a single chain antibody (e.g., a scFv) having a heavy chain variable domain and a light chain variable domain, the two regions can be directly connected or can be connected using any appropriate linker sequence. For example, the heavy chain variable domain of FIG. 4A can be directly connected to the light chain variable domain of FIG. 4B, or the heavy chain variable domain of FIG. 4A can be connected to the light chain variable domain of FIG. 4B via a linger sequence. In another example, the heavy chain variable domain of FIG. 5A can be directly connected to the light chain variable domain of FIG. 5B, or the heavy chain variable domain of FIG. 5A can be connected to the light chain variable domain of FIG. 5B via a linger sequence. Examples of linker sequences that can be used to connect a heavy chain variable domain and a light chain variable domain to create a scFv include, without limitation, those linkers set forth in FIG. 4C.

In another embodiment, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain having a CDR1 having the amino acid sequence set forth in SEQ ID NO:65 (or a variant of SEQ ID NO:65 with one or two amino acid modifications), a CDR2 having the amino acid sequence set forth in SEQ ID NO:66 (or a variant of SEQ ID NO:66 with one or two amino acid modifications), and a CDR3 having the amino acid sequence set forth in SEQ ID NO:67 (or a variant of SEQ ID NO:67 with one or two amino acid modifications). An example of such an antibody domain having these CDRs and the ability to bind to a SARS-CoV-2 antigen (e.g., the S protein of SARS-CoV-2 or the RBD of the S protein of SARS-CoV-2) includes, without limitation, the VH domain set forth in FIG. 6.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) and having a heavy chain variable domain having a CDR1 having the amino acid sequence set forth in SEQ ID NO:65 (or a variant of SEQ ID NO:65 with one or two amino acid modifications), a CDR2 having the amino acid sequence set forth in SEQ ID NO:66 (or a variant of SEQ ID NO:66 with one or two amino acid modifications), and a CDR3 having the amino acid sequence set forth in SEQ ID NO:67 (or a variant of SEQ ID NO:67 with one or two amino acid modifications) can include any appropriate framework regions. For example, such a binder (e.g., an antibody, antigen binding fragment, and/or antibody domain) can include a heavy chain variable domain that includes a framework region 1 having the amino acid sequence set forth in SEQ ID NO:68 (or a variant of SEQ ID NO:68 with one, two, three, four, five, six, seven, eight, nine, ten, or more amino acid modifications), a framework region 2 having the amino acid sequence set forth in SEQ ID NO:69 (or a variant of SEQ ID NO:69 with one, two, three, four, five, six, seven, eight, nine, ten, or more amino acid modifications), a framework region 3 having the amino acid sequence set forth in SEQ ID NO:70 (or a variant of SEQ ID NO:70 with one, two, three, four, five, six, seven, eight, nine, ten, or more amino acid modifications), and a framework region 4 having the amino acid sequence set forth in SEQ ID NO:71 (or a variant of SEQ ID NO:71 with one, two, three, four, five, six, seven, eight, nine, ten, or more amino acid modifications).

In some cases, a binder (e.g., an antibody, antigen binding fragment, and/or antibody domain) having any of the CDRs set forth in FIG. 6 can be designed to include framework regions as set forth in FIG. 6 or can be designed to include one or more framework regions from another antibody or antibody fragment. For example, an antibody domain (e.g., a VH domain) can be designed to include the three CDRs set forth in FIG. 6 and the framework regions set forth in FIG. 6 except that framework region 1 having the amino acid set forth in SEQ ID NO:68 is replaced with a framework region 1 having the amino acid set forth in SEQ ID NO:76, a framework region 1 having the amino acid set forth in SEQ ID NO:84, a framework region 1 having the amino acid set forth in SEQ ID NO:92, or a framework region 1 having the amino acid set forth in SEQ ID NO:100. In another example, an Fab or scFv can be designed to include (a) the three CDRs set forth in FIG. 6, (b) the framework regions set forth in FIG. 6, 7, 8, 9, or 10, (c) three CDRs of a light chain variable domain provided herein (e.g., SEQ ID NOs:9, 10, and 11; SEQ ID NOs:25, 26, and 27; SEQ ID NOs:41, 42, and 43; or SEQ ID NOs:57, 58, and 59), and (d) the framework regions of a light chain variable domain set forth in FIG. 2B, 3B, 4B, or 5B.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain that includes an amino acid sequence having at least 90 percent identity to the amino acid sequence set forth in SEQ ID NO:72. For example, a binder (e.g., an antibody, antigen binding fragment, and/or antibody domain) provided herein can include a heavy chain variable domain that includes an amino acid sequence having at least 90, 91, 92, 93, 94, 95, 96, 97, 98, or 99 percent identity to the amino acid sequence set forth in SEQ ID NO:72. In some cases, a binder (e.g., an antibody, antigen binding fragment, and/or antibody domain) provided herein can include (a) a heavy chain variable domain that includes an amino acid sequence having 100 percent identity to the amino acid sequence set forth in SEQ ID NO:72.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain that includes an amino acid sequence having at least 90 percent identity to the amino acid sequence set forth in SEQ ID NO:72, provided that the heavy chain variable domain includes the amino acid sequences set forth in SEQ ID NOs:65, 66, and 67. For example, a binder (e.g., an antibody, antigen binding fragment, and/or antibody domain) provided herein can include a heavy chain variable domain that includes an amino acid sequence having at least 90, 91, 92, 93, 94, 95, 96, 97, 98, or 99 percent identity to the amino acid sequence set forth in SEQ ID NO:72, provided that the heavy chain variable domain includes the amino acid sequences set forth in SEQ ID NOs:65, 66, and 67.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain having the amino acid sequence set forth in SEQ ID NO:72 or the amino acid set forth in SEQ ID NO:72 with one, two, three, four, five, six, seven, eight, nine, or 10 amino acid modifications (e.g., amino acid substitutions, amino acid deletions, and/or amino acid additions). For example, antibody domain (e.g., a VH domain) provided herein can have the ability to bind to the RBD of the S protein of SARS-CoV-2 and can include a heavy chain variable domain having the amino acid sequence set forth in SEQ ID NO:72 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:65, 66, and 67.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain comprising (i) a CDR1 that comprises, consists essentially of, or consists of the amino acid sequence set forth in SEQ ID NO:65, (ii) a CDR2 that comprises, consists essentially of, or consists of the amino acid sequence set forth in SEQ ID NO:66, and (iii) a CDR3 that comprises, consists essentially of, or consists of the amino acid sequence set forth in SEQ ID NO:67. As used herein, a "CDR1 that consists essentially of the amino acid sequence set forth in SEQ ID NO:65" is a CDR1 that has zero, one, or two amino acid substitutions within SEQ ID NO:65, that has zero, one, two, three, four, or five amino acid residues directly preceding SEQ ID NO:65, and/or that has zero, one, two, three, four, or five amino acid residues directly following SEQ ID NO:65, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR1 that consists essentially of the amino acid sequence set forth in SEQ ID NO:65 include, without limitation, those set forth in Table 25.

TABLE 25

Exemplary CDR1s that consist essentially of the amino acid sequence set forth in SEQ ID NO:65.

| Sequence | SEQ ID NO: |
| --- | --- |
| GGSFSGYW | 345 |
| GGSISSGGYY | 346 |
| GYSISSGYY | 347 |
| GGSISSSYY | 348 |
| GGSISSSSYY | 349 |
| GYSFTSYW | 350 |
| GGSVSSGSYY | 351 |
| GFTFSSYG | 352 |
| GGSFSGYYWGW | 353 |
| VSGGSFSGYY | 354 |

As used herein, a "CDR2 that consists essentially of the amino acid sequence set forth in SEQ ID NO:66" is a CDR2 that has zero, one, or two amino acid substitutions within SEQ ID NO:66, that has zero, one, two, three, four, or five amino acid residues directly preceding SEQ ID NO:66, and/or that has zero, one, two, three, four, or five amino acid residues directly following SEQ ID NO:66, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR2 that consists essentially of the amino acid sequence set forth in SEQ ID NO:66 include, without limitation, those set forth in Table 26.

TABLE 26

Exemplary CDR2s that consist essentially of the amino acid sequence set forth in SEQ ID NO:66.

| Sequence | SEQ ID NO: |
| --- | --- |
| INHSGSTY | 355 |
| IYHSGST | 356 |
| IYYSGST | 357 |
| IHHSGST | 358 |
| IYSGGST | 359 |
| GYINHSGST | 360 |
| GSINHSGST | 361 |
| INHSGSTYY | 362 |
| GYIYYSGST | 363 |
| GYIYYSGST | 364 |

As used herein, a "CDR3 that consists essentially of the amino acid sequence set forth in SEQ ID NO:67" is a CDR3 that has zero, one, or two amino acid substitutions within SEQ ID NO:67, that has zero, one, two, three, four, or five amino acid residues directly preceding SEQ ID NO:67, and/or that has zero, one, two, three, four, or five amino acid residues directly following SEQ ID NO:67, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR3 that consists essentially of the amino acid sequence set forth in SEQ ID NO:67 include, without limitation, those set forth in Table 27.

TABLE 27

Exemplary CDR3s that consist essentially of the amino acid sequence set forth in SEQ ID NO:67.

| Sequence | SEQ ID NO: |
| --- | --- |
| YYCARLPMIKKSFDI | 365 |
| YCARLPMIKKSFDI | 366 |
| YCCARLPMIKKSFDI | 367 |
| AMYYCARLPMIKKSFDI | 368 |
| AMYYCVRLPMIKKSFDI | 369 |
| YCTRLPMIKKSFDI | 370 |
| YCMRLPMIKKSFDI | 371 |
| YCVKLPMIKKSFDI | 372 |
| YCVSLPMIKKSFDI | 373 |
| YCASLPMIKKSFDI | 374 |

In another embodiment, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain having a CDR1 having the amino acid sequence set forth in SEQ ID NO:73 (or a variant of SEQ ID NO:73 with one or two amino acid modifications), a CDR2 having the amino acid sequence set forth in SEQ ID NO:74 (or a variant of SEQ ID NO:74 with one or two amino acid modifications), and a CDR3 having the amino acid sequence set forth in SEQ ID NO:75 (or a variant of SEQ ID NO:75 with one or two amino acid modifications). An example of such an antibody domain having these CDRs and the ability to bind to a SARS-CoV-2 antigen (e.g., the S protein of SARS-CoV-2 or the RBD of the S protein of SARS-CoV-2) includes, without limitation, the VH domain set forth in FIG. 7.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) and having a heavy chain variable domain having a CDR1 having the amino acid sequence set forth in SEQ ID NO:73 (or a variant of SEQ ID NO:73 with one or two amino acid modifications), a CDR2 having the amino acid sequence set forth in SEQ ID NO:74 (or a variant of SEQ ID NO:74 with one or two amino acid modifications), and a CDR3 having the amino acid sequence set forth in SEQ ID NO:75 (or a variant of SEQ ID NO:75 with one or two amino acid modifications) can include any appropriate framework regions. For example, such a binder (e.g., an antibody, antigen binding fragment, and/or antibody domain) can include a heavy chain variable domain that includes a framework region 1 having the amino acid sequence set forth in SEQ ID NO:76 (or a variant of SEQ ID NO:76 with one, two, three, four, five, six, seven, eight, nine, ten, or more amino acid modifications), a framework region 2 having the amino acid sequence set forth in SEQ ID NO:77 (or a variant of SEQ ID NO:77 with one, two, three, four, five, six, seven, eight, nine, ten, or more amino acid modifications), a framework region 3 having the amino acid sequence set forth in SEQ ID NO:78 (or a variant of SEQ ID NO:78 with one, two, three, four, five, six, seven, eight, nine, ten, or more amino acid modifications), and a framework region 4 having the amino acid sequence set forth in SEQ ID NO:79 (or a variant of SEQ ID NO:79 with one, two, three, four, five, six, seven, eight, nine, ten, or more amino acid modifications).

In some cases, a binder (e.g., an antibody, antigen binding fragment, and/or antibody domain) having any of the CDRs set forth in FIG. 7 can be designed to include framework regions as set forth in FIG. 7 or can be designed to include one or more framework regions from another antibody or antibody fragment. For example, an antibody domain (e.g., a VH domain) can be designed to include the three CDRs set forth in FIG. 7 and the framework regions set forth in FIG. 7 except that framework region 1 having the amino acid set forth in SEQ ID NO:76 is replaced with a framework region 1 having the amino acid set forth in SEQ ID NO:68, a framework region 1 having the amino acid set forth in SEQ ID NO:84, a framework region 1 having the amino acid set forth in SEQ ID NO:92, or a framework region 1 having the amino acid set forth in SEQ ID NO:100. In another example, an Fab or scFv can be designed to include (a) the three CDRs set forth in FIG. 7, (b) the framework regions set forth in FIG. 6, 7, 8, 9, or 10, (c) three CDRs of a light chain variable domain provided herein (e.g., SEQ ID NOs:9, 10, and 11; SEQ ID NOs:25, 26, and 27; SEQ ID NOs:41, 42, and 43; or SEQ ID NOs:57, 58, and 59), and (d) the framework regions of a light chain variable domain set forth in FIG. 2B, 3B, 4B, or 5B.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain that includes an amino acid sequence having at least 90 percent identity to the amino acid sequence set forth in SEQ ID NO:80. For example, a binder (e.g., an antibody, antigen binding fragment, and/or antibody domain) provided herein can include a heavy chain variable domain that includes an amino acid sequence having at least 90, 91, 92, 93, 94, 95, 96, 97, 98, or 99 percent identity to the amino acid sequence set forth in SEQ ID NO:80. In some cases, a binder (e.g., an antibody, antigen binding fragment, and/or antibody domain) provided herein can include (a) a heavy chain variable domain that includes an amino acid sequence having 100 percent identity to the amino acid sequence set forth in SEQ ID NO:80.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain that includes an amino acid sequence having at least 90 percent identity to the amino acid sequence set forth in SEQ ID NO:80, provided that the heavy chain variable domain includes the amino acid sequences set forth in SEQ ID NOs:73, 74, and 75. For example, a binder (e.g., an antibody, antigen binding fragment, and/or antibody domain) provided herein can include a heavy chain variable domain that includes an amino acid sequence having at least 90, 91, 92, 93, 94, 95, 96, 97, 98, or 99 percent identity to the amino acid sequence set forth in SEQ ID NO:80, provided that the heavy chain variable domain includes the amino acid sequences set forth in SEQ ID NOs:73, 74, and 75.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain having the amino acid sequence set forth in SEQ ID NO:80 or the amino acid set forth in SEQ ID NO:80 with one, two, three, four, five, six, seven, eight, nine, or 10 amino acid modifications (e.g., amino acid substitutions, amino acid deletions, and/or amino acid additions). For example, an antibody domain (e.g., a VH domain) provided herein can have the ability to bind to the RBD of the S protein of SARS-CoV-2 and can include a heavy chain variable domain having the amino acid sequence set forth in SEQ ID NO:80 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:73, 74, and 75.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain comprising (i) a CDR1 that comprises, consists essentially of, or consists of the amino acid sequence set forth in SEQ ID NO:73, (ii) a CDR2 that comprises, consists essentially of, or consists of the amino acid sequence set forth in SEQ ID NO:74, and (iii) a CDR3 that comprises, consists essentially of, or consists of the amino acid sequence set forth in SEQ ID NO:75. As used herein, a "CDR1 that consists essentially of the amino acid sequence set forth in SEQ ID NO:73" is a CDR1 that has zero, one, or two amino acid substitutions within SEQ ID NO:73, that has zero, one, two, three, four, or five amino acid residues directly preceding SEQ ID NO:73, and/or that has zero, one, two, three, four, or five amino acid residues directly following SEQ ID NO:73, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR1 that consists essentially of the amino acid sequence set forth in SEQ ID NO:73 include, without limitation, those set forth in Table 28.

TABLE 28

Exemplary CDR1s that consist essentially of the amino acid sequence set forth in SEQ ID NO:73.

| Sequence | SEQ ID NO: |
|---|---|
| GFTFTSYA | 375 |
| GFTFTGYY | 376 |
| GFTFSSYS | 377 |
| GFTFSSYY | 378 |
| GFTFSSYD | 379 |
| GFTFSYYY | 380 |
| GFTFSSYG | 381 |
| QFTFSSYY | 382 |
| GFTFDDYG | 383 |
| GFTFSNSD | 384 |

As used herein, a "CDR2 that consists essentially of the amino acid sequence set forth in SEQ ID NO:74" is a CDR2 that has zero, one, or two amino acid substitutions within SEQ ID NO:74, that has zero, one, two, three, four, or five amino acid residues directly preceding SEQ ID NO:74, and/or that has zero, one, two, three, four, or five amino acid residues directly following SEQ ID NO:74, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR2 that consists essentially of the amino acid sequence set forth in SEQ ID NO:74 include, without limitation, those set forth in Table 29.

TABLE 29

Exemplary CDR2s that consist essentially of the amino acid sequence set forth in SEQ ID NO:74.

| Sequence | SEQ ID NO: |
|---|---|
| IYHDGTT | 385 |
| ISGSGGST | 386 |
| ISGGST | 387 |
| IYSGGST | 388 |
| ISYDGSNK | 389 |
| IYHSGST | 390 |
| IYYSGST | 391 |
| IHHSGST | 392 |
| INHSGST | 393 |
| IWYDGSNK | 394 |

As used herein, a "CDR3 that consists essentially of the amino acid sequence set forth in SEQ ID NO:75" is a CDR3 that has zero, one, or two amino acid substitutions within SEQ ID NO:75, that has zero, one, two, three, four, or five amino acid residues directly preceding SEQ ID NO:75, and/or that has zero, one, two, three, four, or five amino acid residues directly following SEQ ID NO:75, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR3 that consists essentially of the amino acid sequence set forth in SEQ ID NO:75 include, without limitation, those set forth in Table 30.

TABLE 30

Exemplary CDR3s that consist essentially of the amino acid sequence set forth in SEQ ID NO:75.

| Sequence | SEQ ID NO: |
|---|---|
| YARVWLYGSGYMDV | 395 |
| YYYARVWLYGSGYMDV | 396 |
| YYWARVWLYGSGYMDV | 397 |
| YYCVRVWLYGSGYMDV | 398 |
| YYCTRVWLYGSGYMDV | 399 |
| YYCMRVWLYGSGYMDV | 400 |
| YYCATVWLYGSGYMDV | 401 |
| YYCAKVWLYGSGYMDV | 402 |
| YYCASVWLYGSGYMDV | 403 |
| YYCSRVWLYGSGYMDV | 404 |

In another embodiment, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain having a CDR1 having the amino acid sequence set forth in SEQ ID NO:81 (or a variant of SEQ ID NO:81 with one or two amino acid modifications), a CDR2 having the amino acid sequence set forth in SEQ ID NO:82 (or a variant of SEQ ID NO:82 with one or two amino acid modifications), and a CDR3 having the amino acid sequence set forth in SEQ ID NO:83 (or a variant of SEQ ID NO:83 with one or two amino acid modifications). An example of such an antibody having these CDRs and the ability to bind to a SARS-CoV-2 antigen (e.g., the S protein of SARS-CoV-2 or the RBD of the S protein of SARS-CoV-2) includes, without limitation, the VH domain set forth in FIG. 8.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) and having a heavy chain variable domain having a CDR1 having the amino acid sequence set forth in SEQ ID NO:81 (or a variant of SEQ ID NO:81 with one or two amino acid modifications), a CDR2 having the amino acid sequence set forth in SEQ ID NO:82 (or a variant of SEQ ID NO:82 with one or two amino acid modifications), and a CDR3 having the amino acid sequence set forth in SEQ ID NO:83 (or a variant of SEQ ID NO:83 with one or two amino acid modifications) can include any appropriate framework regions. For example, such a binder (e.g., an antibody, antigen binding fragment, and/or antibody domain) can include a heavy chain variable domain that includes a framework region 1 having the amino acid sequence set forth in SEQ ID NO:84 (or a variant of SEQ ID NO:84 with one, two, three, four, five, six, seven, eight, nine, ten, or more amino acid modifications), a framework region 2 having the amino acid sequence set forth in SEQ ID NO:85 (or a variant of SEQ ID NO:85 with one, two, three, four, five, six, seven, eight, nine, ten, or more amino acid modifications), a framework region 3 having the amino acid sequence set forth in SEQ ID NO:86 (or a variant of SEQ ID NO:86 with one, two, three, four, five, six, seven, eight, nine, ten, or more amino acid modifications), and a framework region 4 having the amino acid sequence set forth in SEQ ID NO:87 (or a variant of SEQ ID NO:87 with one, two, three, four, five, six, seven, eight, nine, ten, or more amino acid modifications).

In some cases, a binder (e.g., an antibody, antigen binding fragment, and/or antibody domain) having any of the CDRs set forth in FIG. 8 can be designed to include framework regions as set forth in FIG. 8 or can be designed to include one or more framework regions from another antibody or antibody fragment. For example, an antibody domain (e.g., a VH domain) can be designed to include the three CDRs set forth in FIG. 8 and the framework regions set forth in FIG. 8 except that framework region 1 having the amino acid set forth in SEQ ID NO:84 is replaced with a framework region 1 having the amino acid set forth in SEQ ID NO:68, a framework region 1 having the amino acid set forth in SEQ ID NO:76, a framework region 1 having the amino acid set forth in SEQ ID NO:92, or a framework region 1 having the amino acid set forth in SEQ ID NO:100. In another example, an Fab or scFv can be designed to include (a) the three CDRs set forth in FIG. 8, (b) the framework regions set forth in FIG. 6, 7, 8, 9, or 10, (c) three CDRs of a light chain variable domain provided herein (e.g., SEQ ID NOs:9, 10, and 11; SEQ ID NOs:25, 26, and 27; SEQ ID NOs:41, 42, and 43; or SEQ ID NOs:57, 58, and 59), and (d) the framework regions of a light chain variable domain set forth in FIG. 2B, 3B, 4B, or 5B.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain that includes an amino acid sequence having at least 90 percent identity to the amino acid sequence set forth in SEQ ID NO:88. For example, a binder (e.g., an antibody, antigen binding fragment, and/or antibody domain) provided herein can include a heavy chain variable domain that includes an amino acid sequence having at least 90, 91, 92, 93, 94, 95, 96, 97, 98, or 99 percent identity to the amino acid sequence set forth in SEQ ID NO:88. In some cases, a binder (e.g., an antibody, antigen binding fragment, and/or antibody domain) provided herein can include (a) a heavy chain variable domain that includes an amino acid sequence having 100 percent identity to the amino acid sequence set forth in SEQ ID NO:88.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain that includes an amino acid sequence having at least 90 percent identity to the amino acid sequence set forth in SEQ ID NO:88, provided that the heavy chain variable domain includes the amino acid sequences set forth in SEQ ID NOs:81, 82, and 83. For example, a binder (e.g., an antibody, antigen binding fragment, and/or antibody domain) provided herein can include a heavy chain variable domain that includes an amino acid sequence having at least 90, 91, 92, 93, 94, 95, 96, 97, 98, or 99 percent identity to the amino acid sequence set forth in SEQ ID NO:88, provided that the heavy chain variable domain includes the amino acid sequences set forth in SEQ ID NOs:81, 82, and 83.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain having the amino acid sequence set forth in SEQ ID NO:88 or the amino acid set forth in SEQ ID NO:88 with one, two, three, four, five, six, seven, eight, nine, or 10 amino acid modifications (e.g., amino acid substitutions, amino acid deletions, and/or amino acid additions). For example, a binder (e.g., an antibody, antigen binding fragment, and/or antibody domain) provided herein can have the ability to bind to the RBD of the S protein of SARS-CoV-2 and can include a heavy chain variable domain having the amino acid sequence set forth in SEQ ID NO:88 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:81, 82, and 83.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain comprising (i) a CDR1 that comprises, consists essentially of, or consists of the amino acid sequence set forth in SEQ ID NO:81, (ii) a CDR2 that comprises, consists essentially of, or consists of the amino acid sequence set forth in SEQ ID NO:82, and (iii) a CDR3 that comprises, consists essentially of, or consists of the amino acid sequence set forth in SEQ ID NO:83. As used herein, a "CDR1 that consists essentially of the amino acid sequence set forth in SEQ ID NO:81" is a CDR1 that has zero, one, or two amino acid substitutions within SEQ ID NO:81, that has zero, one, two, three, four, or five amino acid residues directly preceding SEQ ID NO:81, and/or that has zero, one, two, three, four, or five amino acid residues directly following SEQ ID NO:81, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR1 that consists essentially of the amino acid sequence set forth in SEQ ID NO:81 include, without limitation, those set forth in Table 31.

TABLE 31

Exemplary CDR1s that consist essentially of the amino acid sequence set forth in SEQ ID NO:81.

| Sequence | SEQ ID NO: |
|---|---|
| AFDFYDYEMS | 405 |
| FDFYDYEMS | 406 |
| DFYDYEMS | 407 |
| FYDYEMS | 408 |
| YDYEMS | 409 |
| DYEMH | 410 |
| DYEMG | 411 |
| DYAMS | 412 |
| DYGMS | 413 |
| DYYMS | 414 |

As used herein, a "CDR2 that consists essentially of the amino acid sequence set forth in SEQ ID NO:82" is a CDR2 that has zero, one, or two amino acid substitutions within SEQ ID NO:82, that has zero, one, two, three, four, or five amino acid residues directly preceding SEQ ID NO:82, and/or that has zero, one, two, three, four, or five amino acid residues directly following SEQ ID NO:82, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR2 that consists essentially of the amino acid sequence set forth in SEQ ID NO:82 include, without limitation, those set forth in Table 32.

TABLE 32

Exemplary CDR2s that consist essentially of the amino acid sequence set forth in SEQ ID NO:82.

| Sequence | SEQ ID NO: |
|---|---|
| EIHHSGSTYYNPSLKS | 415 |
| SIHHSGSTYYNPSLKG | 416 |
| EIHHSGSTNYNPSLKG | 417 |
| YIHHSGSTYYNPSLKG | 418 |
| YIHHSGSTYYNPSLKS | 419 |
| EINHSGSTYYNPSLKG | 420 |
| EIHYSGSTYYNPSLKG | 421 |
| YIYYSGSTYYNPSLKG | 422 |
| EIHYSGSTYYNPSLKS | 423 |
| EINHSGSTYYNPSLKS | 424 |

As used herein, a "CDR3 that consists essentially of the amino acid sequence set forth in SEQ ID NO:83" is a CDR3 that has zero, one, or two amino acid substitutions within SEQ ID NO:83, that has zero, one, two, three, four, or five amino acid residues directly preceding SEQ ID NO:83, and/or that has zero, one, two, three, four, or five amino acid residues directly following SEQ ID NO:83, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR3 that consists essentially of the amino acid sequence set forth in SEQ ID NO:83 include, without limitation, those set forth in Table 33.

TABLE 33

Exemplary CDR3s that consist essentially of the amino acid sequence set forth in SEQ ID NO:83.

| Sequence | SEQ ID NO: |
|---|---|
| SDVSYHADV | 425 |
| KDVSYHADV | 426 |
| AKDVSYHADV | 427 |
| VKDVSYHADV | 428 |
| ARDVSYHADV | 429 |
| TRDVSYHADV | 430 |
| MRDVSYHADV | 431 |
| SRDVSYHADV | 432 |
| ATDVSYHADV | 433 |
| TTDVSYHADV | 434 |

In another embodiment, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain having a CDR1 having the amino acid sequence set forth in SEQ ID NO:89 (or a variant of SEQ ID NO:89 with one or two amino acid modifications), a CDR2 having the amino acid sequence set forth in SEQ ID NO:90 (or a variant of SEQ ID NO:90 with one or two amino acid modifications), and a CDR3 having the amino acid sequence set forth in SEQ ID NO:91 (or a variant of SEQ ID NO:91 with one or two amino acid modifications). An example of such an antibody domain having these CDRs and the ability to bind to a SARS-CoV-2 antigen (e.g., the S protein of SARS-CoV-2 or the RBD of the S protein of SARS-CoV-2) includes, without limitation, the VH domain set forth in FIG. 9.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) and having a heavy chain variable domain having a CDR1 having the amino acid sequence set forth in SEQ ID NO:89 (or a variant of SEQ ID NO:89 with one or two amino acid modifications), a CDR2 having the amino acid sequence set forth in SEQ ID NO:90 (or a variant of SEQ ID NO:90 with one or two amino acid modifications), and a CDR3 having the amino acid sequence set forth in SEQ ID NO:91 (or a variant of SEQ ID NO:91 with one or two amino acid modifications) can include any appropriate framework regions. For example, such a binder (e.g., an antibody, antigen binding fragment, and/or antibody domain) can include a heavy chain variable domain that includes a framework region 1 having the amino acid sequence set forth in SEQ ID NO:92 (or a variant of SEQ ID NO:92 with one, two, three, four, five, six, seven, eight, nine, ten, or more amino acid modifications), a framework region 2 having the amino acid sequence set forth in SEQ ID NO:93 (or a variant of SEQ ID NO:93 with one, two, three, four, five, six, seven, eight, nine, ten, or more amino acid modifications), a framework region 3 having the amino acid sequence set forth in SEQ ID NO:94 (or a variant of SEQ ID NO:94 with one, two, three, four, five, six, seven, eight, nine, ten, or more amino acid modifications), and a framework region 4 having the amino acid sequence set forth in SEQ ID NO:95 (or a variant of SEQ ID NO:95 with one, two, three, four, five, six, seven, eight, nine, ten, or more amino acid modifications).

In some cases, a binder (e.g., an antibody, antigen binding fragment, and/or antibody domain) having any of the CDRs set forth in FIG. 9 can be designed to include framework regions as set forth in FIG. 9 or can be designed to include one or more framework regions from another antibody or antibody fragment. For example, an antibody domain (e.g., a VH domain) can be designed to include the three CDRs set forth in FIG. 9 and the framework regions set forth in FIG. 9 except that framework region 1 having the amino acid set forth in SEQ ID NO:92 is replaced with a framework region 1 having the amino acid set forth in SEQ ID NO:68, a framework region 1 having the amino acid set forth in SEQ ID NO:76, a framework region 1 having the amino acid set forth in SEQ ID NO:84, or a framework region 1 having the amino acid set forth in SEQ ID NO:100. In another example, an Fab or scFv can be designed to include (a) the three CDRs set forth in FIG. 9, (b) the framework regions set forth in FIG. 6, 7, 8, 9, or 10, (c) three CDRs of a light chain variable domain provided herein (e.g., SEQ ID NOs:9, 10, and 11; SEQ ID NOs:25, 26, and 27; SEQ ID NOs:41, 42, and 43; or SEQ ID NOs:57, 58, and 59), and (d) the framework regions of a light chain variable domain set forth in FIG. 2B, 3B, 4B, or 5B.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain that includes an amino acid sequence having at least 90 percent identity to the amino acid sequence set forth in SEQ ID NO:96. For example, a binder (e.g., an antibody, antigen binding fragment, and/or antibody domain) provided herein can include a heavy chain variable domain that includes an amino acid sequence having at least 90, 91, 92, 93, 94, 95, 96, 97, 98, or 99 percent identity to the amino acid sequence set forth in SEQ ID NO:96. In some cases, a binder (e.g., an antibody, antigen binding fragment, and/or antibody domain) provided herein can include a heavy chain variable domain that includes an amino acid sequence having 100 percent identity to the amino acid sequence set forth in SEQ ID NO:96.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain that includes an amino acid sequence having at least 90 percent identity to the amino acid sequence set forth in SEQ ID NO:96, provided that the heavy chain variable domain includes the amino acid sequences set forth in SEQ ID NOs:89, 90, and 91. For example, a binder (e.g., an antibody, antigen binding fragment, and/or antibody domain) provided herein can include a heavy chain variable domain that includes an amino acid sequence having at least 90, 91, 92, 93, 94, 95, 96, 97, 98, or 99 percent identity to the amino acid sequence set forth in SEQ ID NO:96, provided that the heavy chain variable domain includes the amino acid sequences set forth in SEQ ID NOs:89, 90, and 91.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain having the amino acid sequence set forth in SEQ ID NO:96 or the amino acid set forth in SEQ ID NO:96 with one, two, three, four, five, six, seven, eight, nine, or 10 amino acid modifications (e.g., amino acid substitutions, amino acid deletions, and/or amino acid additions). For example, a binder (e.g., an antibody, antigen binding fragment, and/or antibody domain) provided herein can have the ability to bind to the RBD of the S protein of SARS-CoV-2 and can include a heavy chain variable domain having the amino acid sequence set forth in SEQ ID NO:96 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:89, 90, and 91.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain comprising (i) a CDR1 that comprises, consists essentially of, or consists of the amino acid sequence set forth in SEQ ID NO:89, (ii) a CDR2 that comprises, consists essentially of, or consists of the amino acid sequence set forth in SEQ ID NO:90, and (iii) a CDR3 that comprises, consists essentially of, or consists of the amino acid sequence set forth in SEQ ID NO:91. As used herein, a "CDR1 that consists essentially of the amino acid sequence set forth in SEQ ID NO:89" is a CDR1 that has zero, one, or two amino acid substitutions within SEQ ID NO:89, that has zero, one, two, three, four, or five amino acid residues directly preceding SEQ ID NO:89, and/or that has zero, one, two, three, four, or five amino acid residues directly following SEQ ID NO:89, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR1 that consists essentially of the amino acid sequence set forth in SEQ ID NO:89 include, without limitation, those set forth in Table 34.

TABLE 34

Exemplary CDR1s that consist essentially of the amino acid sequence set forth in SEQ ID NO:89.

| Sequence | SEQ ID NO: |
|---|---|
| GFTFDDYAMS | 435 |
| FTFDDYAMS | 436 |
| TFDDYAMS | 437 |
| FDDYAMS | 438 |
| DDYAMS | 439 |
| DDYEMS | 440 |
| DDYAMEI | 441 |
| DDYAMG | 442 |
| DEYAMS | 443 |
| DDYYMS | 444 |

As used herein, a "CDR2 that consists essentially of the amino acid sequence set forth in SEQ ID NO:90" is a CDR2 that has zero, one, or two amino acid substitutions within SEQ ID NO:90, that has zero, one, two, three, four, or five amino acid residues directly preceding SEQ ID NO:90, and/or that has zero, one, two, three, four, or five amino acid residues directly following SEQ ID NO:90, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR2 that consists essentially of the amino acid sequence set forth in SEQ ID NO:90 include, without limitation, those set forth in Table 35.

TABLE 35

Exemplary CDR2s that consist essentially of the amino acid sequence set forth in SEQ ID NO:90.

| Sequence | SEQ ID NO: |
|---|---|
| RMYNNGRTSYNPSLKG | 445 |
| RMYNNGRTSYNPSLKS | 446 |
| RMYNNGRTYYNPSLKS | 447 |
| KMYNNGRTSYNPSLKS | 448 |
| RMYNNARTSYNPSLKS | 449 |
| RMYNNSRTSYNPSLKS | 450 |
| RMYNNSRTSYNPSLKG | 451 |
| KMYNNGRTSYNPSLKG | 452 |
| RMYNNARTSYNPSLKG | 453 |
| IGRMYNNARTSYNPSLKG | 454 |

As used herein, a "CDR3 that consists essentially of the amino acid sequence set forth in SEQ ID NO:91" is a CDR3 that has zero, one, or two amino acid substitutions within SEQ ID NO:91, that has zero, one, two, three, four, or five amino acid residues directly preceding SEQ ID NO:91, and/or that has zero, one, two, three, four, or five amino acid residues directly following SEQ ID NO:91, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR3 that consists essentially of the amino acid sequence set forth in SEQ ID NO:91 include, without limitation, those set forth in Table 36.

TABLE 36

Exemplary CDR3s that consist essentially of the amino acid sequence set forth in SEQ ID NO:91.

| Sequence | SEQ ID NO: |
| --- | --- |
| ITDNLGYRPSENLYGMDV | 455 |
| RDNLGYRPSENLYGMDV | 456 |
| ARDNLGYRPSENLYGMDV | 457 |
| AKDNLGYRPSENLYGMDV | 458 |
| ATDNLGYRPSENLYGMDV | 459 |
| TTDNLGYRPSENLYGMDV | 460 |
| IRDNLGYRPSENLYGMDV | 461 |
| VRDNLGYRPSENLYGMDV | 462 |
| TRDNLGYRPSENLYGMDV | 463 |
| MRDNLGYRPSENLYGMDV | 464 |

In another embodiment, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain having a CDR1 having the amino acid sequence set forth in SEQ ID NO:97 (or a variant of SEQ ID NO:97 with one or two amino acid modifications), a CDR2 having the amino acid sequence set forth in SEQ ID NO:98 (or a variant of SEQ ID NO:98 with one or two amino acid modifications), and a CDR3 having the amino acid sequence set forth in SEQ ID NO:99 (or a variant of SEQ ID NO:99 with one or two amino acid modifications). An example of such an antibody domain having these CDRs and the ability to bind to a SARS-CoV-2 antigen (e.g., the S protein of SARS-CoV-2 or the RBD of the S protein of SARS-CoV-2) includes, without limitation, the VH domain set forth in FIG. 10.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) and having a heavy chain variable domain having a CDR1 having the amino acid sequence set forth in SEQ ID NO:97 (or a variant of SEQ ID NO:97 with one or two amino acid modifications), a CDR2 having the amino acid sequence set forth in SEQ ID NO:98 (or a variant of SEQ ID NO:98 with one or two amino acid modifications), and a CDR3 having the amino acid sequence set forth in SEQ ID NO:99 (or a variant of SEQ ID NO:99 with one or two amino acid modifications) can include any appropriate framework regions. For example, such a binder (e.g., an antibody, antigen binding fragment, and/or antibody domain) can include a heavy chain variable domain that includes a framework region 1 having the amino acid sequence set forth in SEQ ID NO:100 (or a variant of SEQ ID NO:100 with one, two, three, four, five, six, seven, eight, nine, ten, or more amino acid modifications), a framework region 2 having the amino acid sequence set forth in SEQ ID NO:101 (or a variant of SEQ ID NO:101 with one, two, three, four, five, six, seven, eight, nine, ten, or more amino acid modifications), a framework region 3 having the amino acid sequence set forth in SEQ ID NO:102 (or a variant of SEQ ID NO:102 with one, two, three, four, five, six, seven, eight, nine, ten, or more amino acid modifications), and a framework region 4 having the amino acid sequence set forth in SEQ ID NO:103 (or a variant of SEQ ID NO:103 with one, two, three, four, five, six, seven, eight, nine, ten, or more amino acid modifications).

In some cases, a binder (e.g., an antibody, antigen binding fragment, and/or antibody domain) having any of the CDRs set forth in FIG. 10 can be designed to include framework regions as set forth in FIG. 10 or can be designed to include one or more framework regions from another antibody or antibody fragment. For example, an antibody domain (e.g., a VH domain) can be designed to include the three CDRs set forth in FIG. 10 and the framework regions set forth in FIG. 10 except that framework region 1 having the amino acid set forth in SEQ ID NO:100 is replaced with a framework region 1 having the amino acid set forth in SEQ ID NO:68, a framework region 1 having the amino acid set forth in SEQ ID NO:76, a framework region 1 having the amino acid set forth in SEQ ID NO:84, or a framework region 1 having the amino acid set forth in SEQ ID NO:92. In another example, an Fab or scFv can be designed to include (a) the three CDRs set forth in FIG. 10, (b) the framework regions set forth in FIG. 6, 7, 8, 9, or 10, (c) three CDRs of a light chain variable domain provided herein (e.g., SEQ ID NOs:9, 10, and 11; SEQ ID NOs:25, 26, and 27; SEQ ID NOs:41, 42, and 43; or SEQ ID NOs:57, 58, and 59), and (d) the framework regions of a light chain variable domain set forth in FIG. 2B, 3B, 4B, or 5B.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain that includes an amino acid sequence having at least 90 percent identity to the amino acid sequence set forth in SEQ ID NO:104. For example, a binder (e.g., an antibody, antigen binding fragment, and/or antibody domain) provided herein can include a heavy chain variable domain that includes an amino acid sequence having at least 90, 91, 92, 93, 94, 95, 96, 97, 98, or 99 percent identity to the amino acid sequence set forth in SEQ ID NO:104. In some cases, a binder (e.g., an antibody, antigen binding fragment, and/or antibody domain) provided herein can include a heavy chain variable domain that includes an amino acid sequence having 100 percent identity to the amino acid sequence set forth in SEQ ID NO:104.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain that includes an amino acid sequence having at least 90 percent identity to the amino acid sequence set forth in SEQ ID NO:104, provided that the heavy chain variable domain includes the amino acid sequences set forth in SEQ ID NOs:97, 98, and 99. For example, a binder (e.g., an antibody, antigen binding fragment, and/or antibody domain) provided herein can include a heavy chain variable domain that includes an amino acid sequence having at least 90, 91, 92, 93, 94, 95, 96, 97, 98, or 99 percent identity to the amino acid sequence set forth in SEQ ID NO:104, provided that the heavy chain variable domain includes the amino acid sequences set forth in SEQ ID NOs:97, 98, and 99.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain having the amino acid sequence set forth in SEQ ID NO:104 or the amino acid set forth in SEQ ID NO:104 with one, two, three, four, five, six, seven, eight, nine, or 10 amino acid modifications (e.g., amino acid substitutions, amino acid deletions, and/or amino acid additions). For example, a binder (e.g., an antibody, antigen binding fragment, and/or antibody domain) provided herein can have the ability to bind to the RBD of the S protein of SARS-CoV-2 and can include a heavy chain variable domain having the amino acid sequence set forth in SEQ ID NO:104 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:97, 98, and 99.

In some cases, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can include a heavy chain variable domain comprising (i) a CDR1 that comprises, consists essentially of, or consists of the amino acid sequence set forth in SEQ ID NO:97, (ii) a CDR2 that comprises, consists essentially of, or consists of the amino acid sequence set forth in SEQ ID NO:98, and (iii) a CDR3 that comprises, consists essentially of, or consists of the amino acid sequence set forth in SEQ ID NO:99. As used herein, a "CDR1 that consists essentially of the amino acid sequence set forth in SEQ ID NO:97" is a CDR1 that has zero, one, or two amino acid substitutions within SEQ ID NO:97, that has zero, one, two, three, four, or five amino acid residues directly preceding SEQ ID NO:97, and/or that has zero, one, two, three, four, or five amino acid residues directly following SEQ ID NO:97, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR1 that consists essentially of the amino acid sequence set forth in SEQ ID NO:97 include, without limitation, those set forth in Table 37.

TABLE 37

Exemplary CDR1s that consist essentially of the amino acid sequence set forth in SEQ ID NO:97.

| Sequence | SEQ ID NO: |
| --- | --- |
| GFTLSDYYIG | 465 |
| FTLSDYYIG | 466 |
| TLSDYYIG | 467 |
| LSDYYIG | 468 |
| SDYYIG | 469 |
| GFTFSDYYIG | 470 |
| GFTFSDYYEG | 471 |
| GFTFSDYYIS | 472 |
| GLTFSDYYIG | 473 |
| GFTFSDYYIS | 474 |

As used herein, a "CDR2 that consists essentially of the amino acid sequence set forth in SEQ ID NO:98" is a CDR2 that has zero, one, or two amino acid substitutions within SEQ ID NO:98, that has zero, one, two, three, four, or five amino acid residues directly preceding SEQ ID NO:98, and/or that has zero, one, two, three, four, or five amino acid residues directly following SEQ ID NO:98, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR2 that consists essentially of the amino acid sequence set forth in SEQ ID NO:98 include, without limitation, those set forth in Table 38.

TABLE 38

Exemplary CDR2s that consist essentially of the amino acid sequence set forth in SEQ ID NO:98.

| Sequence | SEQ ID NO: |
| --- | --- |
| SMYHSGRTYINPSLKG | 475 |
| SMYHSGRTYVNPSLKS | 476 |
| SMYHSGRTYVNPSLKG | 477 |
| GMYHSGRTYVNPSLKS | 478 |
| SMYHSGRSYVNPSLKS | 479 |
| SMYHSGRSYVNPSLKG | 480 |
| GMYHSGRSYVNPSLKS | 481 |
| GMYHSGRSYVNPSLKG | 482 |
| SMYHSGKSYVNPSLKS | 483 |
| SMYHSGKSYVNPSLKG | 484 |

As used herein, a "CDR3 that consists essentially of the amino acid sequence set forth in SEQ ID NO:99" is a CDR3 that has zero, one, or two amino acid substitutions within SEQ ID NO:99, that has zero, one, two, three, four, or five amino acid residues directly preceding SEQ ID NO:99, and/or that has zero, one, two, three, four, or five amino acid residues directly following SEQ ID NO:99, provided that the binder (e.g., antibody, antigen binding fragment, and/or antibody domain) maintains its basic ability to bind to a SARS-CoV-2 antigen (e.g., the S protein of SARS-CoV-2 or the RBD of the S protein of SARS-CoV-2). Examples of a CDR3 that consists essentially of the amino acid sequence set forth in SEQ ID NO:99 include, without limitation, those set forth in Table 39.

TABLE 39

Exemplary CDR3s that consist essentially of the amino acid sequence set forth in SEQ ID NO:99.

| Sequence | SEQ ID NO: |
| --- | --- |
| ARGGITGTTPIDY | 485 |
| RGGITGTTPIDY | 486 |
| TRGGITGTTPIDY | 487 |
| VRGGITGTTPIDY | 488 |
| IVIRGGITGTTPIDY | 489 |
| AKGGITGTTPIDY | 490 |
| ATGGITGTTPIDY | 491 |
| TTGGITGTTPIDY | 492 |
| AGGGITGTTPIDY | 493 |
| IRGGITGTTPIDY | 494 |

As indicated herein, the amino acid sequences described herein can include amino acid modifications (e.g., the articulated number of amino acid modifications). Such amino acid modifications can include, without limitation, amino acid substitutions, amino acid deletions, amino acid additions, and combinations. In some cases, an amino acid modification can be made to improve the binding and/or contact with an antigen and/or to improve a functional activity of a binder (e.g., an antibody, antigen binding fragment, and/or antibody domain) provided herein. In some cases, an amino acid substitution within an articulated sequence identifier can be a conservative amino acid substitution. For example, conservative amino acid substitutions can be made by substituting one amino acid residue for another amino acid residue having a similar side chain. Families of amino acid residues having similar side chains can include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

In some cases, an amino acid substitution within an articulated sequence identifier can be a non-conservative amino acid substitution. Non-conservative amino acid substitutions can be made by substituting one amino acid residue for another amino acid residue having a dissimilar side chain. Examples of non-conservative substitutions include, without limitation, substituting (a) a hydrophilic residue (e.g., serine or threonine) for a hydrophobic residue (e.g., leucine, isoleucine, phenylalanine, valine, or alanine); (b) a cysteine or proline for any other residue; (c) a residue having a basic side chain (e.g., lysine, arginine, or histidine) for a residue having an acidic side chain (e.g., aspartic acid or glutamic acid); and (d) a residue having a bulky side chain (e.g., phenylalanine) for glycine or other residue having a small side chain.

Methods for generating an amino acid sequence variant (e.g., an amino acid sequence that includes one or more modifications with respect to an articulated sequence identifier) can include site-specific mutagenesis or random mutagenesis (e.g., by PCR) of a nucleic acid encoding the antibody or fragment thereof. See, for example, Zoller, *Curr Opin. Biotechnol.* 3: 348-354 (1992). Both naturally occurring and non-naturally occurring amino acids (e.g., artificially-derivatized amino acids) can be used to generate an amino acid sequence variant provided herein.

A representative number of binders (e.g., antibodies, antigen binding fragments, and/or antibody domains) having the ability to bind to a SARS-CoV-2 antigen (e.g., the S protein of SARS-CoV-2 or the RBD of the S protein of SARS-CoV-2) are further described in Table 40.

TABLE 40

Representative number of binders.

| Clone # (Antibody type) | SEQ ID NOs of Heavy Chain Variable Domain/Region CDRs | SEQ ID NOs of Heavy Chain Variable Domain/Region Framework Regions | SEQ ID NO of Heavy Chain Variable Domain/ Region | SEQ ID NOs of Light Chain Variable Domain/ Region CDRs | SEQ ID NOs of Light Chain Variable Domain/Region Framework Regions | SEQ ID NO of Light Chain Variable Domain/ Region |
|---|---|---|---|---|---|---|
| #1 (Fab) | 1, 2, 3 | 4, 5, 6, 7 | 8 | 9, 10, 11 | 12, 13, 14, 15 | 16 |
| #2 (Fab) | 17, 18, 19 | 20, 21, 22, 23 | 24 | 25, 26, 27 | 28, 29, 30, 31 | 32 |
| #3 (scFv) | 33, 34, 35 | 36, 37, 38, 39 | 40 | 41, 42, 43 | 44, 45, 46, 47 | 48 |
| #4 (scFv) | 49, 50, 51 | 52, 53, 54, 55 | 56 | 57, 58, 59 | 60, 61, 62, 63 | 64 |
| #5 (VH domain) | 65, 66, 67 | 68, 69, 70, 71 | 72 | | | |
| #6 (VH domain) | 73, 74, 75 | 76, 77, 78, 79 | 80 | | | |
| #7 (VH domain) | 81, 82, 83 | 84, 85, 86, 87 | 88 | | | |
| #8 (VH domain) | 89, 90, 91 | 92, 93, 94, 95 | 96 | | | |
| #9 (VH domain) | 97, 98, 99 | 100, 101, 102, 103 | 104 | | | |

Table 41 includes an alternative designation that can be used to refer to each of Clones #1-#9.

TABLE 41

Alternative nomenclature for Clones #1-#9.

| Clone # | Alternative names |
|---|---|
| 1 | ab1 |
| 2 | ab2 |

TABLE 41-continued

Alternative nomenclature for Clones #1-#9.

| Clone # | Alternative names |
|---|---|
| 3 | ab3 |
| 4 | ab4 |
| 5 | ab5 |
| 6 | ab6 |
| 7 | ab7 |
| 8 | ab8 |
| 9 | ab9 |

The binders (e.g., antibodies, antigen binding fragments, and/or antibody domains) provided herein can be produced using any appropriate method. For example, the binders (e.g., antibodies, antigen binding fragments, and/or antibody domains) provided herein can be produced in recombinant host cells. For example, a nucleic acid encoding a binder (e.g., an antibody, antigen binding fragment, and/or antibody domain) provided herein can be constructed, introduced into an expression vector, and expressed in suitable host cells. FIG. 11 is a sequence listing of nucleic acid sequences encoding exemplary binders (e.g., antibodies, antigen binding fragments, and/or antibody domains) described herein. In some cases, a binder (e.g., an antibody, antigen binding fragment, and/or antibody domain) provided herein can be recombinantly produced in prokaryotic hosts such as *E. coli*, *Bacillus brevis*, *Bacillus subtilis*, *Bacillus megaterium*, *Lactobacillus zeaecasei*, or *Lactobacillus paracasei*. A binder (e.g., an antibody, antigen binding fragment, and/or antibody domain) provided herein also can be recombinantly produced in eukaryotic hosts such as yeast (e.g., *Pichia pastoris, Saccharomyces cerevisiae, Hansenula polymorpha, Schizosaccharomyces pombe, Schwanniomyces occidentalis, Kluyveromyces lactis,* or *Yarrowia lipolytica*), filamentous fungi of the genera *Trichoderma* (e.g., *T. reesei*) and *Aspergillus* (e.g., *A. niger* and *A. oryzae*), protozoa such as *Leishmania tarentolae*, insect cells, or mammalian cells (e.g., mammalian cell lines such as Chinese hamster ovary (CHO) cells, Per.C6 cells, mouse myeloma NS0 cells, baby hamster kidney (BHK) cells, or human embryonic kidney cell line HEK293). See, for example, the Frenzel et al. reference (*Front Immunol.*, 4:217 (2013)).

In some cases, an antigen binding fragment or antibody domain provided herein can be produced by proteolytic digestion of an intact antibody. For example, an antigen binding fragment can be obtained by treating an antibody with an enzyme such as papain or pepsin. Papain digestion of whole antibodies can be used to produce F(ab)$_2$ or Fab fragments, while pepsin digestion of whole antibodies can be used to produce F(ab')$_2$ or Fab' fragments.

In some cases, a binder (e.g., an antibody, antigen binding fragment, and/or antibody domain) provided herein can be substantially pure. The term "substantially pure" as used herein with reference to a binder (e.g., an antibody, antigen binding fragment, and/or antibody domain) refers to the binder (e.g., antibody, antigen binding fragment, and/or antibody domain) as being substantially free of other polypeptides, lipids, carbohydrates, and nucleic acid with which it is naturally associated. Thus, a substantially pure binder (e.g., antibody, antigen binding fragment, and/or antibody domain) provided herein is any binder (e.g., antibody, antigen binding fragment, and/or antibody domain) that is removed from its natural environment and is at least 60 percent pure. A substantially pure binder (e.g., antibody, antigen binding fragment, and/or antibody domain) provided herein can be at least about 65, 70, 75, 80, 85, 90, 95, or 99 percent pure.

This document also provides bispecific binders (e.g., bispecific antibodies, bispecific antigen binding fragments, and/or bispecific antibody domains) that bind to two different epitopes with at least one being an epitope of a SARS-CoV-2 antigen (e.g., the S protein of SARS-CoV-2 or the RBD of the S protein of SARS-CoV-2). In some cases, a bispecific binder provided herein can be designed to bind to two different epitopes of the same SARS-CoV-2 antigen (e.g., the S protein of SARS-CoV-2). In some cases, a bispecific binder provided herein can bind to a SARS-CoV-2 antigen (e.g., the S protein of SARS-CoV-2 or the RBD of the S protein of SARS-CoV-2) and to an epitope on a different polypeptide (e.g., an S2 polypeptide). Bispecific binders can be produced by chemically conjugating two different binders (e.g., antibodies, antigen binding fragments, and/or antibody domains) together. Bispecific binders also can be produced by fusing two antibody-producing cells, e.g., hybridomas, to make a hybrid cell line that produces two different heavy and two different light chains within the same cell, which can result in, for example, bispecific IgG molecules. See, Brinkmann and Kontermann, *MAbs*, 9(2):182-212 (2017).

In some cases, a binder (e.g., an antibody, antigen binding fragment, and/or antibody domain) provided herein can be fused or conjugated (e.g., covalently or non-covalently attached) to another polypeptide or other moiety to provide a fusion protein or conjugate. For example, a binder (e.g., an antibody, antigen binding fragment, and/or antibody domain) provided herein can be conjugated (e.g., covalently or non-covalently attached) to a polymer (e.g., polyethylene glycol (PEG), polyethylenimine (PEI) modified with PEG (PEI-PEG), and/or polyglutamic acid (PGA) (N-(2-Hydroxypropyl) methacrylamide (HPMA) copolymers), hyaluronic acid, a fluorescent substance, a luminescent substance, a hapten, an enzyme, a metal chelate, a drug, a radioisotope, and/or a cytotoxic agent. Any appropriate method can be used to conjugate (e.g., covalently or non-covalently attach) another polypeptide or other moiety to a binder (e.g., an antibody, antigen binding fragment, and/or antibody domain) provided herein. For example, another polypeptide or other moiety can be conjugated to a binder (e.g., an antibody, antigen binding fragment, and/or antibody domain) provided herein using the methods described in U.S. Pat. No. 8,021,661.

In some cases, a binder (e.g., an antibody, antigen binding fragment, and/or antibody domain) provided herein can be modified with a moiety that improves its stabilization and/or retention in circulation, for example, in blood, serum, or other tissues by, for example, at least 1.5-, 2-, 5-, 10-, or 50-fold. For example, a binder (e.g., an antibody, antigen binding fragment, and/or antibody domain) provided herein can be attached (e.g., covalently or non-covalently attached) to a polymer such as a substantially non-antigenic polymer. Examples of substantially non-antigenic polymers that can be used as described herein include, without limitation, polyalkylene oxides and polyethylene oxides. In some cases, a polymer used herein can have any appropriate molecule weight. For example, a polymer having an average molecular weight from about 200 Daltons to about 35,000 Daltons (e.g., from about 1,000 to about 15,000 Daltons or from about 2,000 to about 12,500 Daltons) can be used. In some cases, a binder (e.g., an antibody, antigen binding fragment, and/or antibody domain) provided herein can be attached (e.g., covalently or non-covalently) to a water soluble polymer. Examples of water soluble polymers that can be used as described herein include, without limitation, hydrophilic polyvinyl polymers, polyvinylalcohol, polyvinylpyrrolidone, polyalkylene oxide homopolymers, polyethylene glycol (PEG), polypropylene glycols, polyoxyethylenated polyols, and copolymers thereof and/or block copolymers thereof provided that the water solubility of the copolymer or block copolymers is maintained.

In some cases, a binder (e.g., an antibody, antigen binding fragment, and/or antibody domain) provided herein can be attached (e.g., covalently or non-covalently attached) to one or more polyoxyalkylenes (e.g., polyoxyethylene, polyoxypropylene, or block copolymers of polyoxyethylene and polyoxypropylene), polymethacrylates, carbomers, branched or unbranched polysaccharides, or combinations thereof. For example, a binder (e.g., an antibody, antigen binding fragment, and/or antibody domain) provided herein can be covalently attached to polyoxyethylene.

This document also provides nucleic acid molecules (e.g., isolated nucleic acid molecules) having a nucleic acid sequence encoding at least part of a binder (e.g., an antibody, antigen binding fragment, and/or antibody domain) provided herein. For example, an isolated nucleic acid molecule provided herein can include a nucleic acid sequence encoding a heavy chain variable domain such as a heavy chain variable domain as set forth in FIG. 2A or 3A or the VH domain set forth in FIG. 6, 7, 8, 9, or 10. In another example, an isolated nucleic acid molecule provided herein can include a nucleic acid sequence encoding a light chain variable domain such as a light chain variable domain as set forth in FIG. 2B or 3B. In some cases, an isolated nucleic acid molecule provided herein can include a nucleic acid sequence encoding both (a) a heavy chain variable domain such as a heavy chain variable domain as set forth in FIG. 4A or 5A and (b) a light chain variable domain such as a light chain variable domain as set forth in FIG. 4B or 5B, with or without, encoding a linker polypeptide set forth in FIG. 4C. A nucleic acid provided herein (e.g., an isolated nucleic acid molecule) can be single stranded or double stranded nucleic acid of any appropriate type (e.g., DNA, RNA, or DNA/RNA hybrids).

This document also provides vectors (e.g., plasmid vectors or viral vectors) containing one or more nucleic acids provided herein. An example of a plasmid vector that can be designed to include one or more nucleic acids having a nucleic acid sequence encoding at least part of a binder (e.g., an antibody, antigen binding fragment, and/or antibody domain) provided herein includes, without limitation, phagemids. Examples of viral vectors that can be designed to include one or more nucleic acids having a nucleic acid sequence encoding at least part of a binder (e.g., an antibody, antigen binding fragment, and/or antibody domain) provided herein include, without limitation, retroviral vectors, parvovirus-based vectors (e.g., adenoviral-based vectors and adeno-associated virus (AAV)-based vectors), lentiviral vectors (e.g., herpes simplex (HSV)-based vectors), poxviral vectors (e.g., vaccinia virus-based vectors and fowlpox virus-based vectors), and hybrid or chimeric viral vectors. For example, a viral vector having an adenoviral backbone with lentiviral components such as those described elsewhere (Zheng et al., *Nat. Biotech.*, 18(2): 176-80 (2000); WO 98/22143; WO 98/46778; and WO 00/17376) or viral vectors having an adenoviral backbone with AAV components such as those described elsewhere (Fisher et al., *Hum. Gene Ther.*, 7:2079-2087 (1996)) can be designed to include one or more nucleic acids having a nucleic acid sequence encoding at least part of a binder (e.g., an antibody, antigen binding fragment, and/or antibody domain) provided herein.

A vector provided herein (e.g., a plasmid vector or viral vector provided herein) can include any appropriate promoter and other regulatory sequence (e.g., transcription and translation initiation and termination codons) operably linked the nucleic acid sequence encoding at least part of a binder (e.g., an antibody, antigen binding fragment, and/or antibody domain) provided herein. In some cases, a promoter used to drive expression can be a constitutive promotor or a regulatable promotor. Examples of regulatable promoters that can be used as described herein include, without limitation, inducible promotors, repressible promotors, and tissue-specific promoters. Examples of viral promotors that can be used as described herein include, without limitation, adenoviral promotors, vaccinia virus promotors, and AAV promoters.

Any appropriate method can be used to make a nucleic acid molecule (or vector such as a plasmid vector or viral vector) having a nucleic acid sequence encoding at least part of a binder (e.g., an antibody, antigen binding fragment, and/or antibody domain) provided herein. For example, molecule cloning techniques can be used to make a nucleic acid molecule (or vector such as a plasmid vector or viral vector) having a nucleic acid sequence encoding at least part of a binder (e.g., an antibody, antigen binding fragment, and/or antibody domain) provided herein as described elsewhere (see, e.g., Sambrook et al., Molecular Cloning: A Laboratory Manual, 2nd edition, Cold Spring Harbor Laboratory, NY (1989); and Ausubel et al., Current Protocols in Molecular Biology, Green Publishing Associates and John Wiley & Sons, New York, N.Y. (1994)).

This document also provides host cells that include a nucleic acid provided herein (e.g., a nucleic acid having a nucleic acid sequence encoding at least part of a binder (e.g., an antibody, antigen binding fragment, and/or antibody domain) provided herein). Host cells that can be designed to include one or more nucleic acids provided herein can be prokaryotic cells or eukaryotic cells. Examples of prokaryotic cells that can be designed to include a nucleic acid provided herein include, without limitation, *E. coli* (e.g., Tb-1, TG-1, DH5α, XL-Blue MRF (Stratagene), SA2821, or Y1090 cells), *Bacillus subtilis, Salmonella typhimurium, Serratia marcescens*, or *Pseudomonas* (e.g., *P. aerugenosa*) cells. Examples of eukaryotic cells that can be designed to include a nucleic acid provided herein include, without limitation, insect cells (e.g., Sf9 or Ea4 cells), yeast cells (e.g., *S. cerevisiae* cells), and mammalian cells (e.g., mouse, rat, hamster, monkey, or human cells). For example, VERO cells, HeLa cells, 3T3 cells, chinese hamster ovary (CHO) cells, W138 BHK cells, COS-7 cells, and MDCK cells can be designed to include a nucleic acid provided herein. Any appropriate method can be used to introduce one or more nucleic acids provided herein (e.g., a vector such as a plasmid vector or viral vector having a nucleic acid sequence encoding at least part of a binder provided herein) into a host cell. For example, calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, electroporation, or combinations thereof can be used to introduce a nucleic acid provided herein into a host cell (see, e.g., Sambrook et al., Molecular Biology: A Laboratory Manual, Cold Spring Harbor Laboratory, NY (1989); Davis et al., Basic Methods in Molecular Biology (1986); and Neumann et al., *EMBO J.*, 1:841 (1982)).

In some cases, a binder (e.g., an antibody, antigen binding fragment, and/or antibody domain) provided herein can be produced using a method that includes (a) introducing nucleic acid encoding the polypeptide into a host cell; (b) culturing the host cell in culture medium under conditions sufficient to express the polypeptide; (c) harvesting the polypeptide from the cell or culture medium; and (d) purifying the polypeptide (e.g., to reach at least 50, 60, 70, 80, 90, 95, 97, 98, or 99 percent purity).

In some cases, a binder (e.g., an antibody, antigen binding fragment, and/or antibody domain) provided herein, a nucleic acid provided herein, a vector provided herein (e.g., a viral vector), and/or a host cell provided herein can be formulated as a pharmaceutical composition for administration to a mammal (e.g. a human) having COVID-19 (or a viral infection caused by SARS-CoV-2) to treat that mammal. In some cases, a binder (e.g., an antibody, antigen binding fragment, and/or antibody domain) provided herein, a nucleic acid provided herein, a vector provided herein (e.g., a viral vector), and/or a host cell provided herein can be formulated as a pharmaceutical composition for prophylactic administration to a mammal (e.g. a human) to reduce the mammal's susceptibility to COVID-19 (or a viral infection caused by SARS-CoV-2) and/or to reduce the severity of COVID-19 (or a viral infection caused by SARS-CoV-2) in a mammal (e.g., a human) should that mammal become infected with SARS-CoV-2. For example, a binder (e.g., an antibody, antigen binding fragment, and/or antibody domain) provided herein having the ability to bind to a SARS-CoV-2 antigen (e.g., the S protein of SARS-CoV-2 or the RBD of the S protein of SARS-CoV-2) can be formulated as a pharmaceutical composition for administration to a mammal (e.g. a human). In some cases, a pharmaceutical composition provided herein can include a pharmaceutically acceptable carrier such as a buffer, a salt, a surfactant, a sugar, a tonicity modifier, or combinations thereof as, for example, described elsewhere (Gervasi, et al., *Eur. J. Pharmaceutics and Biopharmaceutics*, 131:8-24 (2018)). Examples of pharmaceutically acceptable carriers that can be used to make a pharmaceutical composition provided herein include, without limitation, water, lactic acid, citric acid, sodium chloride, sodium citrate, sodium succinate, sodium phosphate, a surfactant (e.g., polysorbate 20, polysorbate 80, or poloxamer 188), dextran 40, or a sugar (e.g., sorbitol, mannitol, sucrose, dextrose, or trehalose), or combinations thereof. For example, a pharmaceutical composition designed to include a binder (e.g., an antibody, antigen binding fragment, and/or antibody domain) provided herein (or a nucleic acid, a vector, or a host cell provided herein) can be formulated to include a buffer (e.g., an acetate, citrate, histidine, succinate, phosphate, or hydroxymethylaminomethane (Tris) buffer), a surfactant (e.g., polysorbate 20, polysorbate 80, or poloxamer 188), and a sugar such as sucrose. Other ingredients that can be included within a pharmaceutical composition provided herein include, without limitation, amino acids such as glycine or arginine, an antioxidants such as ascorbic acid, methionine, or ethylenediaminetetraacetic acid (EDTA), antiviral agents such as Remdesivir, Galidesivir, Favipiravir, or combinations thereof. For example, a pharmaceutical composition provided herein can be formulated to include one or more binders (e.g., one or more antibodies, one or more antigen binding fragments, and/or one or more antibody domains) provided herein in combination with one or more antiviral agents such as Remdesivir, Galidesivir, and/or Favipiravir.

In some cases, when a pharmaceutical composition is formulated to include one or more binders (e.g., one or more antibodies, one or more antigen binding fragments, and/or one or more antibody domains) provided herein, any appropriate concentration of the binder can be used. For example, a pharmaceutical composition provided herein can be formulated to be a liquid that includes from about 1 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 2 mg to about 200 mg, from about 10 mg to about 300 mg, from about 25 mg to about 300 mg, from about 50 mg to about 150 mg, or from about 150 mg to about 300 mg) of a binder (e.g., an antibody, antigen binding fragment, and/or antibody domain) provided herein per mL. In another example, a pharmaceutical composition provided herein can be formulated to be a solid or semi-solid that includes from about 0.5 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 10 mg to about 300 mg, from about 25 mg to about 300 mg, from about 50 mg to about 150 mg, or from about 150 mg to about 300 mg) of a binder (e.g., an antibody, antigen binding fragment, and/or antibody domain) provided herein. In some cases, a pharmaceutical composition containing a binder (e.g., an antibody, antigen binding fragment, and/or antibody domain) provided herein can be formulated as a dosage form with a titer of the binder being from about $1 \times 10^5$ to about $1 \times 10^{12}$ (e.g., from about $1 \times 10^5$ to about $1 \times 10^{10}$, from about $1 \times 10^5$ to about $1 \times 10^8$, from about $1 \times 10^6$ to about $1 \times 10^{12}$, from about $1 \times 10^6$ to about $1 \times 10^{12}$, from about $1 \times 10^8$ to about $1 \times 10^{12}$, from about $1 \times 10^9$ to about $1 \times 10^{12}$, from about $1 \times 10^6$ to about $1 \times 10^{11}$, or from about $1 \times 10^7$ to about $1 \times 10^{10}$).

In some cases, when a pharmaceutical composition is formulated to include one or more nucleic acids (e.g., vectors such as viral vectors) encoding at least part of a binder (e.g., an antibody, antigen binding fragment, and/or antibody domain) provided herein, any appropriate concentration of the nucleic acid can be used. For example, a pharmaceutical composition provided herein can be formulated to be a liquid that includes from about 0.5 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 2 mg to about 200 mg, from about 10 mg to about 300 mg, from about 25 mg to about 300 mg, from about 50 mg to about 150 mg, or from about 150 mg to about 300 mg) of a nucleic acid provided herein per mL. In another example, a pharmaceutical composition provided herein can be formulated to be a solid or semi-solid that includes from about 0.5 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 10 mg to about 300 mg, from about 25 mg to about 300 mg, from about 50 mg to about 150 mg, or from about 150 mg to about 300 mg) of a nucleic acid provided herein.

In some cases, a pharmaceutical composition designed to include a binder (e.g., an antibody, antigen binding fragment, and/or antibody domain) provided herein can be formulated to include one or more agents capable of reducing aggregation of the the binder when formulated. Examples of such agents that can be used as described herein include, without limitation, methionine, arginine, lysine, aspartic acid, glycine, glutamic acid, and combinations thereof. In some cases, one or more of these amino acids can be included within the formulation at a concentration from about 0.5 mM to about 145 mM (e.g., from about 1 mM to about 145 mM, from about 10 mM to about 145 mM, from about 100 mM to about 145 mM, from about 0.5 mM to about 125 mM, from about 0.5 mM to about 100 mM, from about 0.5 mM to about 75 mM, or from about 10 mM to about 100 mM).

A pharmaceutical composition provided herein can be in any appropriate form. For example, a pharmaceutical composition provided herein can designed to be a liquid, a semi-solid, or a solid. In some cases, a pharmaceutical composition provided herein can be a liquid solution (e.g., an injectable and/or infusible solution), a dispersion, a suspension, a tablet, a pill, a powder, a microemulsion, a liposome, or a suppository. In some cases, a pharmaceutical composition provided herein can be lyophilized. In some cases, a pharmaceutical composition provided herein (e.g., a pharmaceutical composition that includes one or more binders (e.g., one or more antibodies, one or more antigen binding fragments, and/or one or more antibody domains) provided herein can be formulated with a carrier or coating designed to protect against rapid release. For example, a pharmaceutical composition provided herein can be formulated as a controlled release formulation or as a regulated release formulation as described elsewhere (U.S. Patent Application Publication Nos. 2019/0241667; 2019/0233522; and 2019/0233498).

This document also provides methods for administering a composition (e.g., a pharmaceutical composition provided herein) containing one or more binders (e.g., one or more antibodies, one or more antigen binding fragments, and/or one or more antibody domains) provided herein (or a nucleic acid, vector, or host cell provided herein) to a mammal (e.g., a human). For example, a composition (e.g., a pharmaceutical composition provided herein) containing one or more binders (e.g., one or more antibodies, one or more antigen binding fragments, and/or one or more antibody domains) provided herein (or a nucleic acid, vector, and/or host cell provided herein) can be administered to a mammal (e.g., a human) having COVID-19 (or a viral infection caused by SARS-CoV-2) to treat that mammal. In some cases, a composition (e.g., a pharmaceutical composition provided herein) containing one or more binders (e.g., one or more antibodies, one or more antigen binding fragments, and/or one or more antibody domains) provided herein (or a nucleic acid, vector, and/or host cell provided herein) can be administered prophylactically to a mammal (e.g. a human) to reduce the mammal's susceptibility to COVID-19 (or a viral infection caused by SARS-CoV-2) and/or to reduce the severity of COVID-19 (or a viral infection caused by SARS-CoV-2) in a mammal (e.g., a human) should that mammal become infected with SARS-CoV-2.

Any appropriate method can be used to administer a composition (e.g., a pharmaceutical composition) provided herein to a mammal (e.g., a human). For example, a composition provided herein (e.g., a pharmaceutical composition containing one or more binders provided herein such as one or more antibodies, one or more antigen binding fragments, and/or one or more antibody domains provided herein can be administered to a mammal (e.g., a human) intravenously (e.g., via an intravenous injection or infusion), subcutaneously (e.g., via a subcutaneous injection), intraperitoneally (e.g., via an intraperitoneal injection), orally, via inhalation, or intramuscularly (e.g., via intramuscular injection). In some cases, the route and/or mode of administration of a composition (e.g., a pharmaceutical composition provided herein) can be adjusted for the mammal being treated.

In some cases, an effective amount of a composition containing one or more binders (e.g., one or more antibodies, one or more antigen binding fragments, and/or one or more antibody domains) provided herein (or a nucleic acid, vector, or host cell provided herein) (e.g., a pharmaceutical composition provided herein) can be an amount that reduces the severity of COVID-19 (or the viral infection caused by SARS-CoV-2) and/or reduces the duration of COVID-19 (or the viral infection caused by SARS-CoV-2) within a mammal without producing significant toxicity to the mammal. In some cases, an effective amount of a composition containing one or more binders (e.g., one or more antibodies, one or more antigen binding fragments, and/or one or more antibody domains) provided herein (or a nucleic acid, vector, or host cell provided herein) (e.g., a pharmaceutical composition provided herein) can be an amount that prophylactically reduces a mammal's susceptibility to COVID-19 (or a viral infection caused by SARS-CoV-2) and/or that prophylactically reduces the severity of COVID-19 (or a viral infection caused by SARS-CoV-2) in a mammal (e.g., a human) should that mammal become infected with SARS-CoV-2. For example, an effective amount of a binder (e.g., an antibody, antigen binding fragment, and/or antibody domain) provided herein can be from about 0.01 to about 30 mg/kg (e.g., about 0.01 to about 25 mg/kg, about 0.1 to about 30 mg/kg, about 0.15 to about 25 mg/kg, about 0.2 to about 20 mg/kg, about 0.5 to about 20 mg/kg, about 1 to about 30 mg/kg, about 1 to about 25 mg/kg, about 1 to about 20 mg/kg, about 2 to about 20 mg/kg, about 5 to about 30 mg/kg, about 10 to about 30 mg/kg, about 15 to about 30 mg/kg, about 20 to about 30 mg/kg, or about 3 to about 30 mg/kg). The effective amount can remain constant or can be adjusted as a sliding scale or variable dose depending on the mammal's response to treatment. Various factors can influence the actual effective amount used for a particular application. For example, the severity of COVID-19 (or a viral infection caused by SARS-CoV-2) when treating a mammal having such an infection, the susceptibility of the mammal to COVID-19 (or a viral infection caused by SARS-CoV-2) when prophylactically administering the composition, the route of administration, the age and general health condition of the mammal, excipient usage, the possibility of co-usage with other therapeutic or prophylactic treatments such as use of other agents (e.g., antiviral agents such as Remdesivir, Galidesivir, and/or Favipiravir), and the judgment of the treating physician may require an increase or decrease in the actual effective amount of a composition provided herein (e.g., a pharmaceutical composition containing one or more binders provided herein) that is administered.

In some cases, an effective frequency of administration of a composition containing one or more binders (e.g., one or more antibodies, one or more antigen binding fragments, and/or one or more antibody domains) provided herein (or a nucleic acid, vector, or host cell provided herein) (e.g., a pharmaceutical composition provided herein) can be a frequency that reduces the severity of COVID-19 (or the viral infection caused by SARS-CoV-2) and/or reduces the duration of COVID-19 (or the viral infection caused by SARS-CoV-2) within a mammal without producing significant toxicity to the mammal. In some cases, an effective frequency of administration of a composition containing one or more binders (e.g., one or more antibodies, one or more antigen binding fragments, and/or one or more antibody domains) provided herein (or a nucleic acid, vector, or host cell provided herein) (e.g., a pharmaceutical composition provided herein) can be a frequency that prophylactically reduces a mammal's susceptibility to COVID-19 (or a viral infection caused by SARS-CoV-2) and/or that prophylactically reduces the severity of COVID-19 (or a viral infection caused by SARS-CoV-2) in a mammal (e.g., a human) should that mammal become infected with SARS-CoV-2. For example, an effective frequency of administration of a pharmaceutical composition provided herein such as a pharmaceutical composition containing one or more binders provided herein can be from about twice daily to about once a year (e.g., from about twice daily to about once a month, from about twice daily to about once a week, from about one daily to about once a month, or from one once daily to about once a week). In some cases, the frequency of administration of a pharmaceutical composition provided herein such as a pharmaceutical composition containing one or more binders provided herein can be daily. The frequency of administration of a pharmaceutical composition provided herein such as a pharmaceutical composition containing one or more binders provided herein can remain constant or can be variable during the duration of treatment. Various factors can influence the actual effective frequency used for a particular application. For example, the severity of COVID-19 (or a viral infection caused by SARS-CoV-2) when treating a mammal having such an infection, the susceptibility of the mammal to COVID-19 (or a viral infection caused by SARS-CoV-2) when prophylactically administering the composition, the route of administration, the age and general health condition of the mammal, excipient usage, the possibility of co-usage with other therapeutic or prophylactic treatments such as use of other agents (e.g., antiviral agents such as Remdesivir, Galidesivir, and/or Favipiravir), and the judgment of the treating physician may require an increase or decrease in the actual effective frequency of administration of a composition provided herein (e.g., a pharmaceutical composition containing one or more binders provided herein).

In some cases, an effective duration of administration of a composition containing one or more binders (e.g., one or more antibodies, one or more antigen binding fragments, and/or one or more antibody domains) provided herein (or a nucleic acid, vector, or host cell provided herein) (e.g., a pharmaceutical composition provided herein) can be a duration that reduces the severity of COVID-19 (or the viral infection caused by SARS-CoV-2) and/or reduces the duration of COVID-19 (or the viral infection caused by SARS-CoV-2) within a mammal without producing significant toxicity to the mammal. In some cases, an effective duration of administration of a composition containing one or more binders (e.g., one or more antibodies, one or more antigen binding fragments, and/or one or more antibody domains) provided herein (or a nucleic acid, vector, or host cell provided herein) (e.g., a pharmaceutical composition provided herein) can be a duration that prophylactically reduces a mammal's susceptibility to COVID-19 (or a viral infection caused by SARS-CoV-2) and/or that prophylactically reduces the severity of COVID-19 (or a viral infection caused by SARS-CoV-2) in a mammal (e.g., a human) should that mammal become infected with SARS-CoV-2. For example, an effective duration of administration of a pharmaceutical composition provided herein such as a pharmaceutical composition containing one or more binders provided herein can vary from a single time point of administration to several weeks to several years (e.g., 5, 10, 15, or more years). Multiple factors can influence the actual effective duration used for a particular application. For example, the severity of COVID-19 (or a viral infection caused by SARS-CoV-2) when treating a mammal having such an infection, the susceptibility of the mammal to COVID-19 (or a viral infection caused by SARS-CoV-2) when prophylactically administering the composition, the route of administration, the age and general health condition of the mammal, excipient usage, the possibility of co-usage with other therapeutic or prophylactic treatments such as use of other agents (e.g., antiviral agents such as Remdesivir, Galidesivir, and/or Favipiravir), and the judgment of the treating physician may require an increase or decrease in the actual effective duration of administration of a composition provided herein (e.g., a pharmaceutical composition containing one or more binders provided herein).

In some cases, a binder (e.g., an antibody, antigen binding fragment, and/or antibody domain) provided herein can be used to detect the presence or absence of SARS-CoV-2 in vitro, in situ, or in vivo (e.g., in vivo imaging within a mammal such as a human). For example, a binder (e.g., an antibody, antigen binding fragment, and/or antibody domain) provided herein can be designed to include a label (e.g., a covalently attached radioactive, enzymatic, colorimetric, or fluorescent label). The labelled binder can be used to detect the presence or absence of SARS-CoV-2 within a biological sample in vitro. Examples of biological samples that can be assessed using a binder (e.g., an antibody, antigen binding fragment, and/or antibody domain) provided herein include, without limitation, serum samples, plasma samples, tissue samples, biopsy samples, cell line samples, and tissue culture samples. In some cases, a biological sample that can be assessed as described herein can include mammalian body tissues and/or cells such as leukocytes, ovary tissue or cells, prostate tissue or cells, heart tissue or cells, placenta tissue or cells, pancreas tissue or cells, liver tissue or cells, spleen tissue or cells, lung tissue or cells, breast tissue or cells, head and neck tissue or cells, endometrium tissue or cells, colon tissue or cells, colorectal tissue or cells, cervix tissue or cells, stomach tissue or cells, or umbilical tissue or cells that may contain SARS-CoV-2. In some cases, a binder (e.g., an antibody, antigen binding fragment, and/or antibody domain) provided herein can be immobilized, e.g., on a support, and retention of SARS-CoV-2 from a biological sample on the support can be detected, and/or vice versa. In some cases, a binder (e.g., an antibody, antigen binding fragment, and/or antibody domain) provided herein can be used in applications such as fluorescence polarization, microscopy, ELISA, centrifugation, chromatography, and/or cell sorting (e.g., fluorescence activated cell sorting).

In some cases, a binder (e.g., an antibody, antigen binding fragment, and/or antibody domain) provided herein containing a label (e.g., a covalently attached radioactive label) can be used to detect the presence or absence of SARS-CoV-2 within a mammal (e.g., a human). For example, a binder (e.g., an antibody, antigen binding fragment, and/or antibody domain) provided herein that is labelled (e.g., covalently labelled) with a radiolabel or an MRI detectable label can be administered to a mammal (e.g., a human), and that mammal can be assessed using a means for detecting the detectable label. In some cases, a mammal can be scanned to evaluate the location(s) of a labelled binder provided herein within the mammal. For example, the mammal can be imaged using NMR or other tomographic techniques.

Examples of labels that can be attached (e.g., covalently or non-covalently attached) to a binder (e.g., an antibody, antigen binding fragment, and/or antibody domain) provided herein include, without limitation, radiolabels such as $^{131}$I, $^{111}$In, $^{123}$I, $^{99m}$Tc, $^{32}$P, $^{33}$P, $^{125}$I, $^{3}$H, $^{14}$C, and $^{18}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as a peroxidase or a phosphatase. In some cases, short-range radiation emitters such as isotopes detectable by short-range detector probes can be used.

The invention will be further described in the following examples, which do not limit the scope of the invention described in the claims.

EXAMPLES

Example 1—Obtaining Binders Having the Ability to Bind to an RBD of an S Protein of SARS-CoV-2

Large phage displayed antibody fragments and antibody domain libraries were panned and screened to identify monoclonal antigen binding fragments and monoclonal antibody domains that bind to an RBD of an S protein of SARS-CoV-2. To identify such monoclonal antibodies, monoclonal antigen binding fragments, and monoclonal antibody domains, the SARS-CoV-2 RBD set forth in FIG. 1 and the SARS-CoV-2 RBD set forth in FIG. 1 fused to Fc were used for panning of human Fab, scFv, and VH domain phage-displayed libraries.

Two Fab antibody fragments (Clones: #1 and #2; FIGS. 2 and 3), two scFv antibodies (Clones: #3 and #4 FIGS. 4 and 5), and VH domains (Clones: #5, #6, #7, #8, and #9; FIGS. 6-10) were identified.

Binding affinity and specificity to the SARSCoV-2 RBD was tested using an ELISA and recombinant soluble ACE2 receptor extracellular domain as competitor. Clones #1-#9 exhibited high affinity binding having $EC_{50}$ values of 20 nM, 2 nM, 8 nM, 10 nM, 20 nM, 6 nM, 4 nM, 25 nM, and 60 nM, respectively. Clone #1, Clone #2, Clone #3, Clone #4, Clone #6, Clone #7, Clone #8, and Clone #9 also competed with ACE2 for binding to RBD, demonstrating that they can neutralize the virus by competing with the receptor. Clone #5 did not compete to any significant degree with ACE2, but is expected to induce antibody-dependent cell-mediated cytotoxicity (ADCC), thereby leading to killing of infected cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated antibody comprising:
   (i) a heavy chain variable domain or region comprising the amino acid sequences set forth in SEQ ID NO:1, SEQ ID NO:2, and SEQ ID NO:3, and a light chain variable domain or region comprising the amino acid sequences set forth in SEQ ID NO:9, SEQ ID NO:10, and SEQ ID NO:11;
   (ii) a heavy chain variable domain or region comprising the amino acid sequences set forth in SEQ ID NO:17, SEQ ID NO:18, and SEQ ID NO:19, and a light chain variable domain or region comprising the amino acid sequences set forth in SEQ ID NO:25, SEQ ID NO:26, and SEQ ID NO:27;
   (iii) a heavy chain variable domain or region comprising the amino acid sequences set forth in SEQ ID NO:73, SEQ ID NO:74, and SEQ ID NO:75; or
   (iv) a heavy chain variable domain or region comprising the amino acid sequences set forth in SEQ ID NO:89, SEQ ID NO:90, and SEQ ID NO:91.

2. The isolated antibody of claim 1, wherein said isolated antibody comprises said heavy chain variable domain or region and said light chain variable domain or region of said (i).

3. The isolated antibody of claim 1, wherein said isolated antibody comprises said heavy chain variable domain or region and said light chain variable domain or region of said (ii).

4. The isolated antibody of claim 1, wherein said isolated antibody comprises said heavy chain variable domain or region of said (iii).

5. The isolated antibody of claim 1, wherein said isolated antibody comprises said heavy chain variable domain or region of said (iv).

6. The isolated antibody of claim 1, wherein said isolated antibody is an isolated monoclonal antibody.

7. An isolated antigen binding fragment comprising:
(i) a heavy chain variable domain or region comprising the amino acid sequences set forth in SEQ ID NO:1, SEQ ID NO:2, and SEQ ID NO:3, and a light chain variable domain or region comprising the amino acid sequences set forth in SEQ ID NO:9, SEQ ID NO:10, and SEQ ID NO:11;
(ii) a heavy chain variable domain or region comprising the amino acid sequences set forth in SEQ ID NO:17, SEQ ID NO:18, and SEQ ID NO:19, and a light chain variable domain or region comprising the amino acid sequences set forth in SEQ ID NO:25, SEQ ID NO:26, and SEQ ID NO:27;
(iii) a heavy chain variable domain or region comprising the amino acid sequences set forth in SEQ ID NO:73, SEQ ID NO:74, and SEQ ID NO:75; or
(iv) a heavy chain variable domain or region comprising the amino acid sequences set forth in SEQ ID NO:89, SEQ ID NO:90, and SEQ ID NO:91.

8. The isolated antigen binding fragment of claim 7, wherein said isolated antigen binding fragment comprises said heavy chain variable domain or region and said light chain variable domain or region of said (i).

9. The isolated antigen binding fragment of claim 7, wherein said isolated antigen binding fragment comprises said heavy chain variable domain or region and said light chain variable domain or region of said (ii).

10. The isolated antigen binding fragment of claim 7, wherein said isolated antigen binding fragment comprises said heavy chain variable domain or region of said (iii).

11. The isolated antigen binding fragment of claim 7, wherein said isolated antigen binding fragment comprises said heavy chain variable domain or region of said (iv).

12. The isolated antigen binding fragment of claim 7, wherein said isolated antigen binding fragment is an isolated monoclonal antigen binding fragment.

13. The isolated antigen binding fragment of claim 7, wherein said isolated antigen binding fragment is an Fab.

14. An isolated antibody domain comprising:
(i) a heavy chain variable domain or region comprising the amino acid sequences set forth in SEQ ID NO:73, SEQ ID NO:74, and SEQ ID NO:75; or
(ii) a heavy chain variable domain or region comprising the amino acid sequences set forth in SEQ ID NO:89, SEQ ID NO:90, and SEQ ID NO:91.

15. The isolated antibody domain of claim 14, wherein said isolated antibody domain comprises said heavy chain variable domain or region of said (i).

16. The isolated antibody domain of claim 14, wherein said isolated antibody domain comprises said heavy chain variable domain or region of said (ii).

17. The isolated antibody domain of claim 14, wherein said isolated antibody domain is an isolated monoclonal antibody domain.

18. The isolated antibody domain of claim 14, wherein said isolated antibody domain is a VH domain.

* * * * *